(12) United States Patent
Gee et al.

(10) Patent No.: US 10,004,527 B2
(45) Date of Patent: Jun. 26, 2018

(54) ULTRASONIC SURGICAL INSTRUMENT WITH STAGED CLAMPING

(71) Applicant: Ethicon Endo-Surgery, Inc., Cincinnati, OH (US)

(72) Inventors: Jacob S. Gee, Cincinnati, OH (US); David J. Cagle, Cincinnati, OH (US); Frederick L. Estera, Cincinnati, OH (US); William B. Weisenburgh, II, Maineville, OH (US); Frederick E. Shelton, IV, Hillsboro, OH (US); Craig N. Faller, Batavia, OH (US); Shan Wan, Mason, OH (US); David A. Monroe, Milford, OH (US); Jeffrey D. Messerly, Cincinnati, OH (US); William A. Olson, Lebanon, OH (US); Richard W. Timm, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 585 days.

(21) Appl. No.: 14/552,614

(22) Filed: Nov. 25, 2014

(65) Prior Publication Data

US 2015/0148834 A1 May 28, 2015

Related U.S. Application Data

(60) Provisional application No. 61/908,920, filed on Nov. 26, 2013.

(51) Int. Cl.
*A61B 17/32* (2006.01)
*A61N 7/00* (2006.01)
(Continued)

(52) U.S. Cl.
CPC ............. *A61B 17/320092* (2013.01); *A61B 17/320068* (2013.01); *A61N 7/00* (2013.01);
(Continued)

(58) Field of Classification Search
CPC ......... A61B 2017/320094; A61B 2017/00353; A61B 17/320092; A61B 18/1442
See application file for complete search history.

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

CN 101883529 A 11/2010
JP 2014-000311 1/2014
(Continued)

OTHER PUBLICATIONS

International Search Report and Written Opinion dated Jan. 30, 2015 for Application No. PCT/US2014/067221, 10 pgs.
(Continued)

*Primary Examiner* — Anh Dang
(74) *Attorney, Agent, or Firm* — Frost Brown Todd LLC

(57) ABSTRACT

An apparatus comprises a body, a shaft assembly, and an end effector. The shaft assembly extends distally from the body. The end effector is located at a distal end of the shaft assembly. The end effector comprises an ultrasonic blade and a clamp arm. The ultrasonic blade is configured to vibrate at an ultrasonic frequency. The clamp arm comprises a clamp pad. The clamp arm is movable toward the ultrasonic blade to compress tissue between the clamp pad and the ultrasonic blade in two stages. During the first stage, the clamp arm is configured to compress tissue with only a distal portion of the clamp pad. During the second stage, the clamp arm is configured to compress tissue with the distal portion and a proximal portion of the clamp pad. Thus, the tissue compression begins at the distal portion and subsequently progresses toward the proximal portion.

19 Claims, 65 Drawing Sheets

(51) Int. Cl.
  *A61B 18/00* (2006.01)
  *A61B 18/14* (2006.01)
  *A61B 17/00* (2006.01)
  *A61B 17/28* (2006.01)
  *A61B 90/00* (2016.01)

(52) U.S. Cl.
  CPC . *A61B 18/1442* (2013.01); *A61B 2017/00353* (2013.01); *A61B 2017/2825* (2013.01); *A61B 2017/320076* (2013.01); *A61B 2017/320084* (2013.01); *A61B 2018/00011* (2013.01); *A61B 2018/0063* (2013.01); *A61B 2018/00107* (2013.01); *A61B 2090/0436* (2016.02); *A61B 2090/0472* (2016.02)

(56) References Cited

U.S. PATENT DOCUMENTS

| | | | |
|---|---|---|---|
| 5,980,510 | A | 11/1999 | Tsonton et al. |
| 6,056,735 | A | 5/2000 | Okada et al. |
| 6,193,709 | B1 | 2/2001 | Miyawaki et al. |
| 6,325,811 | B1 | 12/2001 | Messerly |
| 6,358,267 | B1 | 3/2002 | Murakami et al. |
| 6,500,176 | B1 | 12/2002 | Truckai et al. |
| 6,669,690 | B1 | 12/2003 | Okada et al. |
| 6,773,444 | B2 | 8/2004 | Messerly |
| 6,783,524 | B2 | 8/2004 | Anderson et al. |
| 6,958,070 | B2 | 10/2005 | Witt et al. |
| 7,066,936 | B2 | 6/2006 | Ryan |
| 7,074,219 | B2 | 7/2006 | Levine et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,235,073 | B2 | 6/2007 | Levine et al. |
| 7,309,849 | B2 | 12/2007 | Truckai et al. |
| 7,311,709 | B2 | 12/2007 | Truckai et al. |
| 7,354,440 | B2 | 4/2008 | Truckal et al. |
| 7,381,209 | B2 | 6/2008 | Truckai et al. |
| 7,563,269 | B2 | 7/2009 | Hashiguchi |
| 7,901,423 | B2 | 3/2011 | Stulen et al. |
| 8,057,498 | B2 | 11/2011 | Robertson |
| 8,328,834 | B2 | 12/2012 | Isaacs et al. |
| 8,348,880 | B2 | 1/2013 | Messerly et al. |
| 8,444,663 | B2 | 5/2013 | Houser et al. |
| 8,444,664 | B2 | 5/2013 | Balanev et al. |
| 8,461,744 | B2 | 6/2013 | Wiener et al. |
| 8,523,889 | B2 | 9/2013 | Stulen et al. |
| 8,535,257 | B1 | 9/2013 | Zelten et al. |
| 8,591,459 | B2 | 11/2013 | Clymer et al. |
| 8,591,536 | B2 | 11/2013 | Robertson |
| 8,623,027 | B2 | 1/2014 | Price et al. |
| 8,652,132 | B2 | 2/2014 | Tsuchiya et al. |
| 8,662,745 | B2 | 3/2014 | Mishuchenko et al. |
| 8,685,020 | B2 | 4/2014 | Weizman et al. |
| 8,974,447 | B2 | 3/2015 | Kimball et al. |
| 8,986,302 | B2 | 3/2015 | Aldridge et al. |
| 9,005,199 | B2 | 4/2015 | Beckman et al. |
| 9,023,071 | B2 | 5/2015 | Miller et al. |
| 9,192,428 | B2 | 11/2015 | Houser et al. |
| 2005/0187512 | A1* | 8/2005 | Isola ............ A61B 17/320068 604/22 |
| 2005/0192611 | A1 | 9/2005 | Houser |
| 2005/0273126 | A1 | 12/2005 | Beaupre |
| 2006/0079874 | A1 | 4/2006 | Faller et al. |
| 2006/0265035 | A1 | 11/2006 | Yachi et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0030440 | A1 | 1/2009 | Mastri et al. |
| 2009/0036914 | A1 | 2/2009 | Houser |
| 2010/0331873 | A1* | 12/2010 | Dannaher ...... A61B 17/320092 606/169 |
| 2012/0112687 | A1 | 5/2012 | Houser et al. |
| 2012/0116265 | A1 | 5/2012 | Houser et al. |
| 2013/0090576 | A1 | 4/2013 | Stulen et al. |
| 2013/0103065 | A1 | 4/2013 | Timm et al. |
| 2013/0110155 | A1* | 5/2013 | Tsuchiya ............ A61B 17/28 606/205 |
| 2013/0303949 | A1 | 11/2013 | Kawaguchi et al. |
| 2014/0005668 | A1 | 1/2014 | Rhee et al. |
| 2014/0005701 | A1 | 1/2014 | Olson et al. |
| 2014/0012297 | A1 | 1/2014 | Ross et al. |
| 2014/0012298 | A1 | 1/2014 | Cunningham et al. |
| 2014/0012299 | A1 | 1/2014 | Stoddard et al. |
| 2014/0114334 | A1 | 4/2014 | Olson et al. |
| 2014/0135804 | A1 | 5/2014 | Weisenburgh, II et al. |
| 2014/0163549 | A1 | 6/2014 | Yates et al. |
| 2014/0180002 | A1 | 6/2014 | Voic |
| 2015/0080924 | A1 | 3/2015 | Stulen et al. |
| 2015/0080925 | A1 | 3/2015 | Schulte et al. |
| 2015/0122530 | A1 | 5/2015 | Katsuda |
| 2015/0148832 | A1 | 5/2015 | Boudreaux et al. |
| 2015/0148833 | A1 | 5/2015 | Stokes et al. |
| 2015/0148835 | A1 | 5/2015 | Faller et al. |

FOREIGN PATENT DOCUMENTS

| | | |
|---|---|---|
| WO | WO 2012/116957 | 9/2012 |
| WO | WO 2013/183715 | 12/2013 |
| WO | WO 2013/062103 | 4/2015 |
| WO | WO 2015/081038 A1 | 6/2015 |
| WO | WO 2015/081039 A1 | 6/2015 |
| WO | WO 2015/081040 A1 | 6/2015 |
| WO | WO 2015/081042 A1 | 6/2015 |
| WO | WO 2013/157571 A1 | 12/2015 |

OTHER PUBLICATIONS

International Search Report and Written Opinion dated Feb. 12, 2015 for Application No. PCT/US2014/067218, 9 pgs.
International Search Report and Written Opinion dated Feb. 12, 2015 for Application No. PCT/US2014/067219, 9 pgs.
International Search Report and Written Opinion dated Feb. 12, 2015 for Application No. PCT/US2014/067225, 9 pgs.
U.S. Appl. No. 61/410,603, filed Nov. 5, 2010.
U.S. Appl. No. 14/553,142, filed Nov. 25, 2014.
U.S. Appl. No. 14/553,329, filed Nov. 25, 2014.
U.S. Appl. No. 14/553,378, filed Nov. 25, 2014.
U.S. Appl. No. 14/552,530.
U.S. Appl. No. 14/552,552.
U.S. Appl. No. 14/552,681.
U.S. Appl. No. 14/553,142.
U.S. Appl. No. 14/553,329.
U.S. Appl. No. 14/553,378.
Search report dated Jan. 15, 2018 for Chinese Patent Application No. 201480073943.5.
Office Action dated Jan. 23, 2018 for Chinese Patent Application No. 201480073943.5.

* cited by examiner

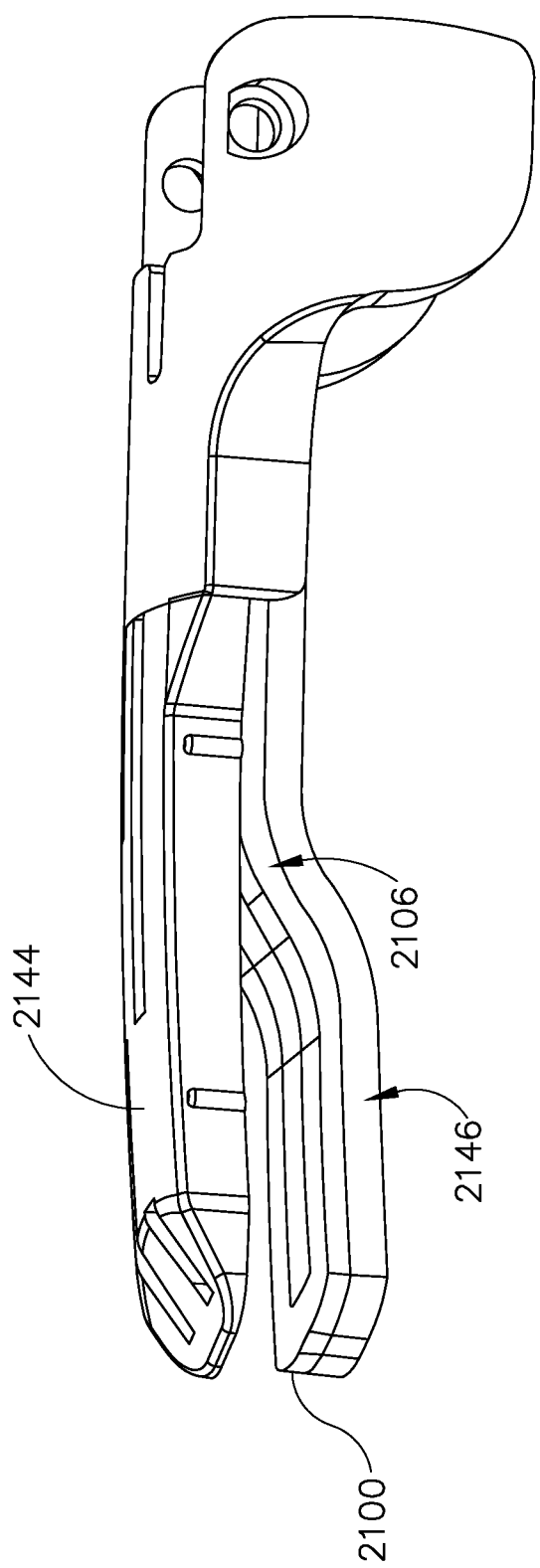

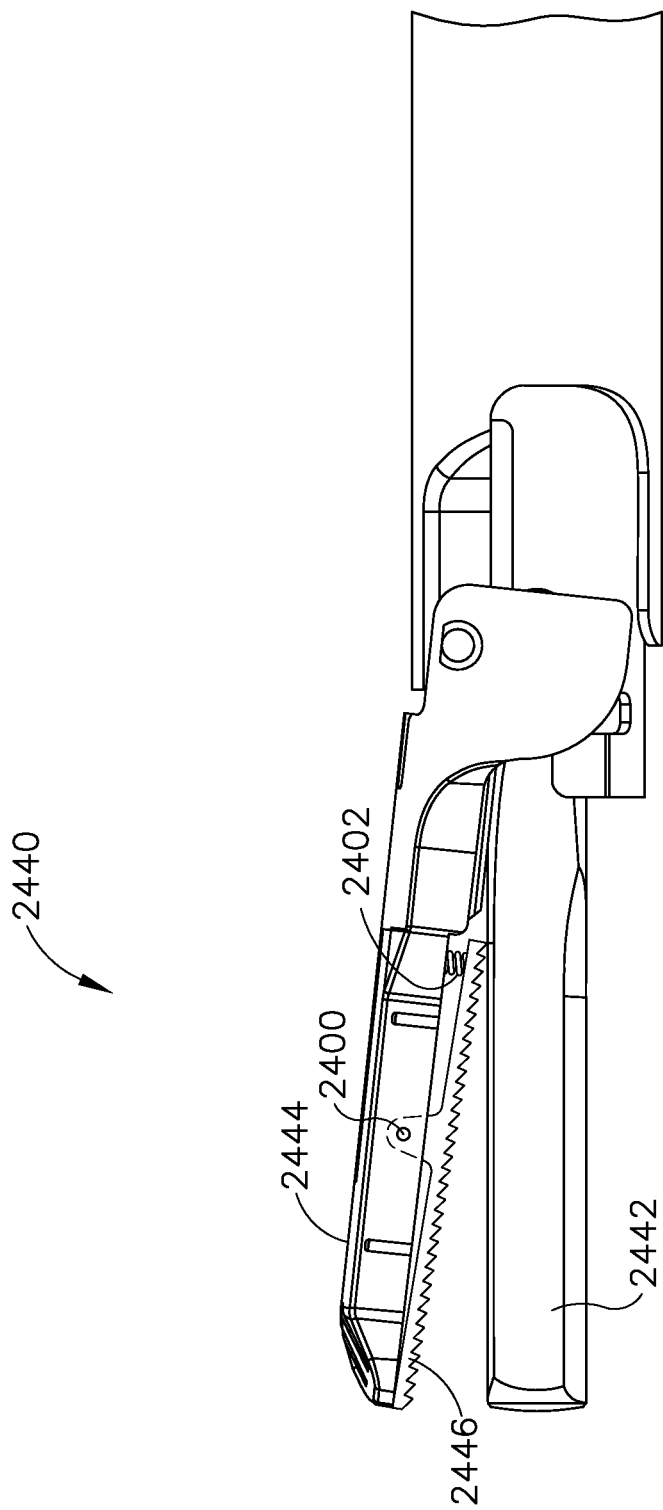

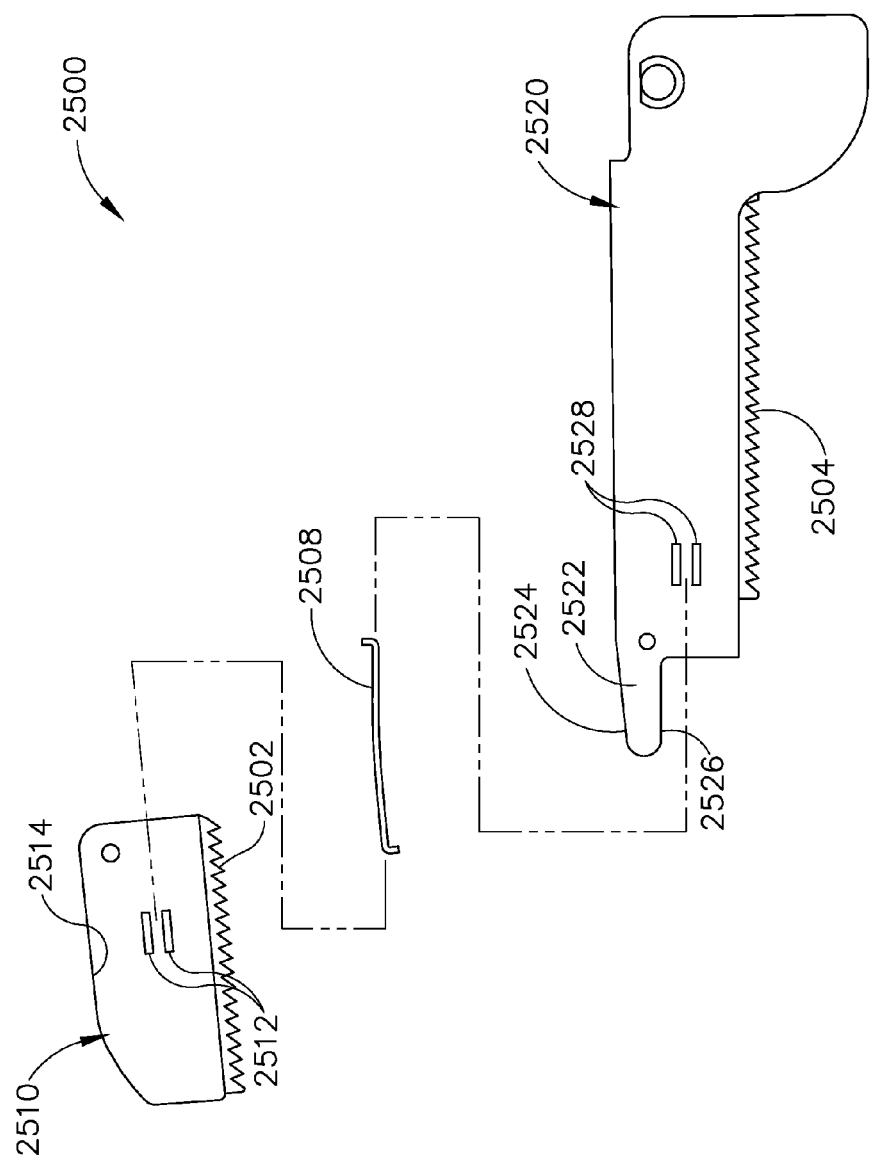

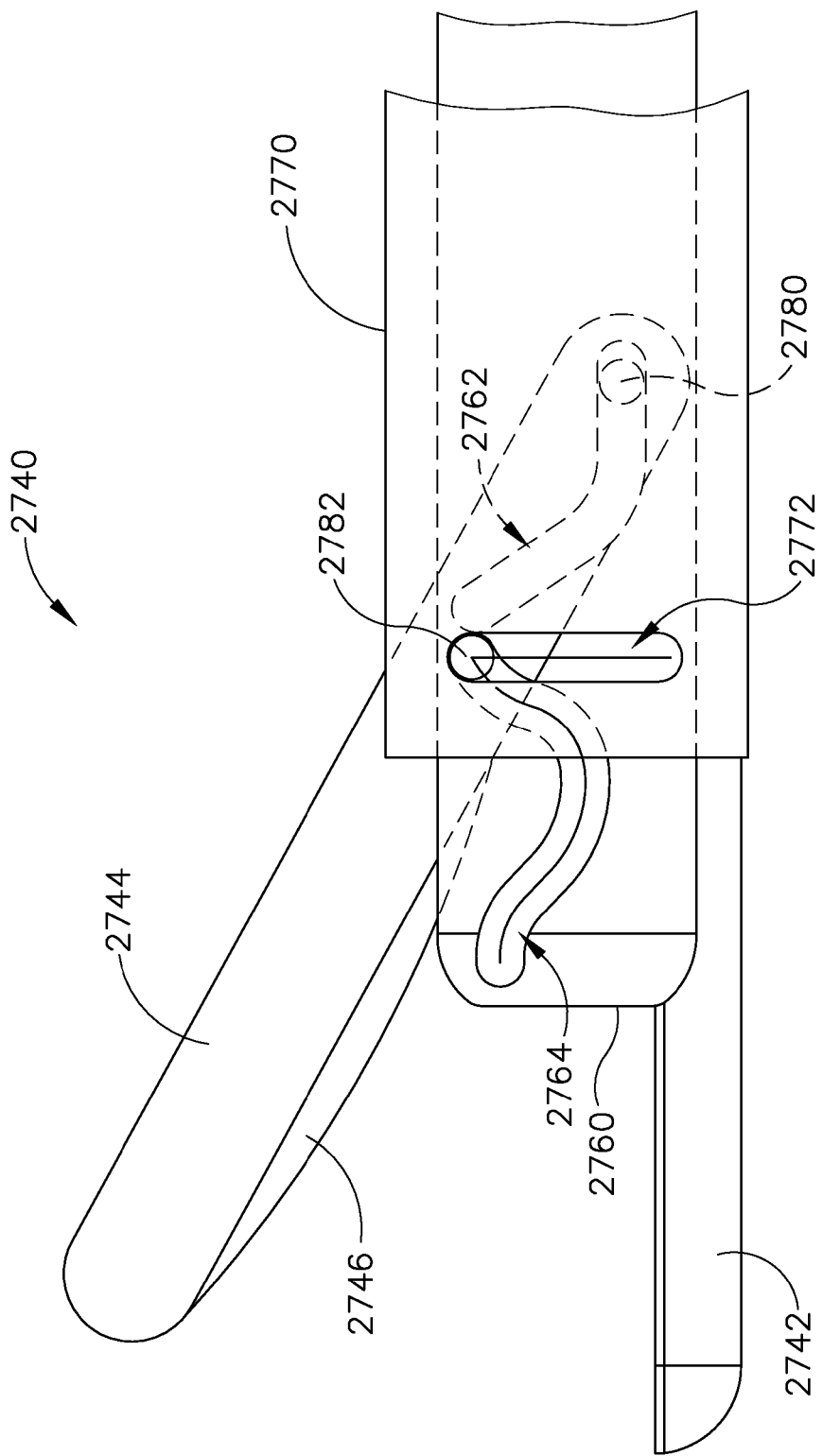

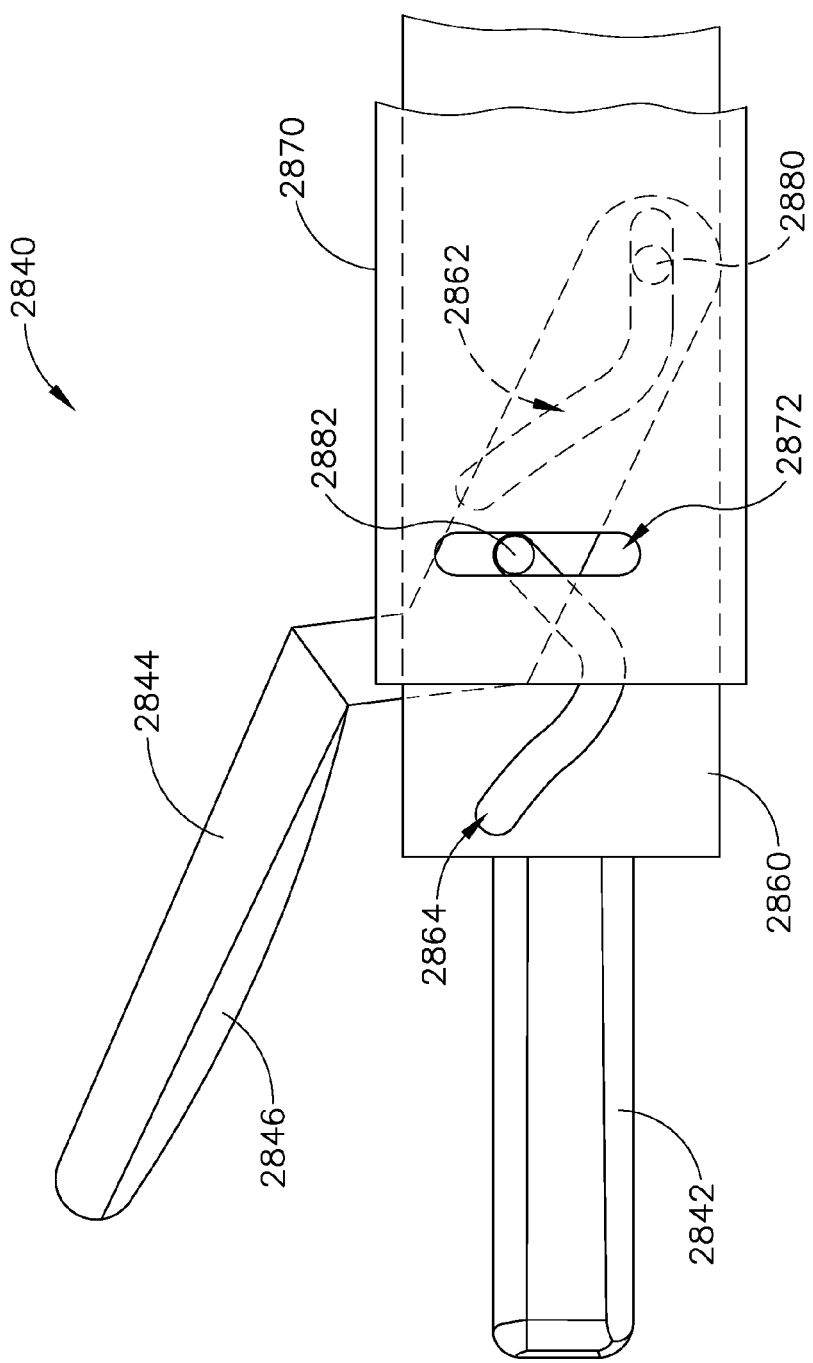

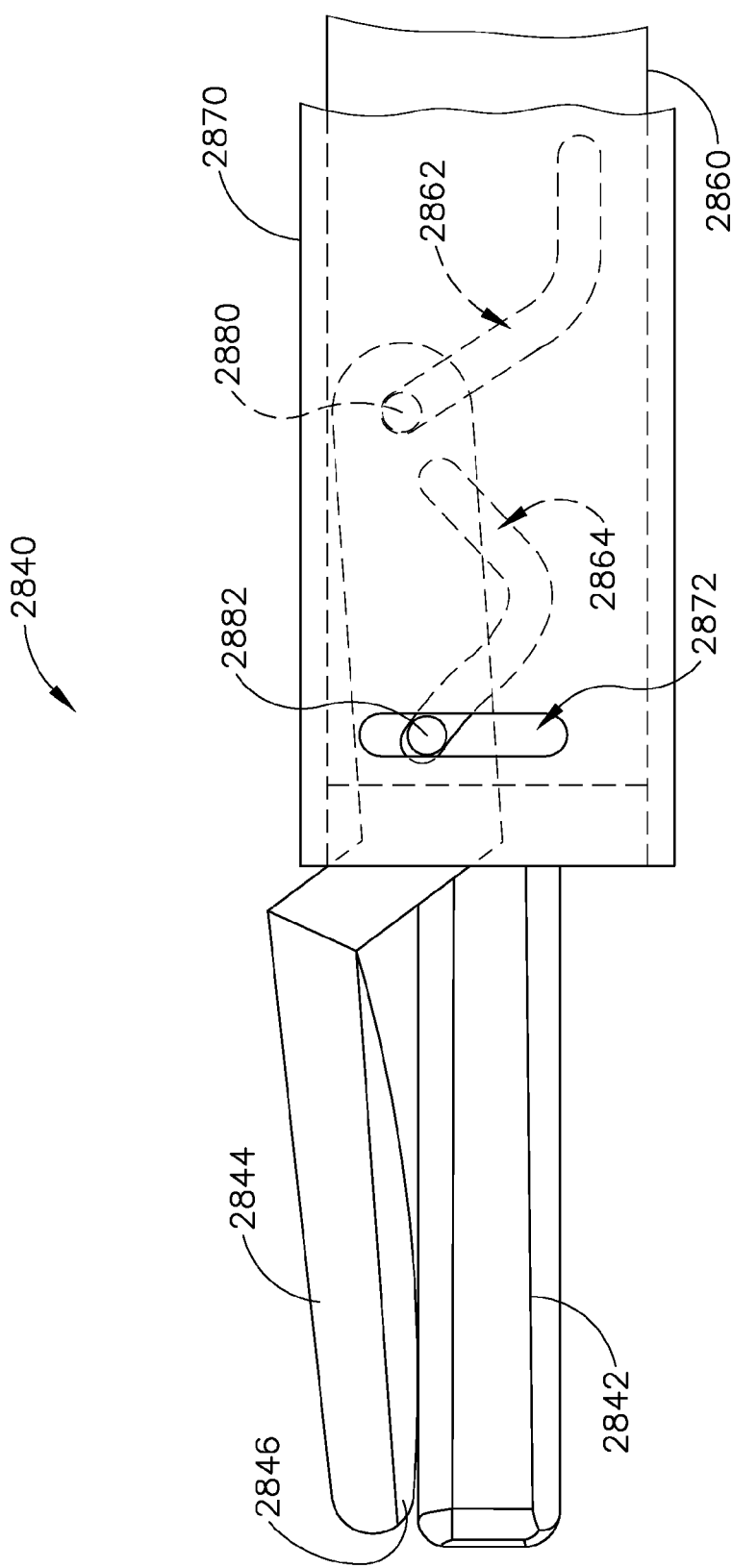

ULTRASONIC SURGICAL INSTRUMENT WITH STAGED CLAMPING

PRIORITY

This application claims priority to U.S. Provisional Patent App. No. 61/908,920, entitled "Heat Management for Ultrasonic Surgical Instrument," filed Nov. 26, 2013, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on Mar. 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, issued as U.S. Pat. No. 9,381,058 on Jul. 5, 2016, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, issued as U.S. Pat. No. 9,393,037 on Jul. 9, 2015, the disclosure of which is incorporated by reference herein; and U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 24 depicts another exemplary alternative clamp arm assembly;

FIG. 28 depicts a side elevational view of another exemplary alternative end effector, with a clamp arm in an open position;

FIG. 29 depicts an exploded view of another exemplary alternative clamp arm assembly;

FIG. 32A depicts a side elevational view of another exemplary alternative end effector, with a clamp arm in an open position;

FIG. 33A depicts a side elevational view of another exemplary alternative end effector, with a clamp arm in an open position;

FIG. 33C depicts a side elevational view of the end effector of FIG. 33A, with the clamp arm in a second closed position;

Figure 1:
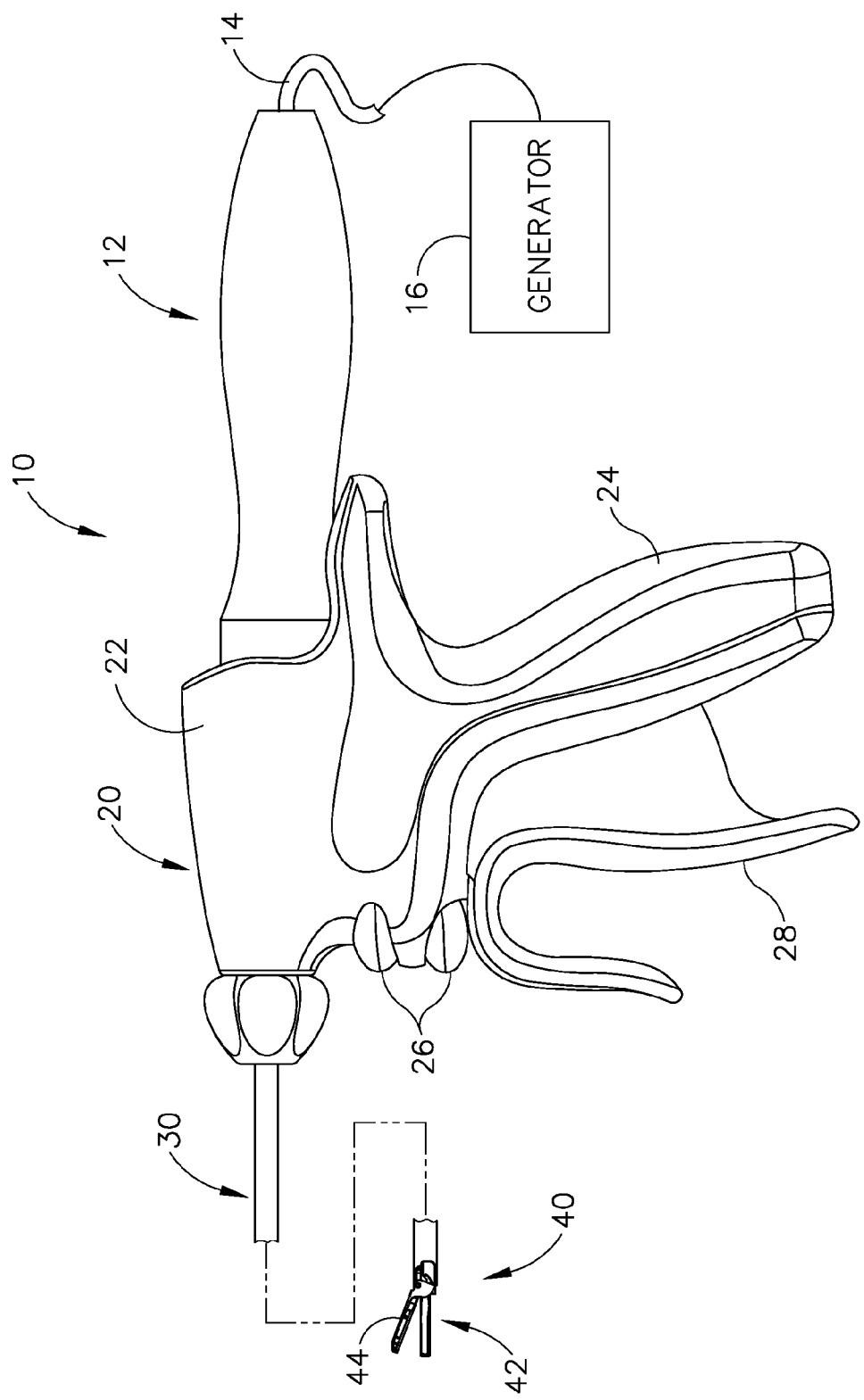
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-6B illustrate exemplary ultrasonic surgical instruments (10, 100). At least part of each instrument (10, 100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265; U.S. Pub. No. 2014/0005701, issued as U.S. Pat. No. 9,393,037 on Jul. 9, 2016; U.S. Pub. No. 2014/0114334, issued as U.S. Pat. No. 9,095,367 on Aug. 4, 2015; U.S. Pat. App. No. 61/410,603; and/or U.S. patent application Ser. No. 14/028,717, published as U.S. Pat. Pub. No. 2015/0080924 on Mar. 19, 2015. The disclosures of each of the foregoing patents, publications, and applications are incorporated by reference herein. As described therein and as will be described in greater detail below, each instrument (10, 100) is operable to cut tissue and seal or weld tissue (e.g., a blood vessel, etc.) substantially simultaneously. It should also be understood that instruments (10, 100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (10, 100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (10, 100), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
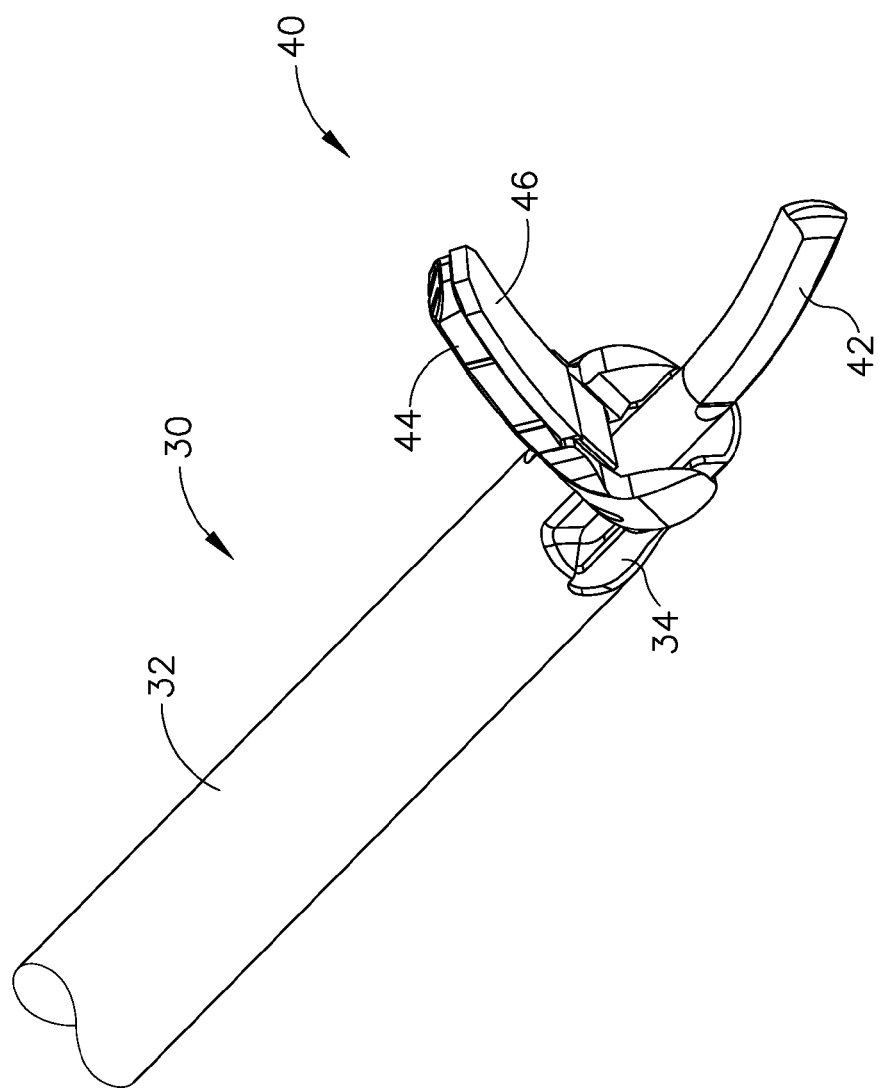
FIG. 2 depicts a perspective view of the end effector of the instrument of FIG. 1, in an open configuration.

A. Exemplary Ultrasonic Surgical Instrument for Minimally Invasive Surgical Procedures FIG. 1 illustrates an exemplary ultrasonic surgical instrument (10) that is configured to be used in minimally invasive surgical procedures (e.g., via a trocar or other small diameter access port, etc.). Instrument (10) of this example comprises a handle assembly (20), a shaft assembly (30), and an end effector (40). As shown in FIGS. 2-3B, shaft assembly (30) comprises an outer sheath (32), an inner tube (34) slidably disposed within outer sheath (32), and a waveguide (38) disposed within inner tube (34). As will be discussed in more detail below, longitudinal translation of inner tube (34) relative to outer sheath (32) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. In the present example, a resilient member biases trigger (28) away from pistol grip (24). Trigger (28) is pivotable toward pistol grip (24) to drive inner tube (34) proximally relative to outer sheath (32). When trigger (28) is thereafter released or driven away from pistol grip (24), inner tube (34) is driven distally relative to outer sheath (32). By way of example only, trigger (28) may be coupled with inner tube (34) in accordance with the teachings of various references cited herein. Other suitable ways in which trigger (28) may be coupled with inner tube (34) will be apparent to those of ordinary skill in the art in view of the teachings herein.

Figure 3A:
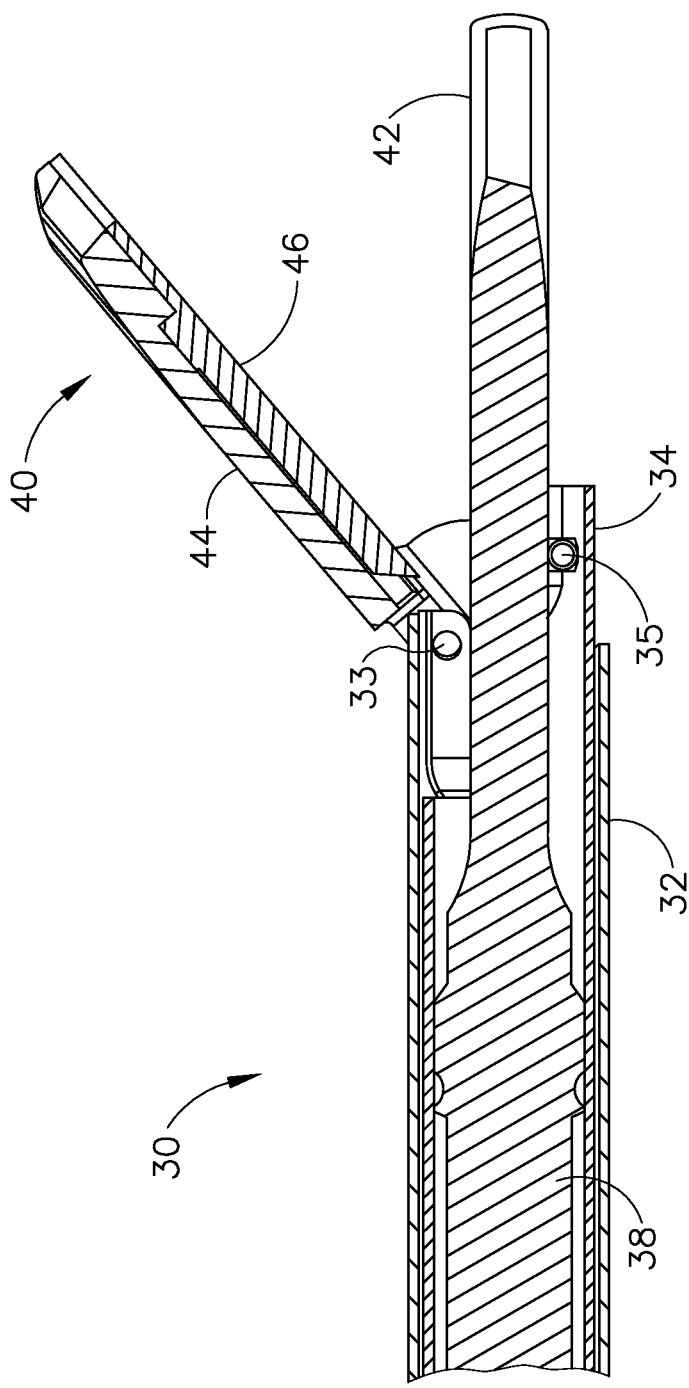
FIG. 3A depicts a side cross-sectional view of the end effector of FIG. 2, in the open configuration.
Figure 3B:
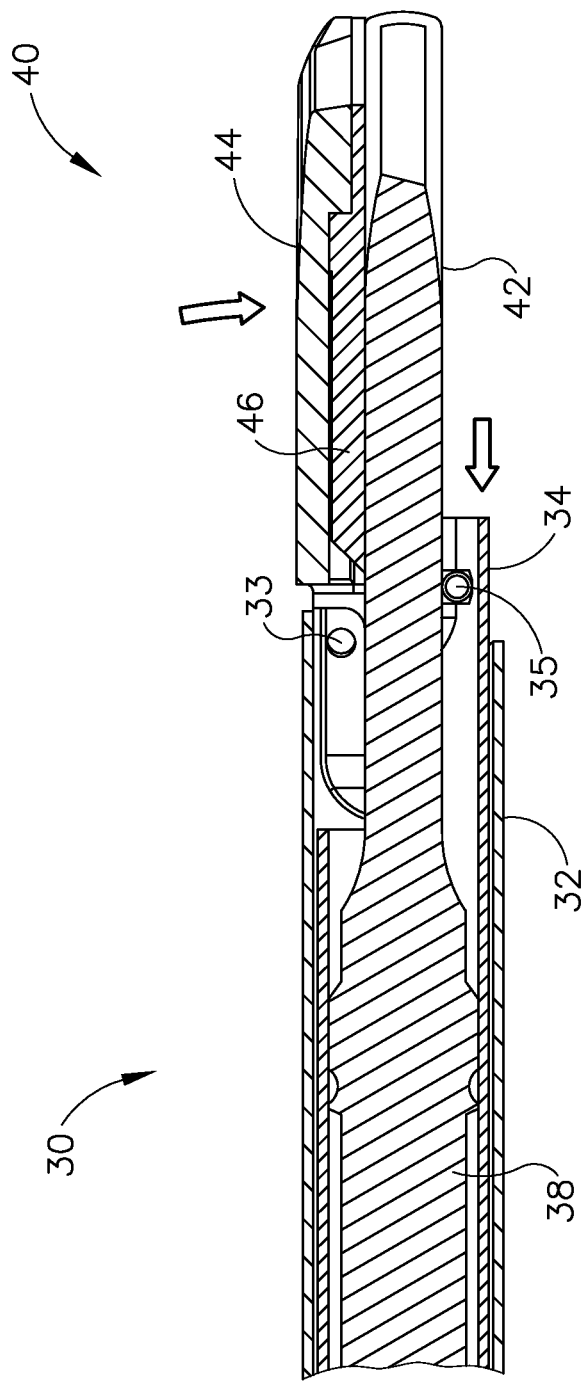
FIG. 3B depicts a side cross-sectional view of the end effector of FIG. 2, in a closed configuration.

As shown in FIGS. 2-3B, end effector (40) includes an ultrasonic blade (42) and a pivoting clamp arm (44). Clamp arm (44) includes a clamp pad (46) facing ultrasonic blade (42). Clamp arm (44) is pivotably coupled with a distal end of outer sheath (32) of shaft assembly (30), above ultrasonic blade (42), via a pin (33). A distal end of inner tube (34) is pivotably coupled with a proximal end of clamp arm (44), below ultrasonic blade (42), via another pin (35). Thus, longitudinal translation of inner tube (34) relative to outer sheath (32) causes clamp arm (44) to pivot about pin (33) toward and away from ultrasonic blade (42) to thereby clamp tissue between clamp pad (46) and ultrasonic blade (42) to transect and/or seal the tissue. In particular, as seen in the transition from FIG. 3A to FIG. 3B, proximal longitudinal translation of inner tube (34) relative to outer sheath (32) and handle assembly (20) causes clamp arm (44) to pivot toward ultrasonic blade (42); and distal longitudinal translation of inner tube (34) relative to outer sheath (32) and handle assembly (20) causes clamp arm (44) to pivot away from ultrasonic blade (42). It should therefore be understood that pivoting of trigger (28) toward pistol grip (24) will cause clamp arm (44) to pivot toward ultrasonic blade (42); and that pivoting of trigger (28) away from pistol grip (24) will cause clamp arm (44) to pivot away from ultrasonic blade (42).

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (38), which extends through shaft assembly (30) to reach ultrasonic blade (42). Waveguide (38) is secured within shaft assembly (30) via a pin (not shown), which passes through waveguide (38) and shaft assembly (30). This pin is located at a position along the length of waveguide (38) corresponding to a node associated with resonant ultrasonic vibrations communicated through waveguide (38). As noted above, when ultrasonic blade (42) is in an activated state (i.e., vibrating ultrasonically), ultrasonic blade (42) is operable to effectively cut through and seal tissue, particularly when the tissue is being clamped between clamp pad (46) and ultrasonic blade (42). It should be understood that waveguide (38) may be configured to amplify mechanical vibrations transmitted through waveguide (38). Furthermore, waveguide (38) may include features operable to control the gain of the longitudinal vibrations along waveguide (38) and/or features to tune waveguide (38) to the resonant frequency of the system.

In the present example, the distal end of ultrasonic blade (42) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (12) is energized, the distal end of ultrasonic blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (42) and clamp pad (46), the ultrasonic oscillation of ultrasonic blade (42) may simultaneously sever the tissue and denature the proteins in adjacent tissue cells, thereby providing a coagulative effect with relatively little thermal spread. In some versions, an electrical current may also be provided through ultrasonic blade (42) and/or clamp pad (46) to also seal the tissue.

An operator may activate buttons (26) to selectively activate transducer assembly (12) to thereby activate ultrasonic blade (42). In the present example, two buttons (26) are provided—one for activating ultrasonic blade (42) at a low power and another for activating ultrasonic blade (42) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun 11, 2013; U.S. Pub. No. 2012/0112687, issued as U.S. Pat. No. 9,381,058 on Jul. 5, 2016; U.S. Pub. No. 2012/0116265; U.S. Pub. No. 2014/0005701, issued as U.S. Pat. No. 9,393,037 on Jul. 9, 2016; and/or U.S. Pub. No. 2014/0114334, issued as U.S. Pat. No. 9,095,367 on Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

B. Exemplary Ultrasonic Surgical Instrument for Open Surgical Procedures

Figure 4:
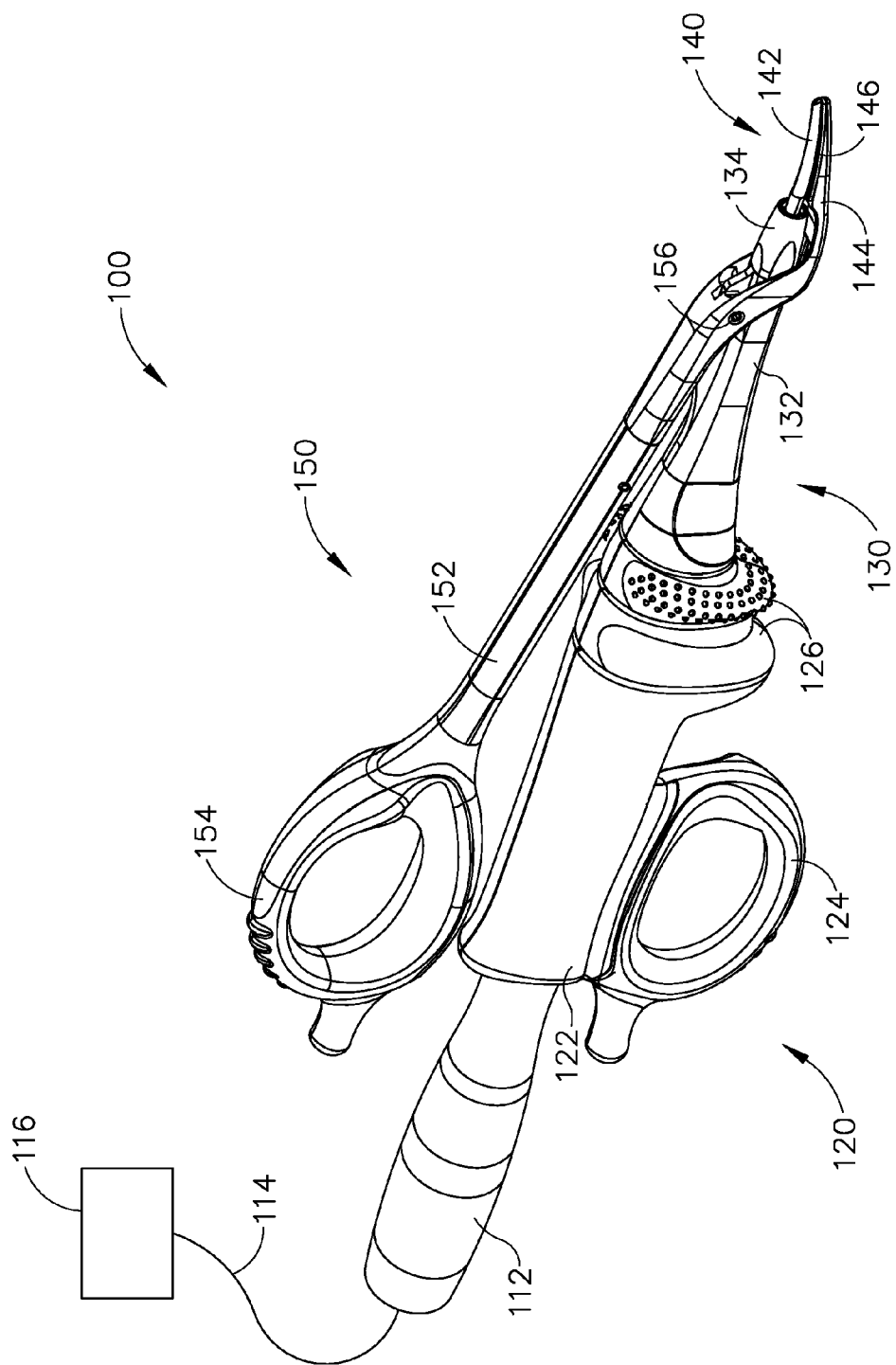
FIG. 4 depicts a perspective view of another exemplary surgical instrument.

FIG. 4 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 5:
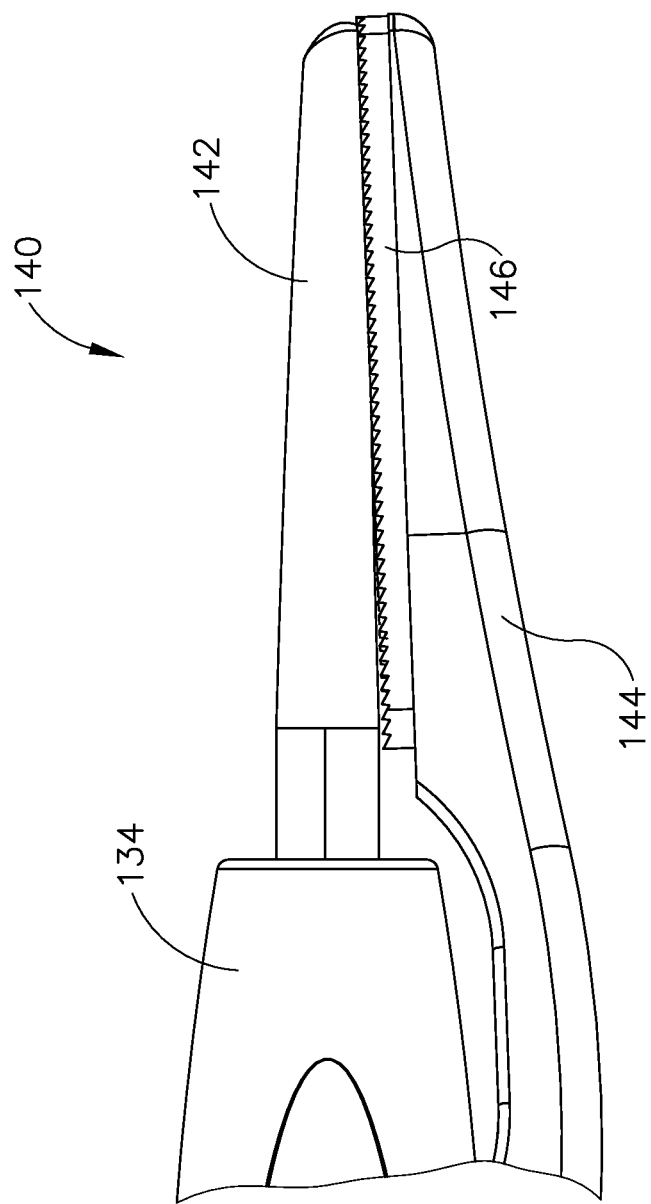
FIG. 5 depicts a side elevational view of the end effector of the instrument of FIG. 4, in a closed configuration.
Figure 6A:
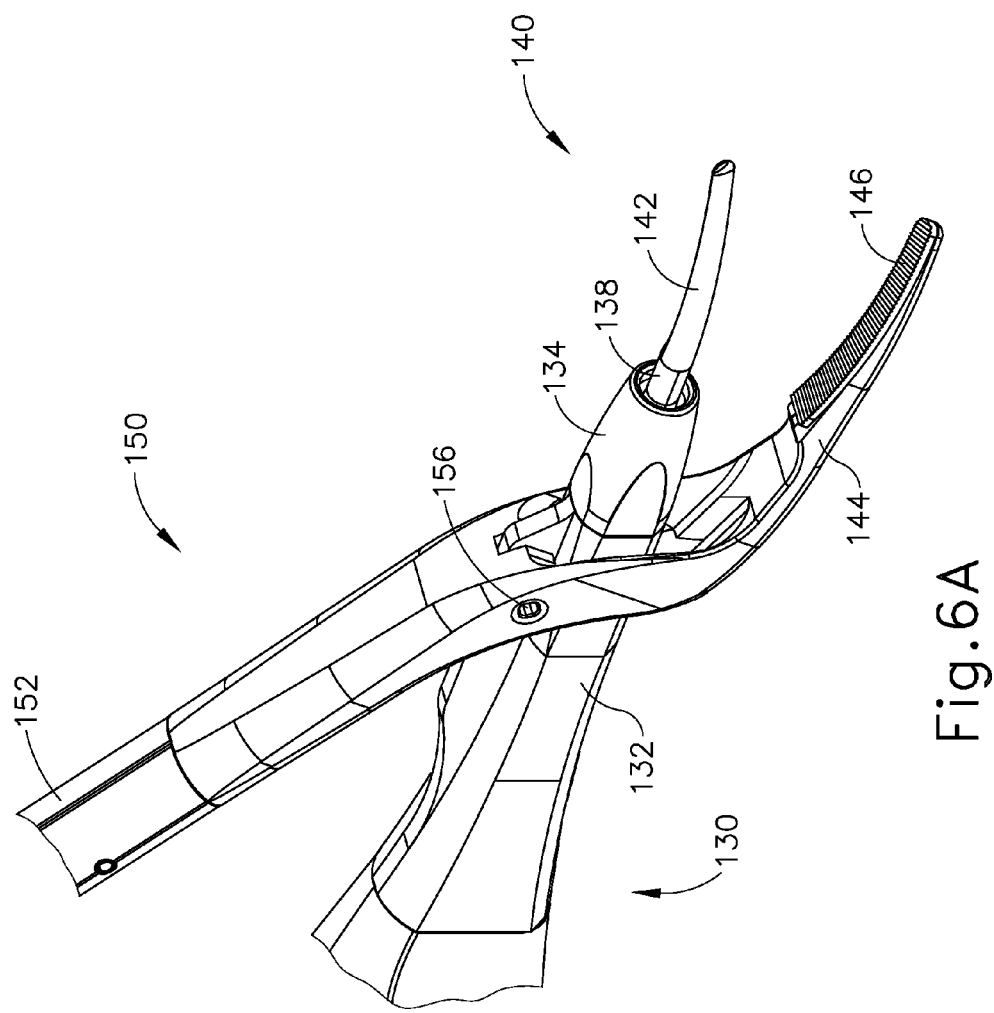
FIG. 6A depicts a perspective view of the end effector of FIG. 5, in an open configuration.
Figure 6B:
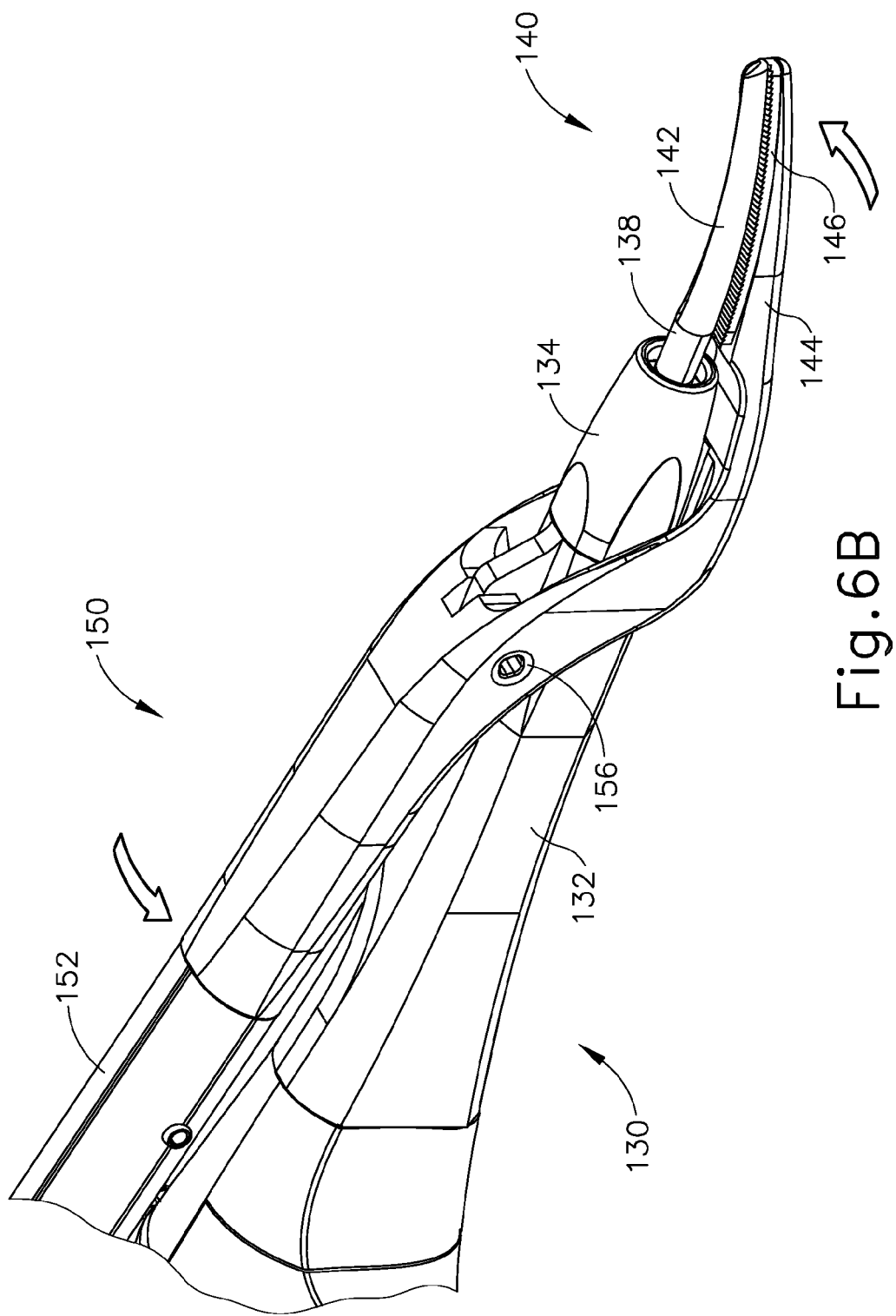
FIG. 6B depicts a perspective view of the end effector of FIG. 5, in a closed configuration.
Figure 7:
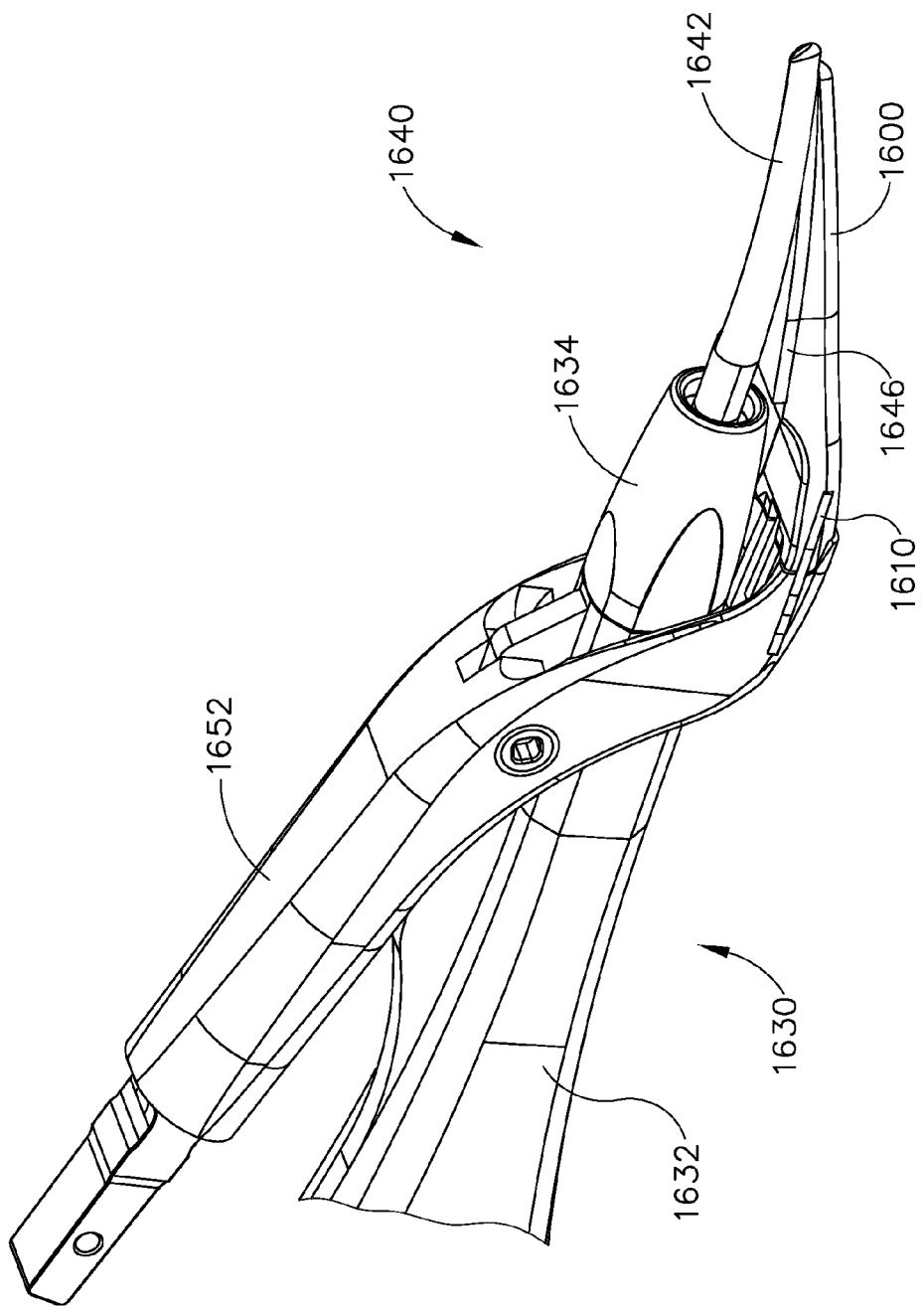
FIG. 7 depicts a perspective view of an exemplary alternative end effector, with a compliant segmented clamp arm assembly, in a closed position.

Shaft assembly (130) comprises an outer sheath (132) extending distally from body (122). A cap (134) is secured to the distal end of sheath (132). As best seen in FIGS. 5-6B, end effector (140) comprises an ultrasonic blade (142) and a clamp arm (144). Ultrasonic blade (142) extends distally from cap (134). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 6A-6B, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 6A. By way of example only, such a resilient member may comprise a leaf spring, a torsion spring, and/or any other suitable kind of resilient member.

Referring back to FIG. 4, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided—one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265; U.S. Pub. No. 2014/0005701, issued as U.S. Pat. No. 9,393,037 on Jul. 9, 2016; U.S. Pub. No. 2014/0114334, issued as U.S. Pat. No. 9,095,367 on Aug. 4, 2015; and/or U.S. patent application Ser. No. 14/031,665, published as U.S. Pat. Pub. No. 2015/0080925 on Mar. 19, 2015. Additional merely illustrative variations for instrument (100) will be described in greater detail below. It should be understood that the below described variations may be readily applied to instrument (100) described above and any of the instruments referred to in any of the references that are cited herein, among others.

II. Exemplary Features for Providing Heat Management in an Ultrasonic Surgical Instrument In some instances, one or more regions of instrument (10, 100) may heat up during extended operation of instrument (10, 100) in a surgical procedure. By way of example only, blade (42, 142), clamp arm (44, 144), and/or other portions of instrument (10, 100) may eventually heat up over time. Such heating may be caused by friction and/or other factors. To the extent that the heat is initially generated in one particular component of instrument (10, 100) (e.g., blade (42, 142) or clamp arm (44, 144), etc.), such heat may be gradually transmitted to other portions of instrument (10, 100). It may be desirable to minimize such heating and/or otherwise manage such heating in order to avoid having heated portions of instrument (10, 100) contact tissue that should not be heated. For instance, the operator may wish for end effector (40, 140) to be relatively cool when the operator wishes to use end effector (40, 140) to perform spreading blunt dissections and/or simple tissue grasping, etc. It may also be desirable to minimize heat and/or otherwise manage heat in a way that does not significantly increase the size or operability of instrument (10, 100). Several examples of how heating may be minimized and/or otherwise managed are described in greater detail below; while other examples will be apparent to those of ordinary skill in the art in view of the teachings herein.

In addition to the examples described below, it should be understood that one or more portions of instrument (10, 100) may include a thermal insulator or barrier coating (e.g., a thin coating of thermal insulator or barrier material with a very low thermal conductivity). An example of a thermal insulator or barrier coating is a nanocomposite (e.g., hydro-NM-oxide) in an acrylic resin suspension. An example of such a coating is NANSULATE® coating by Industrial Nanotech, Inc. of Naples, Fla. Additional merely illustrative examples of thermal insulator or barrier coatings include the following: EST 1711 by Ellison Surface Technologies, Inc. of Mason, Ohio; EST 1732 by Ellison Surface Technologies, Inc. of Mason, Ohio; EST 3030 by Ellison Surface Technologies, Inc. of Mason, Ohio; EST 1711+EST 3030 by Ellison Surface Technologies, Inc. of Mason, Ohio; Oxytech V by Techmetals, Inc. of Dayton, Ohio; Alumina Titania; Zirconium Oxide; Aluminum Oxide; and/or various other kinds of coatings, including combinations thereof.

A thermal insulator or barrier coating may be applied to various external surfaces of instrument (10, 100), such as regions of blade (42, 142) that are not intended to contact tissue, clamp arm (44, 144), clamp pad (46, 146), outer sheath (32, 132), cap (134), etc. In addition or in the alternative, such a coating may be applied to various internal surfaces of instrument (10, 100), such as surfaces in generator (16, 116), transducer assembly (12, 112), internal electronics components, etc. In addition to providing a thermal barrier or insulation, such a coating may serve as a corrosion barrier, fire block, etc. In the below examples that include various components that are added to or otherwise incorporated into variations of instrument (10, 100), the coating may also be applied to one or more regions of such components. Other suitable ways in which a thermal coating may be incorporated into instrument (10, 100) and variations thereof will be apparent to those of ordinary skill in the art in view of the teachings herein.

To the extent that any of the examples discussed below are shown and described in the context of a variation of one particular kind of instrument (10 or 100), it should be understood that the same teachings may be readily applied to the other kind of instrument (10 or 100). Each example described below should therefore not be viewed as only having applicability to either instrument (10) or instrument (100). Furthermore, it is contemplated that the teachings below may be readily applied to other kinds of instruments, not just variations of instruments (10, 100).

In some instances, the heating at an end effector (40, 140) may be caused or hastened by direct contact between clamp pad (46, 146) and blade (42, 142) while clamp arm (44, 144) is closed and blade (42, 142) is activated, etc. Such direct contact may occur at regions where tissue is not interposed between clamp pad (46, 146) and blade (42, 142). Some operators may position tissue just between the distal portion of clamp pad (46, 146) and the distal portion of blade (42, 142). This may occur when end effector (40, 140) is used to transect relatively small vessels. When this occurs, the distal portions of clamp pad (46, 146) and blade (42, 142) may both contact the tissue compressed between clamp pad (46, 146) and blade (42, 142); yet the proximal portions of clamp pad (46, 146) and blade (42, 142) may just directly contact each other. When blade (42, 142) is activated in such instances, clamp pad (46, 146) and blade (42, 142) may rapidly generate a significant amount of heat at the proximal portions where the direct contact occurs.

It may therefore be desirable to minimize the amount of direct contact between clamp pad (46, 146) and blade (42, 142), particularly at the proximal regions of clamp pad (46, 146) and blade (42, 142). In other words, it may be desirable to provide staged engagement between clamp pad (46, 146) and blade (42, 142), such that the distal regions of clamp pad (46, 146) and blade (42, 142) engage first; then the proximal regions of clamp pad (46, 146) and blade (42, 142). Various examples of how an end effector (40, 140) may provide such staged engagement will be described in greater detail below. Other examples will be apparent to those of ordinary skill in the art in view of the teachings herein. While the following examples include variations of clamp arms (44, 144) and/or clamp pads (46, 146) that provide staged engagement between clamp pad (46, 146) and blade (42, 142), it should be understood that blade (42, 142) may also be modified to have one or more features (e.g., a hump or other protrusion, etc.) that provide staged engagement between clamp pad (46, 146) and blade (42, 142). It should also be understood that, in versions where there is staged engagement between clamp pad (46, 146) and blade (42, 142), clamp pad (46, 146) may be provided in two or more segments. For instance, in versions where the distal region of clamp pad (46, 146) engages tissue first, followed by the proximal region of clamp pad (46, 146) engaging tissue, clamp pad (46, 146) may be provided in a distal segment and an adjacent proximal segment. The distal segment may be formed of material(s) providing greater durability and/or some other difference(s) in properties as compared to the material(s) forming the proximal segment. Other suitable ways in which a clamp pad (46, 146) may be provided in segments will be apparent to those of ordinary skill in the art in view of the teachings herein. Similarly, various kinds of different materials and/or other structural characteristics that may be used in different clamp pad segments will be apparent to those of ordinary skill in the art in view of the teachings herein.

A. Exemplary Segmented Clamp Arm

FIGS. 7-9C depict an exemplary alternative end effector (1640). End effector (1640) of this example is substantially similar to end effector (140) described above. In particular, end effector (1640) includes an ultrasonic blade (1642) and a pivoting clamp arm (1600) with clamp pad (1646). Shaft assembly (1630) is substantially similar to shaft assembly (130) described above. In particular, shaft assembly (1630) includes an outer sheath (1632) and a cap (1634). Clamp arm (1600) is coupled with a shank (1652) via a leaf spring (1610), the combination of which is pivotally coupled with outer sheath (1632) such that clamp arm (1600) pivots toward and away from blade (1642) in response to pivoting of shank (1652) relative to shaft assembly (1630).

Figure 8:
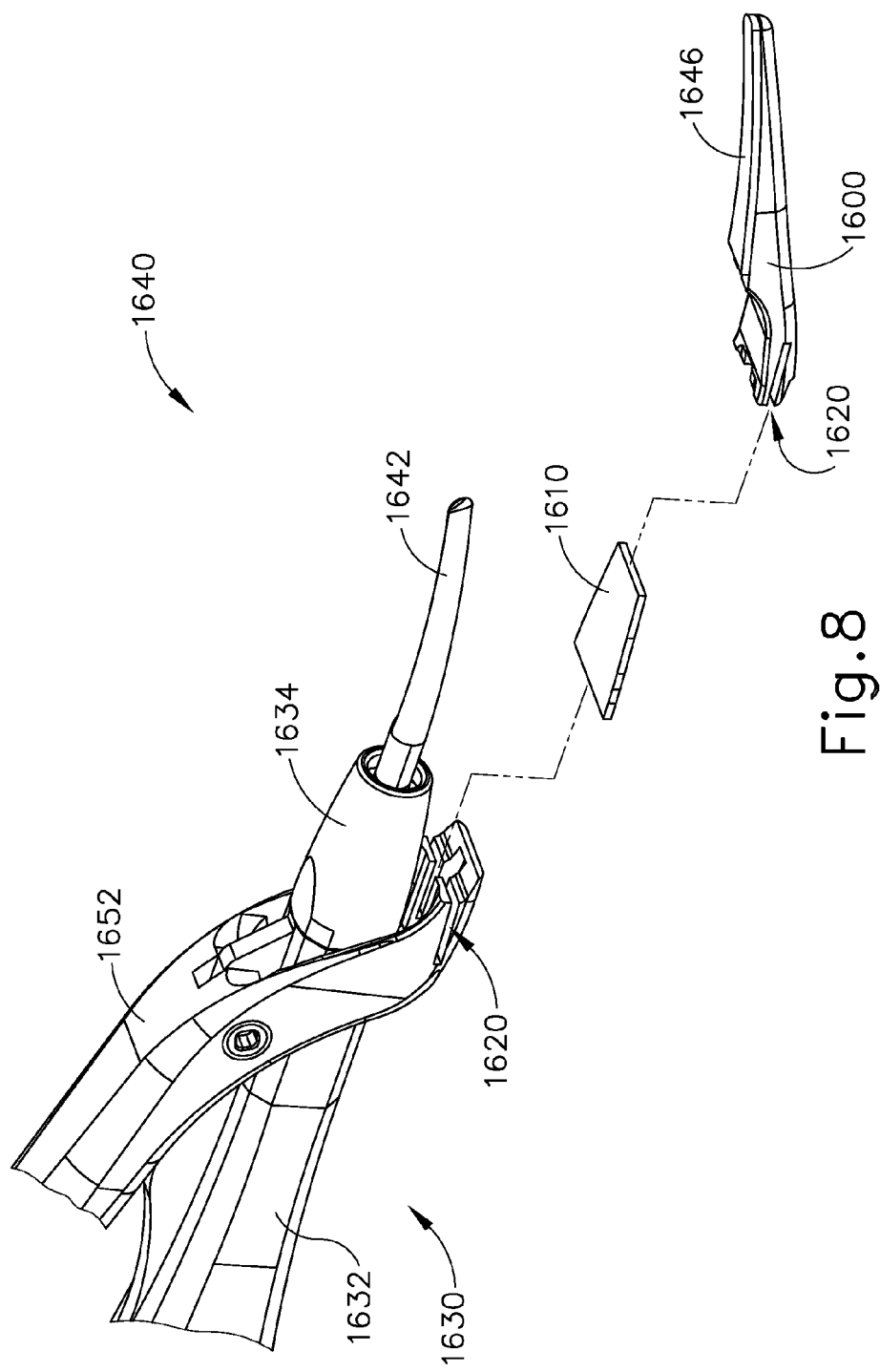
FIG. 8 depicts an exploded view of the clamp arm assembly of FIG. 7.
Figure 9A:
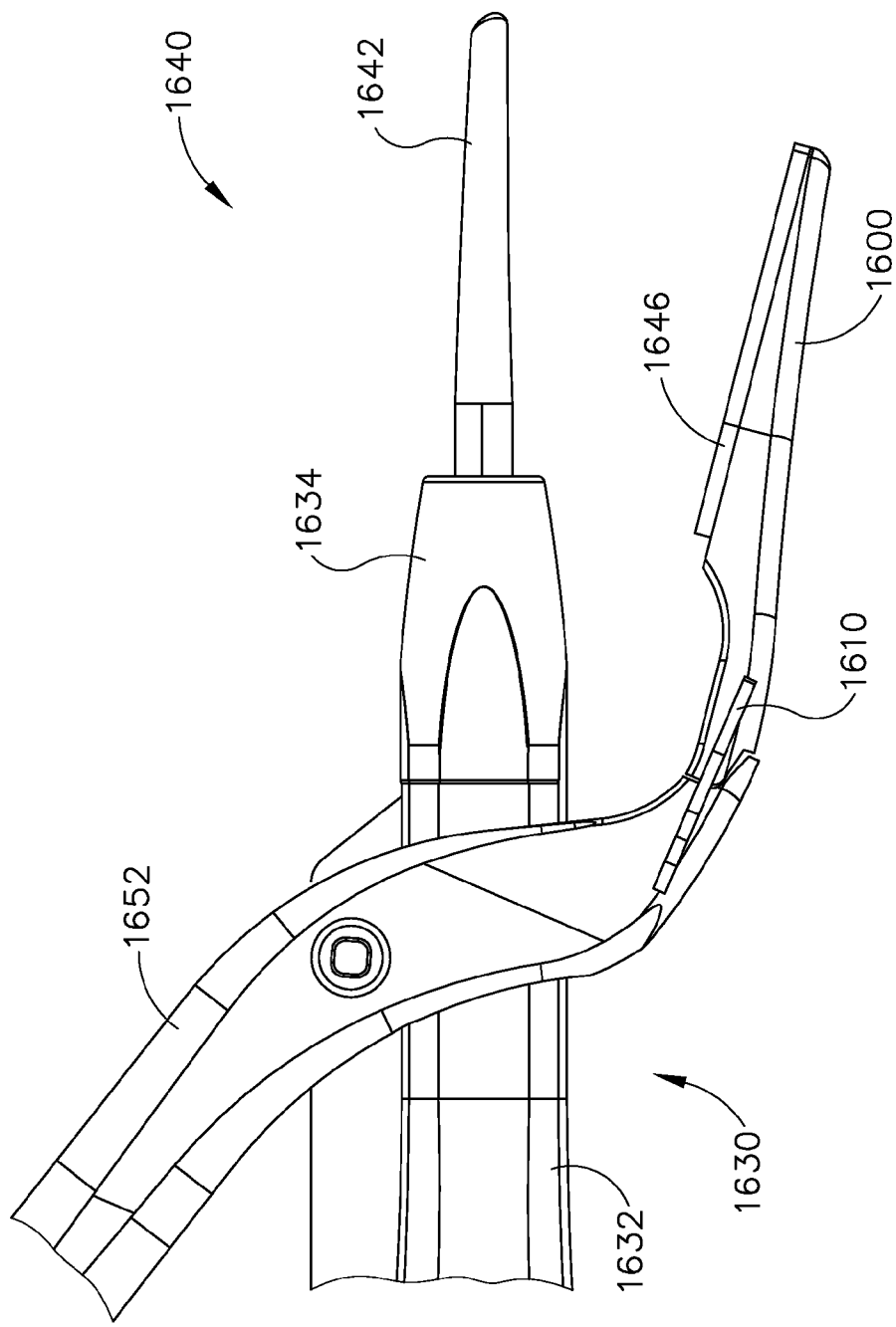
FIG. 9A depicts a side elevational view of the end effector of FIG. 7, with the clamp arm in an open position.

As best seen in FIG. 8, the distal end of shank (1652) presents a slot (1620). Similarly, the proximal end of clamp arm (1600) presents a slot (1602). Leaf spring (1610) is secured in slots (1602, 1620). By way of example only, leaf spring (1610) may be secured in slots (1602, 1620) using an interference fitting, adhesives, and/or any other suitable structures/techniques. Leaf spring (1610) is configured to provide a bias to clamp arm (1600). FIG. 9A shows clamp arm (1600) in an open position, such that clamp arm (1600) is spaced away from blade (1642). It should be understood that end effector (1640) may be maneuvered to position tissue between clamp pad (1646) and blade (1642) while clamp arm (1600) is in an open position as shown in FIG. 9A.

Figure 9B:
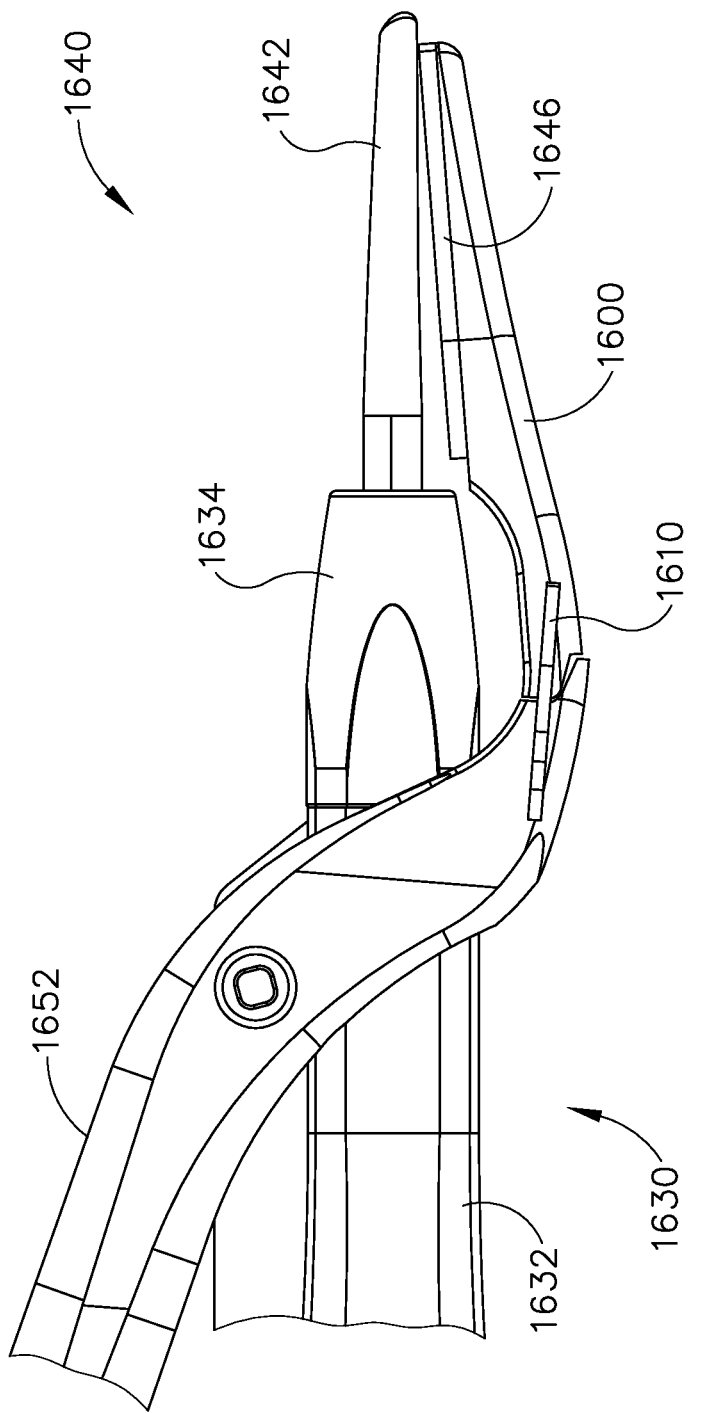
FIG. 9B depicts a side elevational view of the end effector of FIG. 7, with the clamp arm in a first closed position.
Figure 9C:
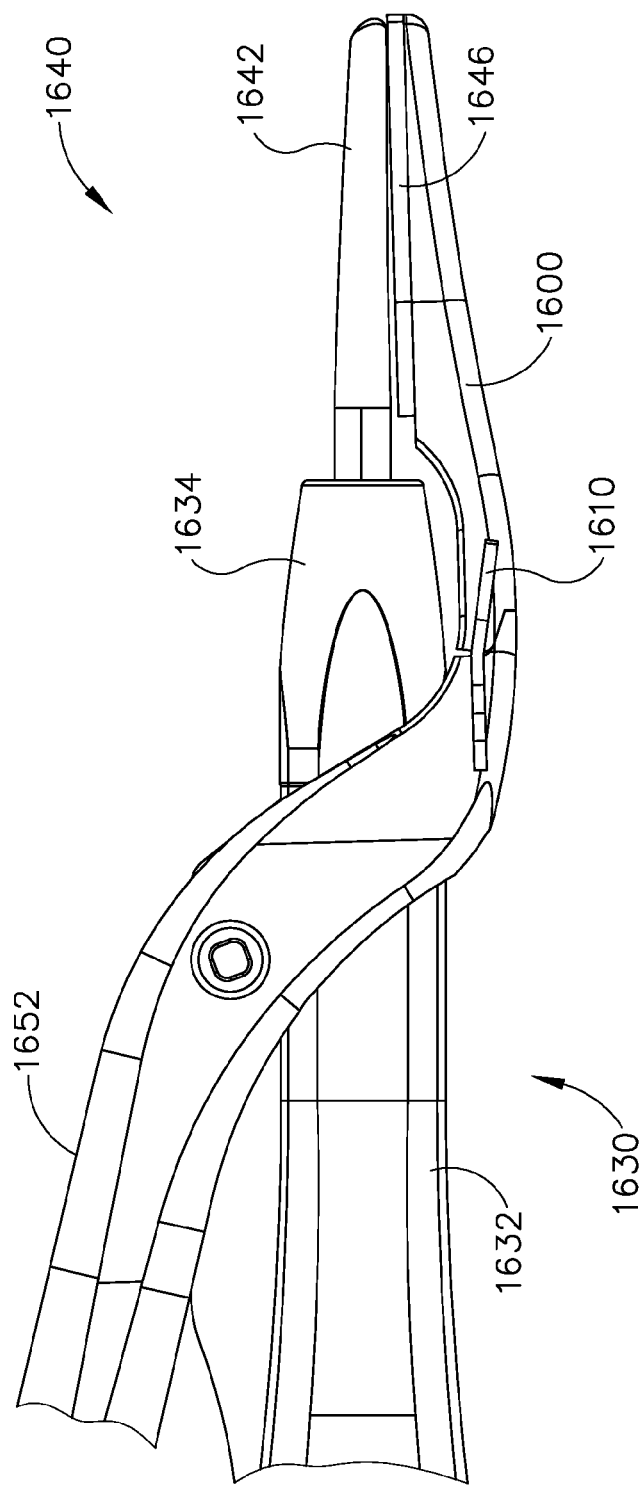
FIG. 9C depicts a side elevational view of the end effector of FIG. 7, with the clamp arm in a second closed position.
Figure 10:
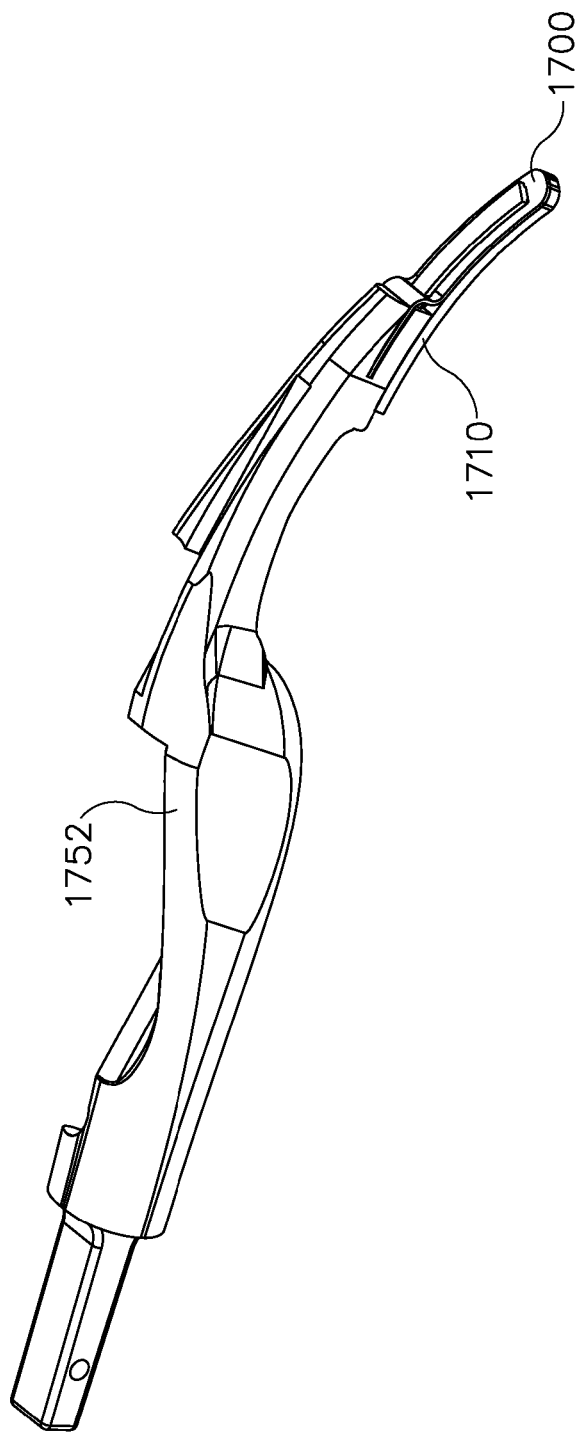
FIG. 10 depicts a perspective view of an exemplary alternative clamp arm assembly.

FIG. 9B shows clamp arm (1600) in a first closed position. In this position, the bias of leaf spring (1610) urges the distal end of clamp pad (1646) into contact with blade (1642) before the rest of clamp pad (1646) contacts blade (1642). In other words, clamp pad (1646) is oriented along a plane that is obliquely oriented relative to the opposing surface of blade (1642). As the operator continues to pivot shank (1652) toward shaft assembly (1630), leaf spring (1610) begins to deform, allowing clamp arm (1600) to pivot relative to shank (1652). This deformation of leaf spring (1610) continues to a point where the full length of clamp pad (1646) is in contact with blade (1642), as shown in FIG. 9C. In other words, clamp pad (1646) eventually reaches an orientation where clamp pad (1646) is oriented along a plane that is parallel to the opposing surface of blade (1642).

It should be understood from the foregoing that clamp pad (1646) and blade (1642) will compress tissue captured between the distal regions of clamp pad (1646) and blade (1642) before the proximal regions of clamp pad (1646) and blade (1642) come in contact with each other. To the extent that tissue is positioned between both the distal regions of clamp pad (1646) and blade (1642) and the proximal regions of clamp pad (1646) and blade (1642), the tissue at the distal region will be compressed/transected/sealed first; followed by the tissue at the proximal region. It should also be understood that leaf spring (1610) may provide sufficient stiffness to allow a sufficient amount of compression during the first stage of clamp arm (1600) closure. In other words, leaf spring (1610) may allow clamp arm (1600) to apply enough compression on tissue to enable end effector (1640) to successfully compress/transect/seal tissue that is captured between the distal regions of clamp pad (1646) and blade (1642), before leaf spring (1610) begins to significantly deform as shown in FIG. 9C. A suitable spring constant for leaf spring (1610) will be apparent to those of ordinary skill in the art in view of the teachings herein.

It should also be understood that the distal end of shank (1652) and the proximal end of clamp arm (1600) may include cooperating hard stop features that restrict the amount of deformation of leaf spring (1610) after end effector (1640) reaches the second stage of closure shown in FIG. 9C. Such features may prevent the joint between shank (1652) and clamp arm (1600) from becoming hyperextended. Such features may also enable the operator to apply a significant amount of clamping force to tissue captured between clamp pad (1646) and blade (1642) after end effector (1640) reaches the second stage of closure. In other words, the clamping force at this stage may not be affected by the resilience of leaf spring (1610), such that the combination of shank (1652) and clamp arm (1600) may behave as if they were a unitary, monolithic structure. Various suitable configurations for hard stop features will be apparent to those of ordinary skill in the art in view of the teachings herein. Similarly, other suitable variations of end effector (1640) will be apparent to those of ordinary skill in the art in view of the teachings herein.

B. Exemplary Clamp Arm with Resilient Base and Flexible Clamp Pad

FIGS. 10-15B depict another exemplary shank (1752), clamp arm (1700), and clamp pad (1710) that may be readily incorporated into an end effector such as effector (140) described above. The proximal end of clamp arm (1700) is inserted into a slot (1702) formed at the distal end of shank (1752). The proximal end of clamp arm (1700) may be secured in slot (1702) using an interference fitting, adhesives, and/or any other suitable structures/techniques. In instances where shank (152) and clamp arm (144) are substituted with shank (1752) and clamp arm (1700), the combination of clamp arm (1700) and shank (1752) is pivotally coupled with outer sheath (132) such that clamp arm (1700) pivots toward and away from blade (142) in response to pivoting of shank (1752) relative to shaft assembly (130).

Figure 11:
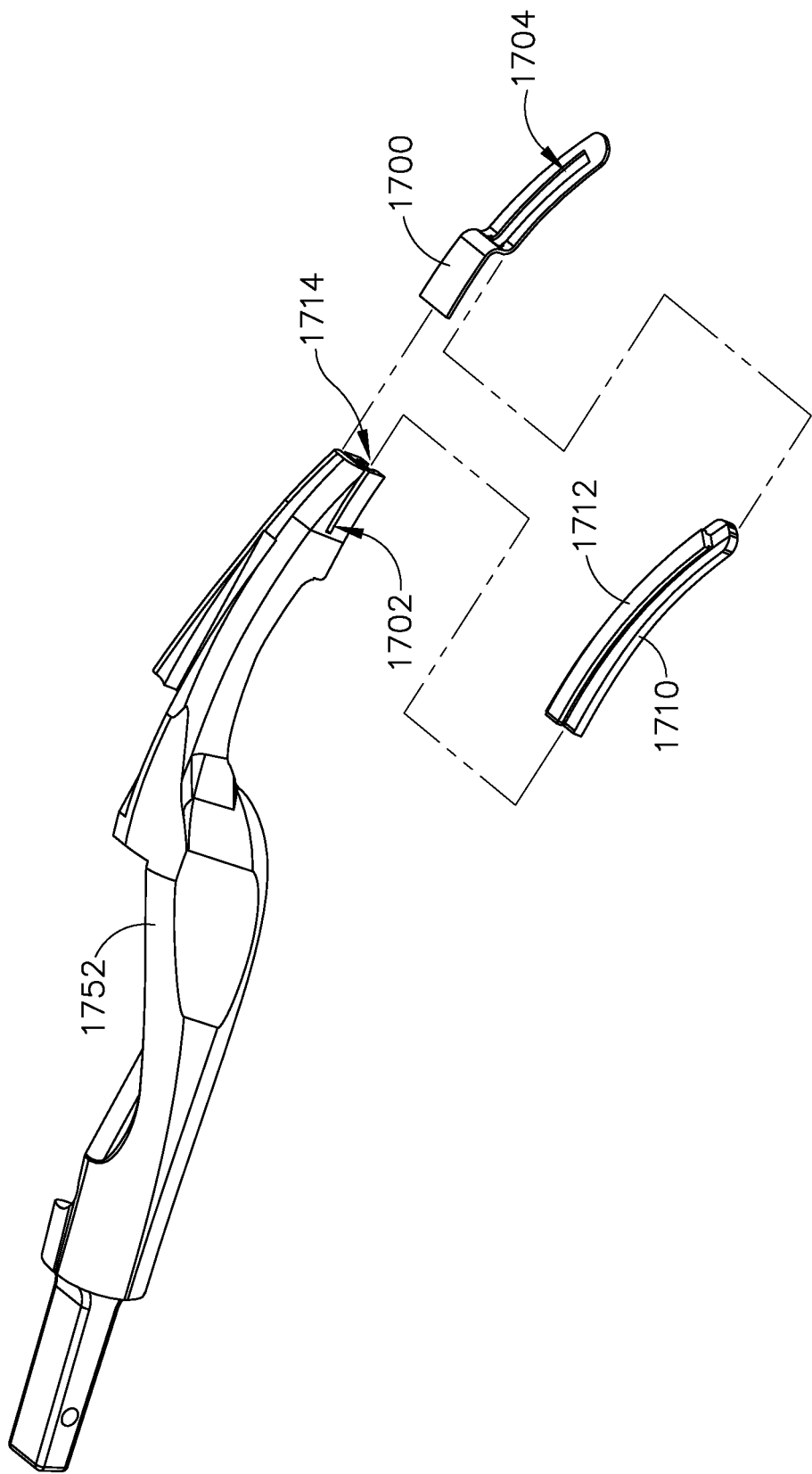
FIG. 11 depicts an exploded view of the clamp arm assembly of FIG. 10.
Figure 12:
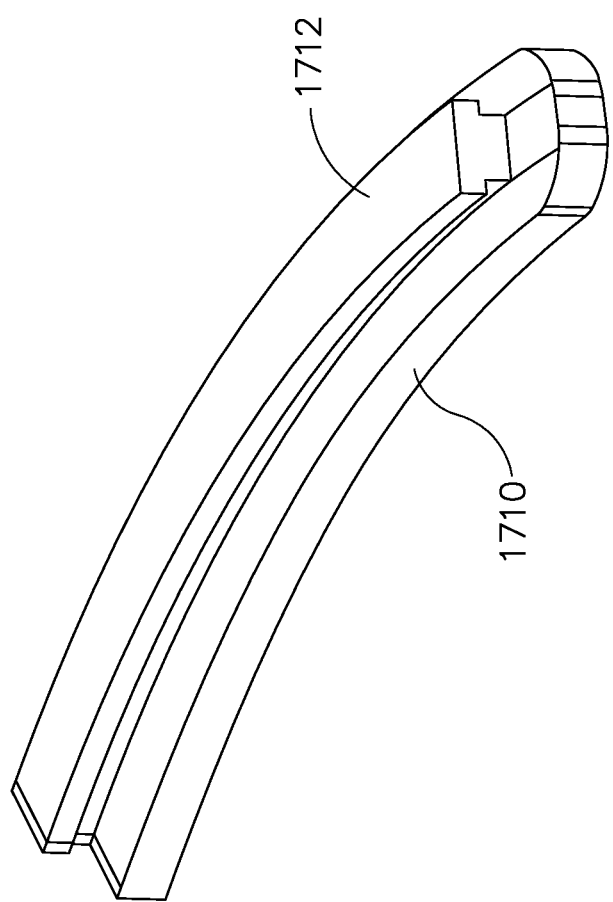
FIG. 12 depicts a perspective view the clamp pad of the clamp arm assembly of FIG. 10.
Figure 13:
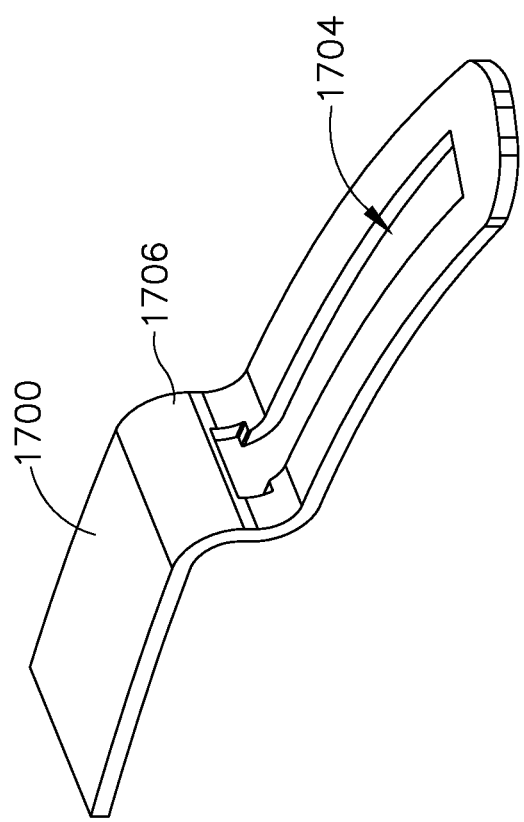
FIG. 13 depicts a perspective view of the resilient member of the clamp arm assembly of FIG. 10.
Figure 14:
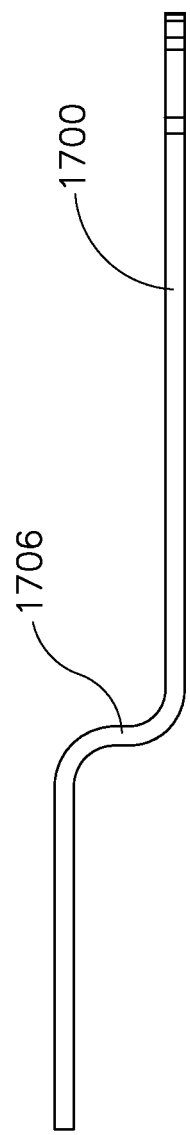
FIG. 14 depicts a side elevational view of the resilient member of FIG. 13.

Clamp pad (1710) of the present example is flexible, such that clamp pad (1710) is configured to transition from a curved configuration to a flat configuration. As best seen in FIGS. 11-12, clamp pad (1710) includes a rail (1712) that is configured to fit within a channel (1714) formed in shank (1752) and within a slot (1704) formed in clamp arm (1700). Clamp pad (1710) is thus separately secured to both shank (1752) and clamp arm (1700). As best seen in FIGS. 13-14, clamp arm (1700) has a dogleg configuration, such that the distal portion of clamp arm (1700) is offset from the proximal portion of clamp arm (1700). This dogleg configuration is characterized by a transition region (1706) that provides the offset. In the present example, the transition region (1706) is positioned closer to the proximal end of clamp arm (1700) than the distal end of clamp arm (1700). In some other versions, the transition region (1706) is positioned at the middle of clamp arm (1700). In still other versions, the transition region (1706) is positioned closer to the distal end of clamp arm (1700) than the proximal end of clamp arm (1700). While the distal portion of clamp arm (1700) is parallel to the proximal portion of clamp arm (1700) in this example, any other suitable orientations may be used. Other suitable configurations and relationships will be apparent to those of ordinary skill in the art in view of the teachings herein.

Figure 15A:
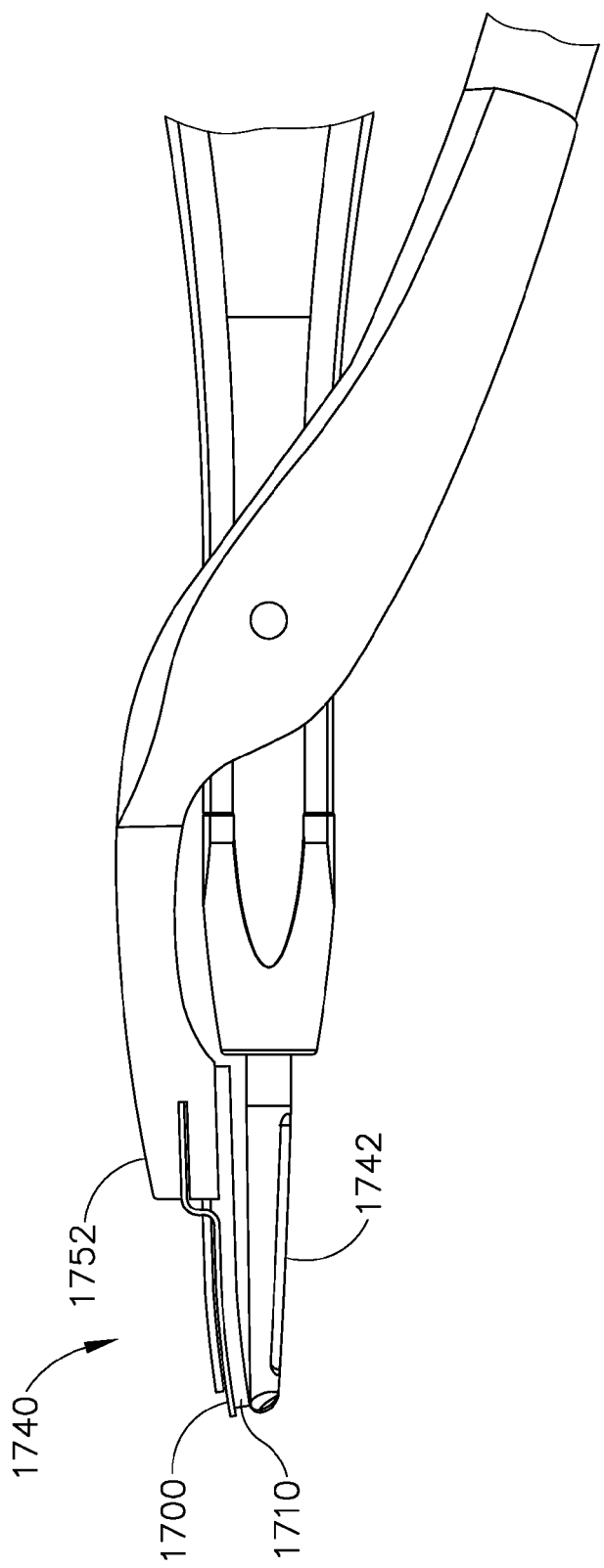
FIG. 15A depicts a side elevational view of the clamp arm assembly of FIG. 10 in a first closed position in relation to an ultrasonic blade.
Figure 15B:
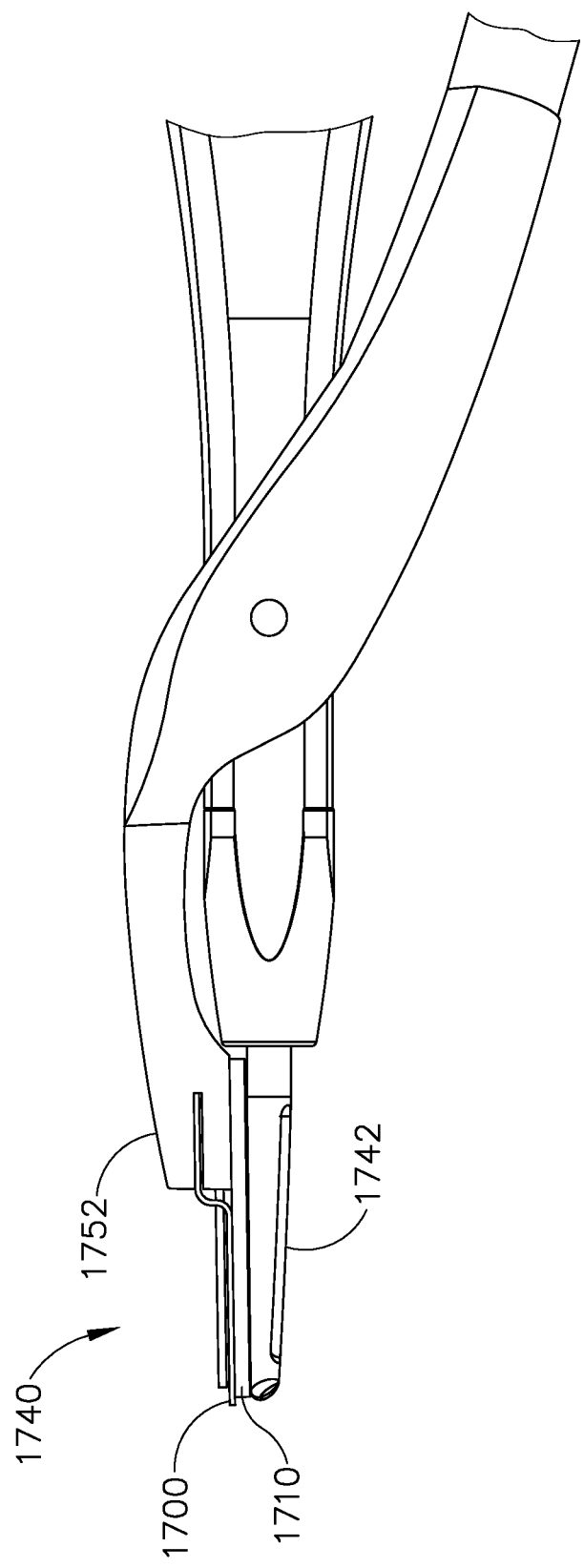
FIG. 15B depicts a side elevational view of the clamp arm assembly of FIG. 10 in a second closed position in relation to an ultrasonic blade.
Figure 16:
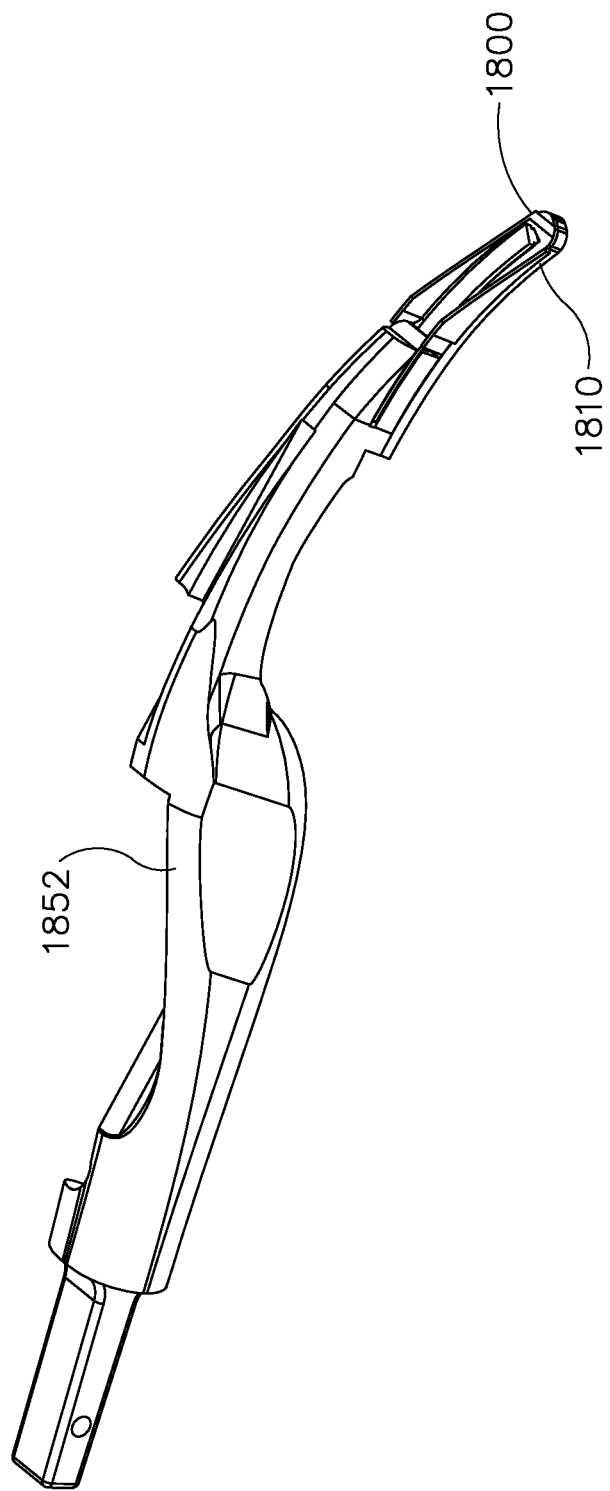
FIG. 16 depicts a perspective view of another exemplary alternative clamp arm assembly.
Figure 17:
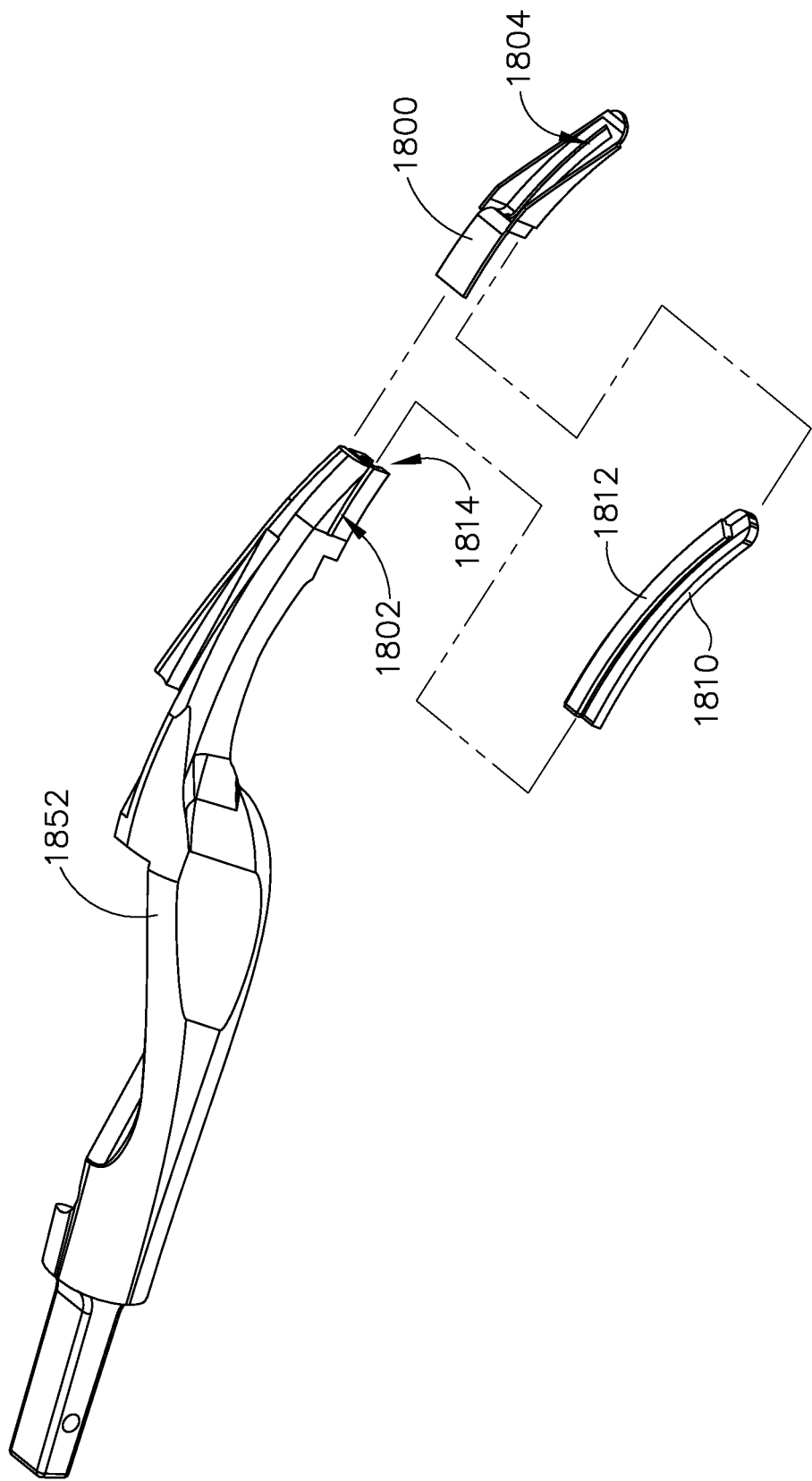
FIG. 17 depicts an exploded view of the clamp arm assembly of FIG. 16.
Figure 18:
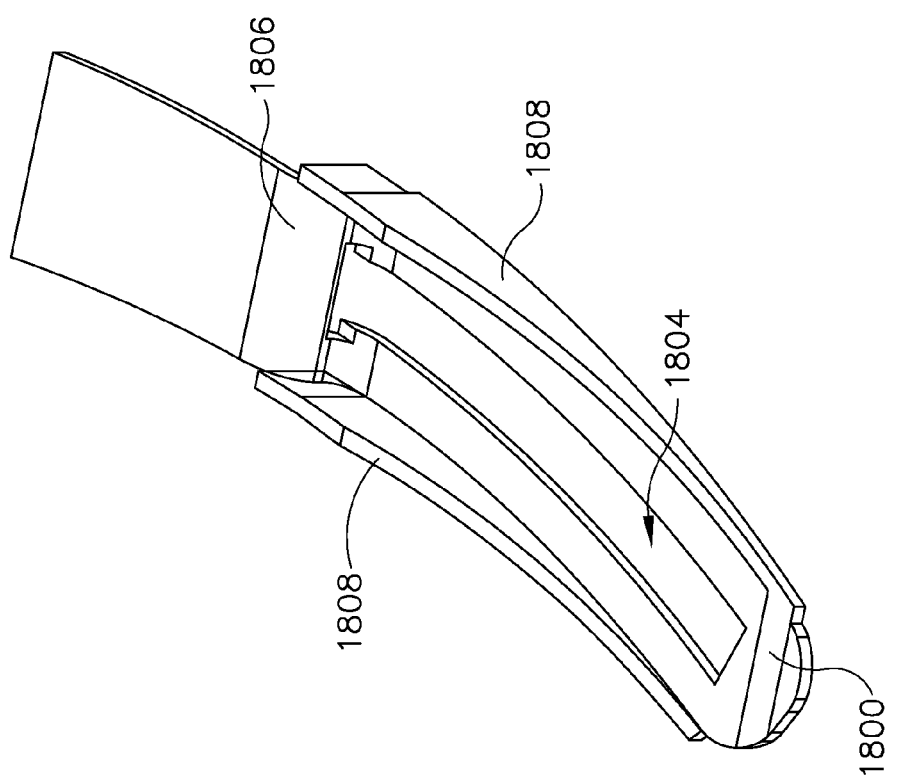
FIG. 18 depicts a perspective view of the resilient member of the clamp arm assembly of FIG. 16.
Figure 19:
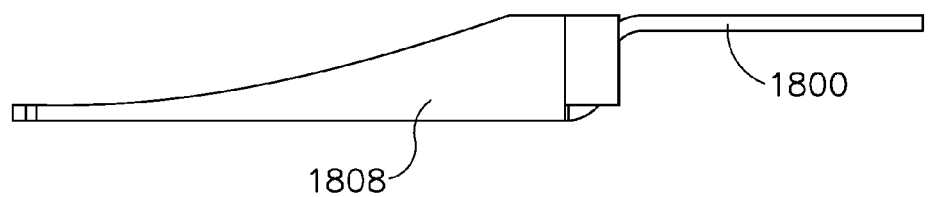
FIG. 19 depicts a side elevational view of the resilient member of FIG. 18.

Clamp arm (1700) of the present example is resilient, such that clamp arm (1700) is configured to provide a bias to clamp pad (1710), similar to the bias provided by leaf spring (1610) described above. In particular, FIG. 15A shows clamp arm (1700) in a first closed position. In this position, the bias of clamp arm (1700) urges the distal end of clamp pad (1710) into contact with blade (1742) before the rest of clamp pad (1710) contacts blade (1742). In other words, clamp pad (1710) is non-parallel with the opposing surface of blade (1742) at this stage. It should be understood that the orientation of slot (1702) may influence the configuration and orientation of clamp arm (1700) and clamp pad (1710), particularly before and during the range of travel to the first closed position. Clamp pad (1710) may define a curved configuration at this stage. As the operator continues to pivot shank (1752), clamp arm (1700) begins to deform. This deformation of clamp arm (1700) continues to a point where the full length of clamp pad (1710) is in contact with blade (1742), as shown in FIG. 15B. In other words, clamp pad (1710) eventually reaches an orientation where clamp pad (1710) is oriented along a plane that is parallel to the opposing surface of blade (1742). Blade (1742) in this example is substantially similar to blade (142) described above.

It should be understood from the foregoing that clamp pad (1710) and blade (1742) will compress tissue captured between the distal regions of clamp pad (1710) and blade (1742) before the proximal regions of clamp pad (1710) and blade (1742) come in contact with each other. To the extent that tissue is positioned between both the distal regions of clamp pad (1710) and blade (1742) and the proximal regions of clamp pad (1710) and blade (1742), the tissue at the distal region will be compressed/transected/sealed first; followed by the tissue at the proximal region. It should also be understood that clamp arm (1700) may provide sufficient stiffness to allow a sufficient amount of compression during the first stage of clamp arm (1700) closure. In other words, clamp arm (1700) may apply enough compression on tissue to enable the end effector (1740) to successfully compress/transect/seal tissue that is captured between the distal regions of clamp pad (1710) and blade (1742), before clamp arm (1700) begins to significantly deform as shown in FIG. 15B. A suitable spring constant for clamp arm (1700) will be apparent to those of ordinary skill in the art in view of the teachings herein.

C. Exemplary Clamp Arm with Resilient Base and Flexible Clamp Pad and Hard Stop

FIGS. 16-20 depict another exemplary shank (1852), clamp arm (1800), and clamp pad (1810) that may be readily incorporated into an end effector such as effector (140) described above. The proximal end of clamp arm (1800) is inserted into a slot (1802) formed at the distal end of shank (1852). The proximal end of clamp arm (1800) may be secured in slot (1802) using an interference fitting, adhesives, and/or any other suitable structures/techniques. In instances where shank (152) and clamp arm (144) are substituted with shank (1852) and clamp arm (1800), the combination of clamp arm (1800) and shank (1852) is pivotally coupled with outer sheath (132) such that clamp arm (1800) pivots toward and away from blade (142) in response to pivoting of shank (1852) relative to shaft assembly (130).

Figure 20:
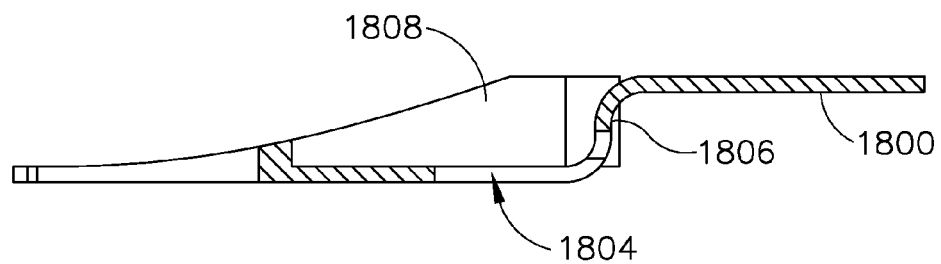
FIG. 20 depicts a cross-sectional side view of the resilient member of FIG. 19.

Clamp pad (1810) of the present example is flexible, such that clamp pad (1810) is configured to transition from a curved configuration to a flat configuration. Similar to clamp pad (1710) described above, clamp pad (1810) of this example includes a rail (1812) that is configured to fit within a channel (1814) formed in shank (1852) and within a slot (1804) formed in clamp arm (1800). Clamp pad (1810) is thus separately secured to both shank (1852) and clamp arm (1800). As best seen in FIG. 20, clamp arm (1800) has a dogleg configuration, such that the distal portion of clamp arm (1800) is offset from the proximal portion of clamp arm (1800). This dogleg configuration is characterized by a transition region (1806) that provides the offset. In the present example, the transition region (1806) is positioned closer to the proximal end of clamp arm (1800) than the distal end of clamp arm (1800). In some other versions, the transition region (1806) is positioned at the middle of clamp arm (1800). In still other versions, the transition region (1806) is positioned closer to the distal end of clamp arm (1800) than the proximal end of clamp arm (1800). While the distal portion of clamp arm (1800) is parallel to the proximal portion of clamp arm (1800) in this example, any other suitable orientations may be used. Other suitable configurations and relationships will be apparent to those of ordinary skill in the art in view of the teachings herein.

Clamp arm (1800) of the present example is resilient, such that clamp arm (1800) is configured to provide a bias to clamp pad (1810), similar to the bias provided by clamp arm (1700) described above. Thus, when clamp arm (1800) is in a first closed position, the bias of clamp arm (1800) urges the distal end of clamp pad (1810) into contact with a blade before the rest of clamp pad (1810) contacts the blade. In other words, clamp pad (1810) is non-parallel with the opposing surface of the blade at this stage. It should be understood that the orientation of slot (1802) may influence the configuration and orientation of clamp arm (1000) and clamp pad (1810), particularly before and during the range of travel to the first closed position. Clamp pad (1810) may define a curved configuration at this stage. As the operator continues to pivot shank (1852), clamp arm (1800) begins to deform. This deformation of clamp arm (1800) continues to a point where the full length of clamp pad (1810) is in contact with the blade. In other words, clamp pad (1810) eventually reaches an orientation where clamp pad (1810) is oriented along a plane that is parallel to the opposing surface of the blade.

It should be understood from the foregoing that clamp pad (1810) and the blade will compress tissue captured between the distal regions of clamp pad (1810) and the blade before the proximal regions of clamp pad (1810) and the blade come in contact with each other. To the extent that tissue is positioned between both the distal regions of clamp pad (1810) and the blade and the proximal regions of clamp pad (1810) and blade, the tissue at the distal region will be compressed/transected/sealed first; followed by the tissue at the proximal region. It should also be understood that clamp arm (1800) may provide sufficient stiffness to allow a sufficient amount of compression during the first stage of clamp arm (1800) closure. In other words, clamp arm (1800) may apply enough compression on tissue to enable the end effector to successfully compress/transect/seal tissue that is captured between the distal regions of clamp pad (1810) and the blade, before clamp arm (1800) begins to significantly deform in the second stage of closure. A suitable spring constant for clamp arm (1800) will be apparent to those of ordinary skill in the art in view of the teachings herein.

Clamp arm (1800) of the present example further includes a pair of vanes (1808) that are configured to engage the distal end of shank (1852) after clamp arm (1800) reaches the second stage of closure (where clamp pad (1810) is oriented along a plane that is parallel to the opposing surface of the blade). This engagement provides a hard stop that prevents the joint between shank (1852) and clamp arm (1800) from becoming hyperextended. Such features may also enable the operator to apply a significant amount of clamping force to tissue captured between clamp pad (1810) and a blade after the end effector reaches the second stage of closure. In other words, the clamping force at this stage may not be affected by the resilience of clamp arm (1800), such that the combination of shank (1852) and clamp arm (1800) may behave as if they were a unitary, monolithic structure. Various suitable configurations for hard stop features will be apparent to those of ordinary skill in the art in view of the teachings herein.

D. Exemplary Clamp Arm with Flex Mount Feature

Figure 21A:
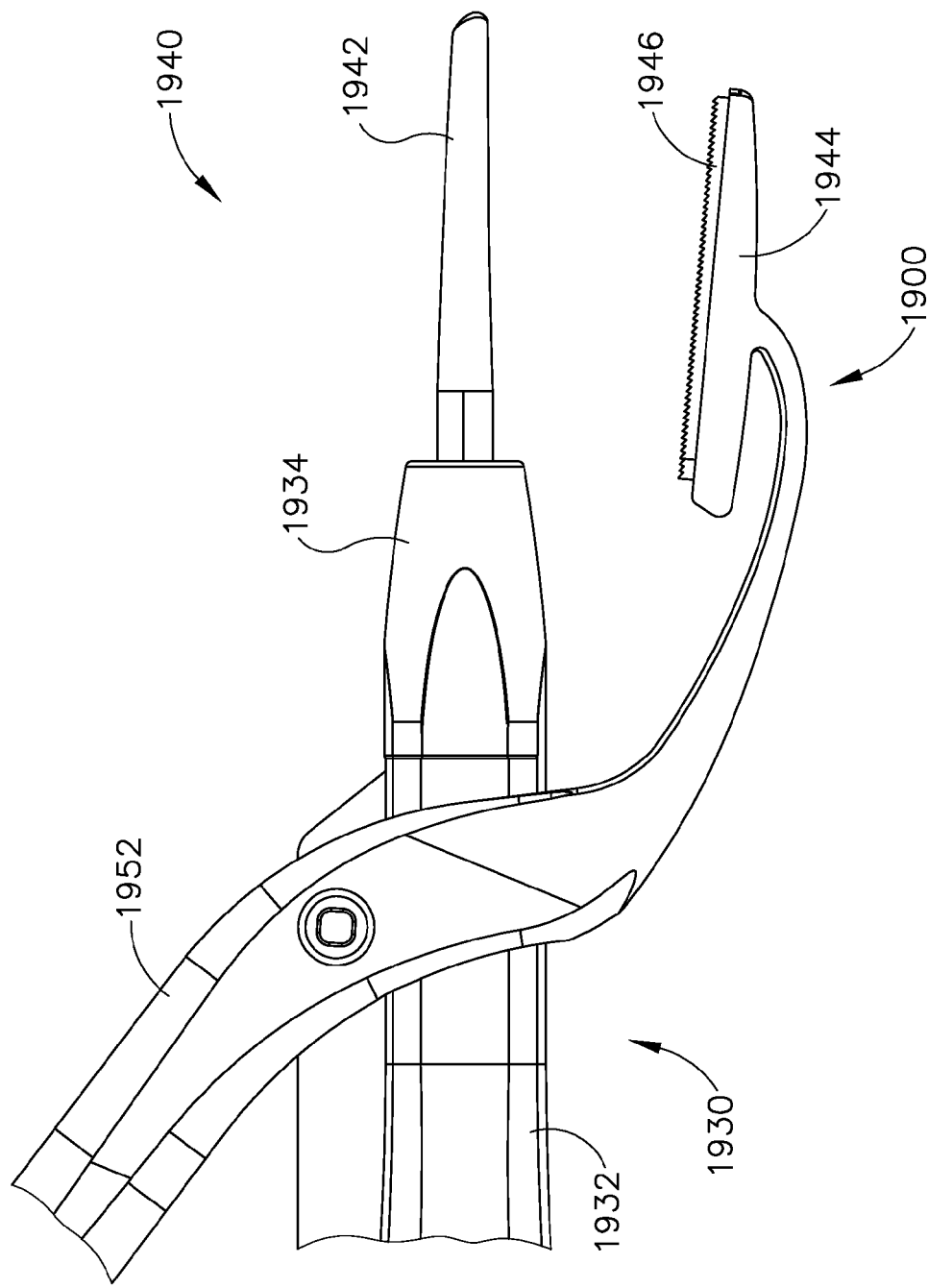
FIG. 21A depicts a side elevational view of another exemplary alternative end effector, with a clamp arm in an open position.
Figure 21B:
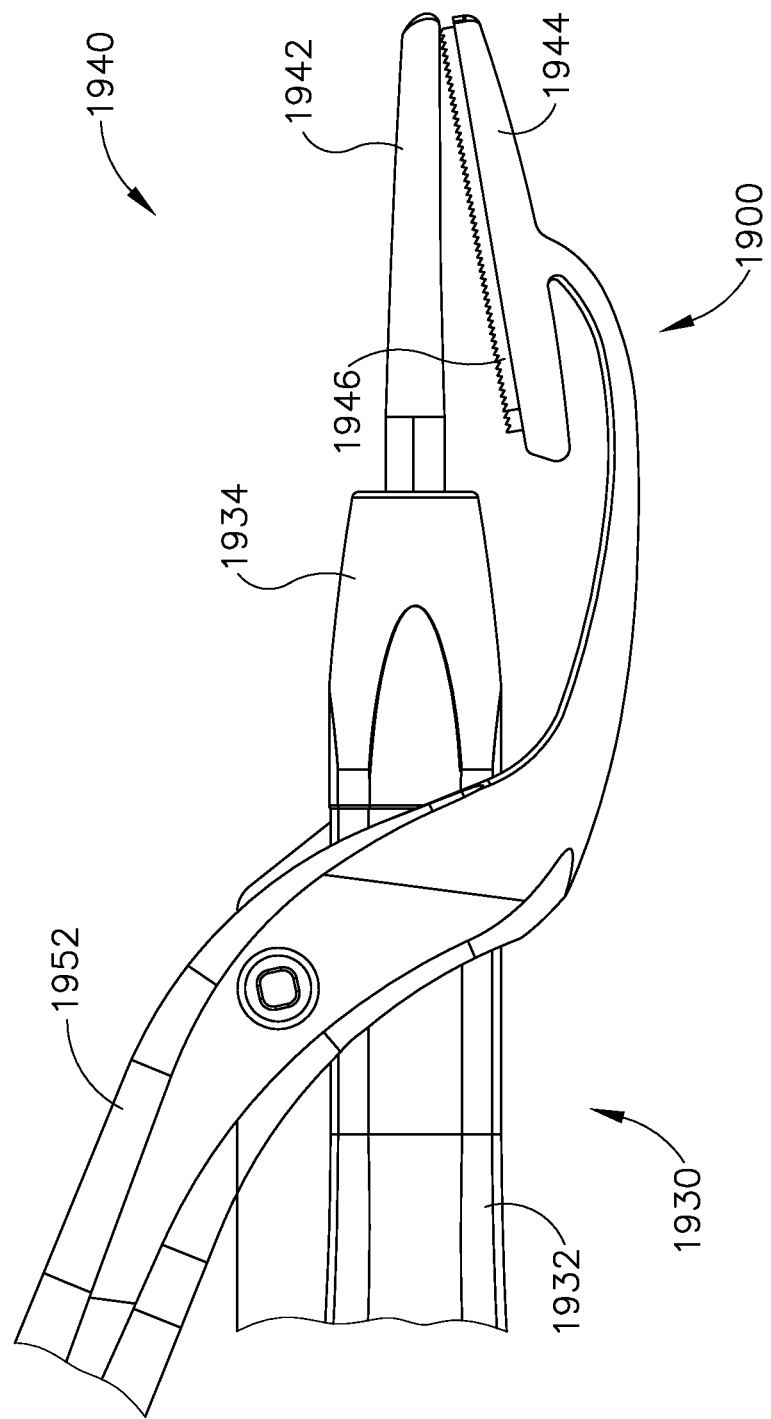
FIG. 21B depicts a side elevational view of the end effector of FIG. 21A, with the clamp arm in a first closed position.
Figure 21C:
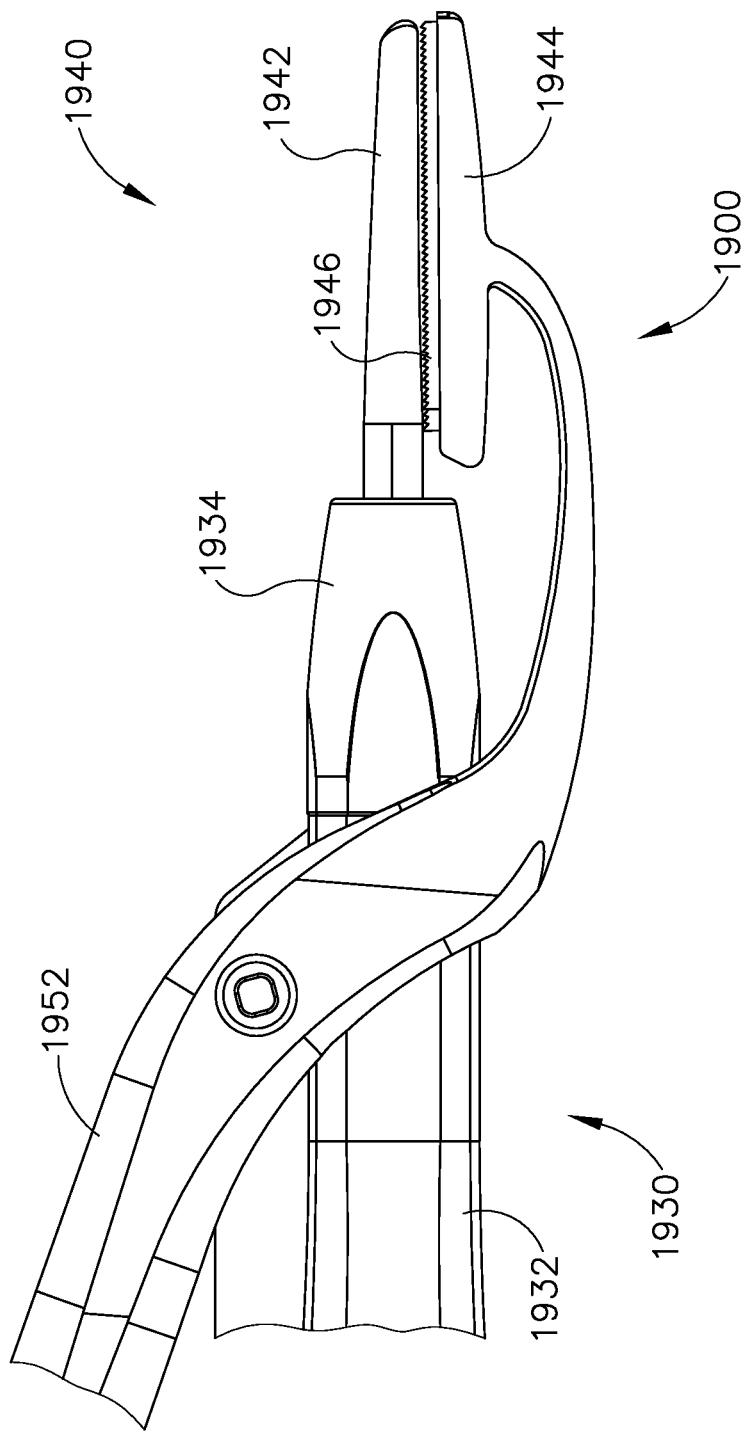
FIG. 21C depicts a side elevational view of the end effector of FIG. 21A, with the clamp arm in a second closed position.

FIGS. 21A-21C show another exemplary alternative end effector (1940). End effector (1940) of this example is substantially similar to end effector (140) described above. In particular, end effector (1940) includes an ultrasonic blade (1942) and a pivoting clamp arm (1900) with clamp pad (1946). Shaft assembly (1930) is substantially similar to shaft assembly (130) described above. In particular, shaft assembly (1930) includes an outer sheath (1932) and a cap (1934). Clamp arm (1944) is coupled with a shank (1952) via a flexible section (1900), the combination of which is pivotally coupled with outer sheath (1932) such that clamp arm (1944) pivots toward and away from blade (1942) in response to pivoting of shank (1952) relative to shaft assembly (1930). In the present example, clamp arm (1944), shank (1952), and flexible section (1900) together form a unitary, monolithic structure. In some other versions, clamp arm (1944), shank (1952), and flexible section (1900) are initially separate components that are joined together after they are formed. For instance, clamp arm (1944) and shank (1952) may be separately formed; with flexible section (1900) being formed by a pin that pivotally couples clamp arm (1944) and shank (1952) together. A torsion spring may be used to provide a pivotal bias.

Flexible section (1900) is resilient in this example, such that flexible section (1900) is configured to provide a bias to clamp arm (1944). FIG. 21A shows clamp arm (1944) in an open position, such that clamp arm (1944) is spaced away from blade (1942). It should be understood that end effector (1940) may be maneuvered to position tissue between clamp pad (1946) and blade (1942) while clamp arm (1944) is in an open position as shown in FIG. 21A.

FIG. 21B shows clamp arm (1944) in a first closed position. In this position, the bias of flexible section (1900) urges the distal end of clamp pad (1946) into contact with blade (1942) before the rest of clamp pad (1946) contacts blade (1942). In other words, clamp pad (1946) is oriented along a plane that is obliquely oriented relative to the opposing surface of blade (1942). As the operator continues to pivot shank (1952) toward shaft assembly (1930), flexible section (1900) begins to deform, allowing clamp arm (1944) to pivot relative to shank (1952). This deformation of flexible section (1900) continues to a point where the full length of clamp pad (1946) is in contact with blade (1942), as shown in FIG. 21C. In other words, clamp pad (1946) eventually reaches an orientation where clamp pad (1946) is oriented along a plane that is parallel to the opposing surface of blade (1942).

It should be understood from the foregoing that clamp pad (1946) and blade (1942) will compress tissue captured between the distal regions of clamp pad (1946) and blade (1942) before the proximal regions of clamp pad (1946) and blade (1942) come in contact with each other. To the extent that tissue is positioned between both the distal regions of clamp pad (1946) and blade (1942) and the proximal regions of clamp pad (1946) and blade (1942), the tissue at the distal region will be compressed/transected/sealed first; followed by the tissue at the proximal region. It should also be understood that flexible section (1900) may provide sufficient stiffness to allow a sufficient amount of compression during the first stage of clamp arm (1944) closure. In other words, flexible section (1900) may allow clamp arm (1944) to apply enough compression on tissue to enable end effector (1940) to successfully compress/transect/seal tissue that is captured between the distal regions of clamp pad (1946) and blade (1942), before flexible section (1900) begins to significantly deform as shown in FIG. 21C. A suitable spring constant for flexible section (1900) will be apparent to those of ordinary skill in the art in view of the teachings herein.

It should also be understood that the orientation and relationship between flexible section (1900) and clamp arm (1944) may provide an effective hard stop that prevents flexible section (1900) from flexing any further once end effector (1940) reaches the second stage of closure. For instance, the positioning of flexible section (1900) on the underside of clamp arm (1944) may provide an effective hard stop once end effector (1940) reaches the second stage of closure. It may also promote the functioning as a hard stop if flexible section (1900) is substantially longitudinally centered along the underside of clamp arm (1944). The functioning as an effective hard stop may enable the operator to apply a significant amount of clamping force to tissue captured between clamp pad (1946) and blade (1942) after end effector (1940) reaches the second stage of closure. Other suitable variations of end effector (1940) will be apparent to those of ordinary skill in the art in view of the teachings herein.

E. Exemplary Clamp Arm with Integral Flex Section

Figure 22:
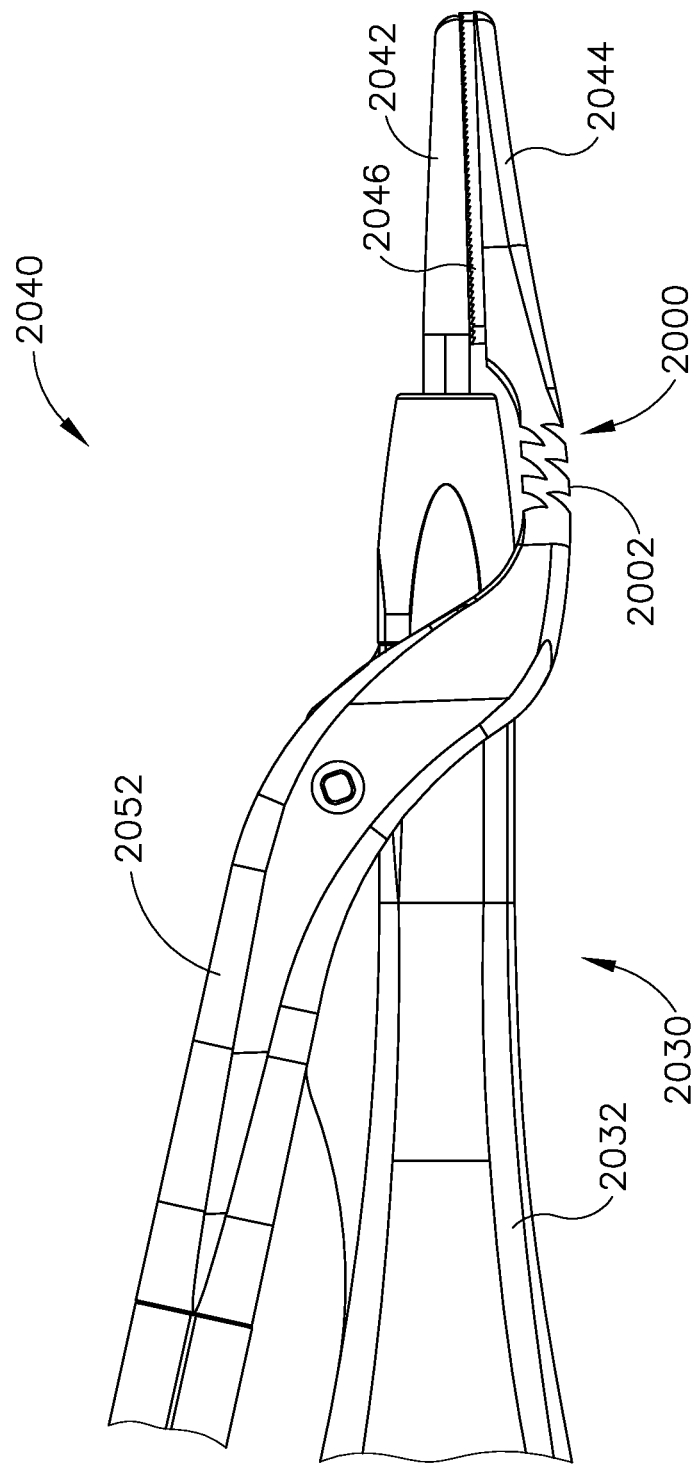
FIG. 22 depicts a side elevational view of an exemplary alternative end effector.
Figure 23:
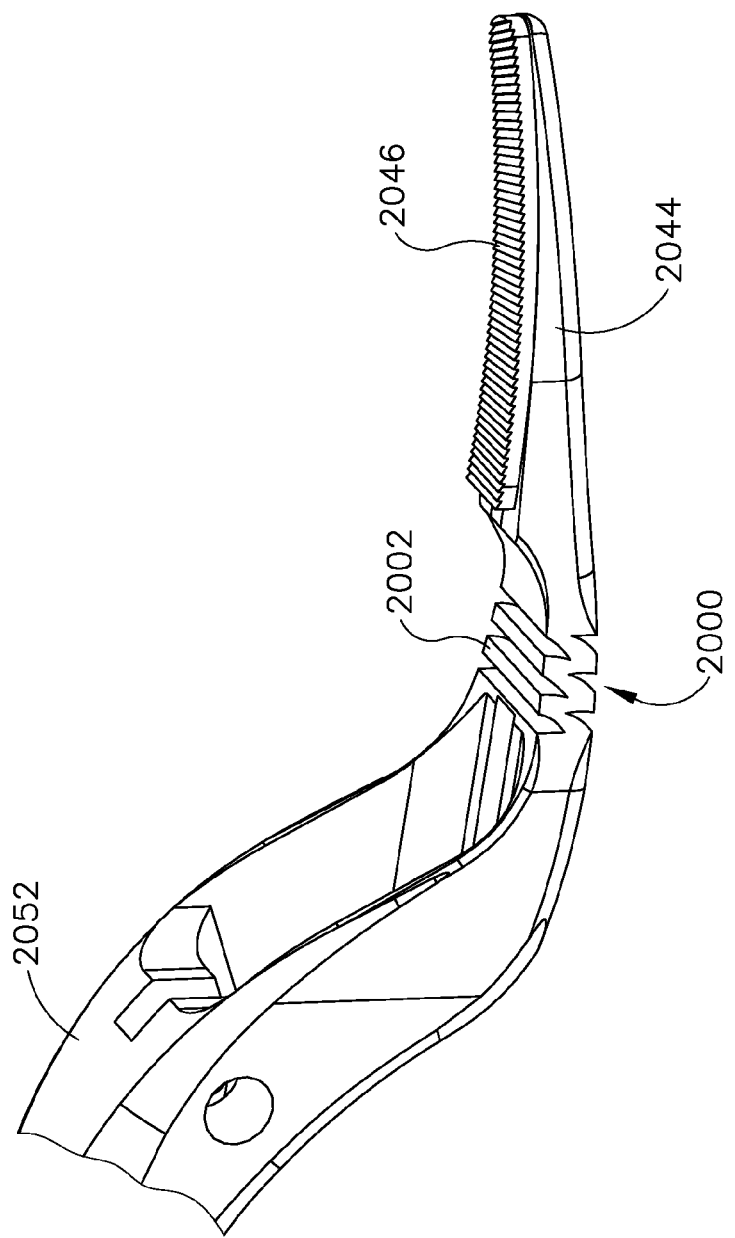
FIG. 23 depicts a perspective view of the clamp arm of the end effector of FIG. 22.

FIGS. 22-23 show another exemplary alternative end effector (2040). End effector (2040) of this example is substantially similar to end effector (140) described above. In particular, end effector (2040) includes an ultrasonic blade (2042) and a pivoting clamp arm (2000) with clamp pad (2046). Shaft assembly (2030) is substantially similar to shaft assembly (130) described above. In particular, shaft assembly (2030) includes an outer sheath (2032) and a cap (2034). Clamp arm (2044) is coupled with a shank (2052) via a flexible section (2000), the combination of which is pivotally coupled with outer sheath (2032) such that clamp arm (2044) pivots toward and away from blade (2042) in response to pivoting of shank (2052) relative to shaft assembly (2030). In the present example, clamp arm (2044), shank (2052), and flexible section (2000) together form a unitary, monolithic structure. In some other versions, clamp arm (2044), shank (2052), and flexible section (2000) are initially separate components that are joined together after they are formed.

Flexible section (2000) is resilient in this example, such that flexible section (2000) is configured to provide a bias to clamp arm (2044). Flexible section (2000) comprises a plurality of segments (2002) that form a zigzag pattern. In some versions, a flexible sleeve (e.g., formed of silicone, etc.) is positioned over flexible section (2000) to prevent segments (2002) from getting snagged on tissue.

When clamp arm (2044) is in a first closed position, the bias of flexible section (2000) urges the distal end of clamp pad (2046) into contact with blade (2042) before the rest of clamp pad (2046) contacts blade (2042). In other words, clamp pad (2046) is non-parallel with the opposing surface of blade (2042) at this stage. As the operator continues to pivot shank (2052) toward shaft assembly (2030), flexible section (2000) begins to deform. This deformation of flexible section (2000) continues to a point where the full length of clamp pad (2046) is in contact with blade (2042). In other words, clamp pad (2046) eventually reaches an orientation where clamp pad (2046) is oriented along a plane that is parallel to the opposing surface of blade (2042).

It should be understood from the foregoing that clamp pad (2046) and blade (2042) will compress tissue captured between the distal regions of clamp pad (2046) and blade (2042) before the proximal regions of clamp pad (2046) and blade (2042) come in contact with each other. To the extent that tissue is positioned between both the distal regions of clamp pad (2046) and blade (2042) and the proximal regions of clamp pad (2046) and blade (2042), the tissue at the distal region will be compressed/transected/sealed first; followed by the tissue at the proximal region. It should also be understood that flexible section (2000) may provide sufficient stiffness to allow a sufficient amount of compression during the first stage of clamp arm (2044) closure. In other words, flexible section (2000) may allow clamp arm (2044) to apply enough compression on tissue to enable end effector (2040) to successfully compress/transect/seal tissue that is captured between the distal regions of clamp pad (2046) and blade (2042), before flexible section (2000) begins to significantly deform. A suitable spring constant for flexible section (2000) will be apparent to those of ordinary skill in the art in view of the teachings herein.

It should also be understood the configuration of segments (2002) may provide a hard stop that prevents flexible section (2000) from flexing any further once end effector (2040) reaches the second stage of closure. For instance, opposing surfaces on the lower regions of segments (2002) may engage each other when end effector (2040) reaches the second stage of closure, and this engagement may prevent further flexing of flexible section (2000). The hard stop may enable the operator to apply a significant amount of clamping force to tissue captured between clamp pad (2046) and blade (2042) after end effector (2040) reaches the second stage of closure. Other suitable variations of end effector (2040) will be apparent to those of ordinary skill in the art in view of the teachings herein.

F. Exemplary Clamp Arm with Resilient Set-Off

Figure 25A:
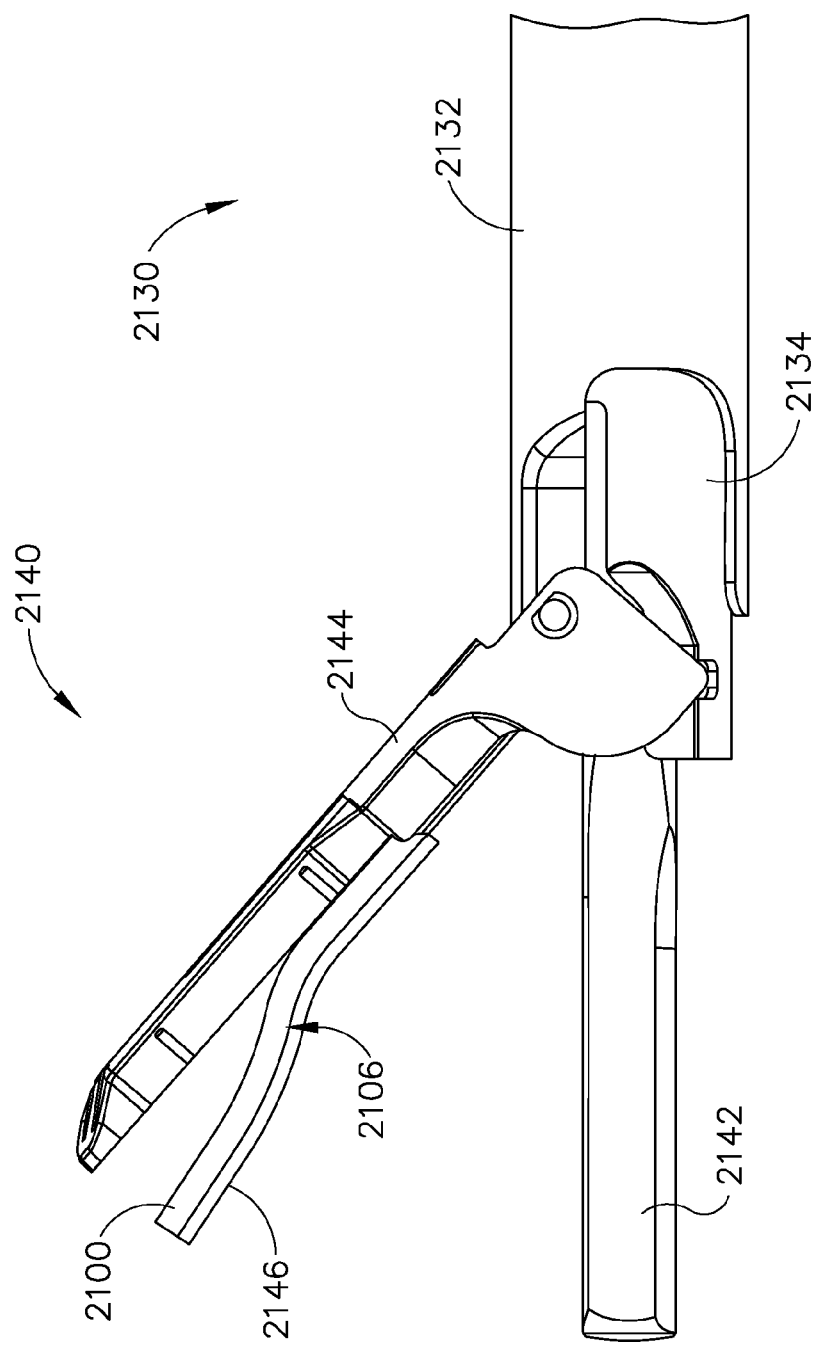
FIG. 25A depicts a side elevational view of the an exemplary end effector, with the clamp arm assembly of FIG. 24 in an open position.
Figure 25B:
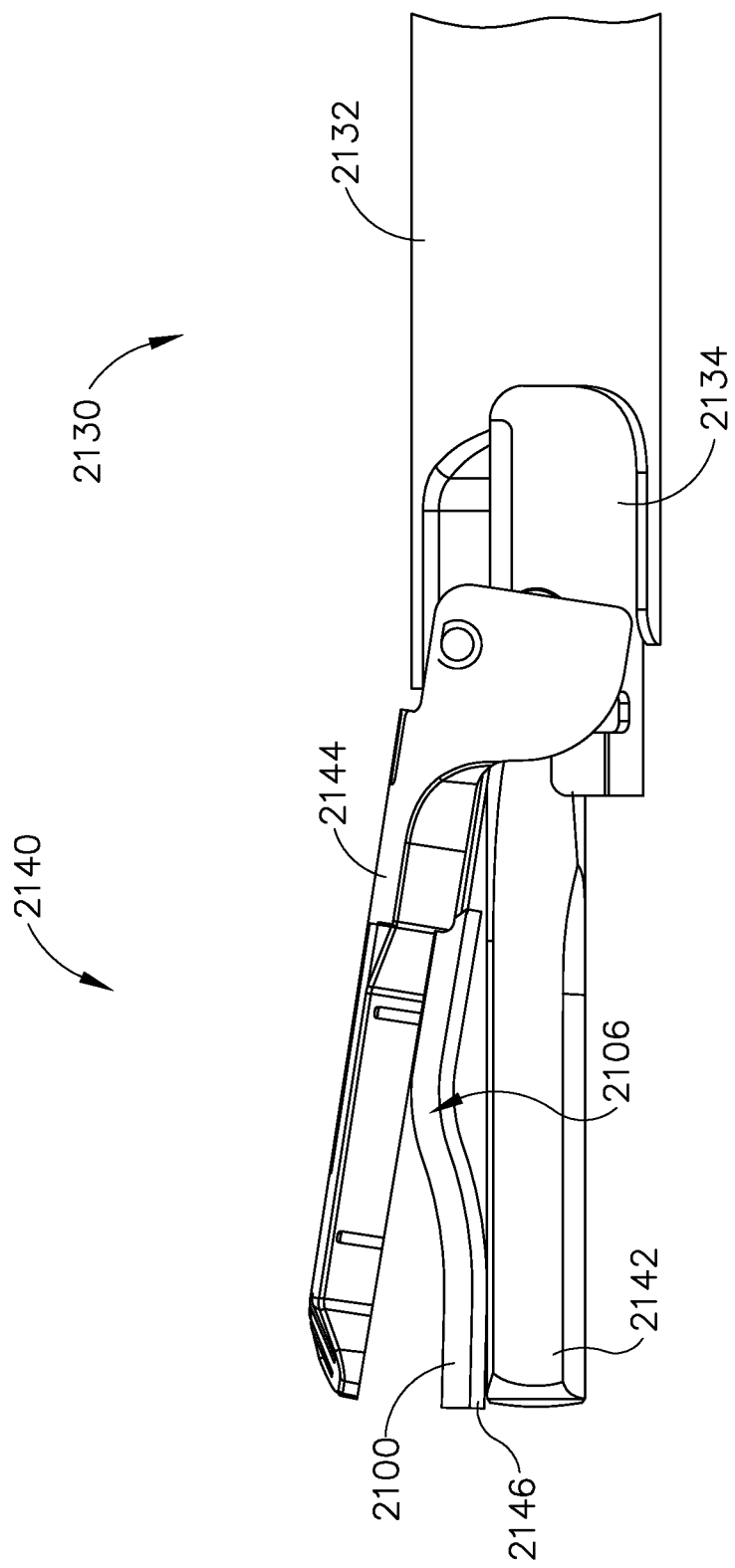
FIG. 25B depicts a side elevational view of the end effector of FIG. 25A, with the clamp arm in a first closed position.
Figure 25C:
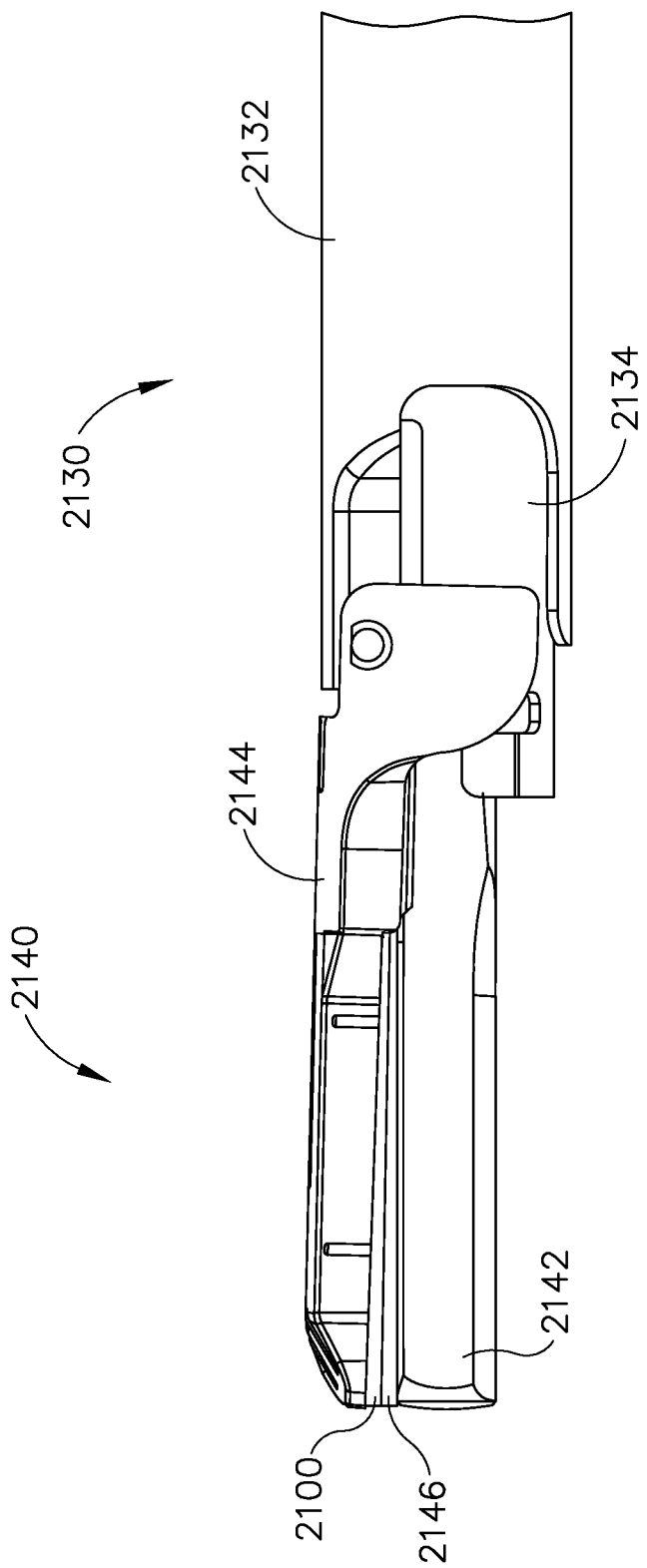
FIG. 25C depicts a side elevational view of the end effector of FIG. 25A, with the clamp arm in a second closed position.

FIGS. 24-25C show components of another exemplary alternative end effector (2140). End effector (2140) of this example is substantially similar to end effector (40) described above. In particular, end effector (2140) includes an ultrasonic blade (2142) and a pivoting clamp arm (2144) with clamp pad (2146). Shaft assembly (2130) is substantially similar to shaft assembly (30) described above. In particular, shaft assembly (2130) includes an outer sheath (2132) and an inner tube (2134). Clamp arm (2144) is pivotally coupled with outer sheath (2132) and with inner tube (2134), such that clamp arm (2144) pivots toward and away from blade (2142) in response to translation of inner tube (2134) relative to outer sheath (2132).

In the present example, clamp pad (2146) is secured to clamp arm (2144) by a leaf spring (2100). Leaf spring (2100) has a dogleg configuration such that the distal portion of leaf spring (2100) is offset from the proximal portion of leaf spring (2100). This provides a gap between the distal end of clamp pad (2146) and the distal end of clamp arm (2144). This dogleg configuration is characterized by a transition region (2106) that provides the offset. In the present example, the transition region (2106) is positioned at the middle of clamp arm (2144) and clamp pad (2146). In some other versions, transition region (2106) is positioned closer to the proximal end of clamp arm (2144) and clamp pad (2146) than the distal end of clamp arm (2144) and clamp pad (2146). In some other versions, the transition region (2106) is positioned closer to the distal end of clamp arm (2144) and clamp pad (2146) than the proximal end of clamp arm (2100) and clamp pad (2146). While the distal portion of leaf spring (2100) is parallel to the proximal portion of leaf spring (2100) in this example, any other suitable orientations may be used. Other suitable configurations and relationships will be apparent to those of ordinary skill in the art in view of the teachings herein. Clamp pad (2146) is flexible in the present example, such that clamp pad (2146) conforms to the shape of leaf spring (2100).

Leaf spring (2100) of the present example is resilient, such that leaf spring (2100) is configured to provide a bias to clamp pad (2146). FIG. 25A shows clamp arm (2144) in an open position, such that clamp arm (2144) is spaced away from blade (2142). It should be understood that end effector (2140) may be maneuvered to position tissue between clamp pad (2146) and blade (2142) while clamp arm (2144) is in an open position as shown in FIG. 25A.

FIG. 25B shows clamp arm (2144) in a first closed position. In this position, the bias and dogleg configuration of leaf spring (2100) urges the distal end of clamp pad (2146) into contact with blade (2142) before the rest of clamp pad (2146) contacts blade (2142). In other words, clamp pad (2146) is non-parallel with the opposing surface of blade (2146) at this stage. As the operator continues to pivot clamp arm (2144) toward blade (2142), leaf spring (2100) begins to deform. Clamp pad (2146) deforms with leaf spring (2100). This deformation of leaf spring (2100) and clamp pad (2146) continues to a point where the full length of clamp pad (2146) is in contact with blade (2142), as shown in FIG. 25C. In other words, clamp pad (2146) eventually reaches an orientation where clamp pad (2146) is oriented along a plane that is parallel to the opposing surface of blade (2142).

It should be understood from the foregoing that clamp pad (2146) and blade (2142) will compress tissue captured between the distal regions of clamp pad (2146) and blade (2142) before the proximal regions of clamp pad (2146) and blade (2142) come in contact with each other. To the extent that tissue is positioned between both the distal regions of clamp pad (2146) and blade (2142) and the proximal regions of clamp pad (2146) and blade (2142), the tissue at the distal region will be compressed/transected/sealed first; followed by the tissue at the proximal region. It should also be understood that leaf spring (2100) may provide sufficient stiffness to allow a sufficient amount of compression during the first stage of clamp arm (2144) closure. In other words, leaf spring (2100) may allow clamp arm (2144) to apply enough compression on tissue to enable end effector (2140) to successfully compress/transect/seal tissue that is captured between the distal regions of clamp pad (2146) and blade (2142), before leaf spring (2100) begins to significantly deform as shown in FIG. 25C. A suitable spring constant for leaf spring (2100) will be apparent to those of ordinary skill in the art in view of the teachings herein.

G. Exemplary Clamp Arm with Pivoting Clamp Pad

Figure 26A:
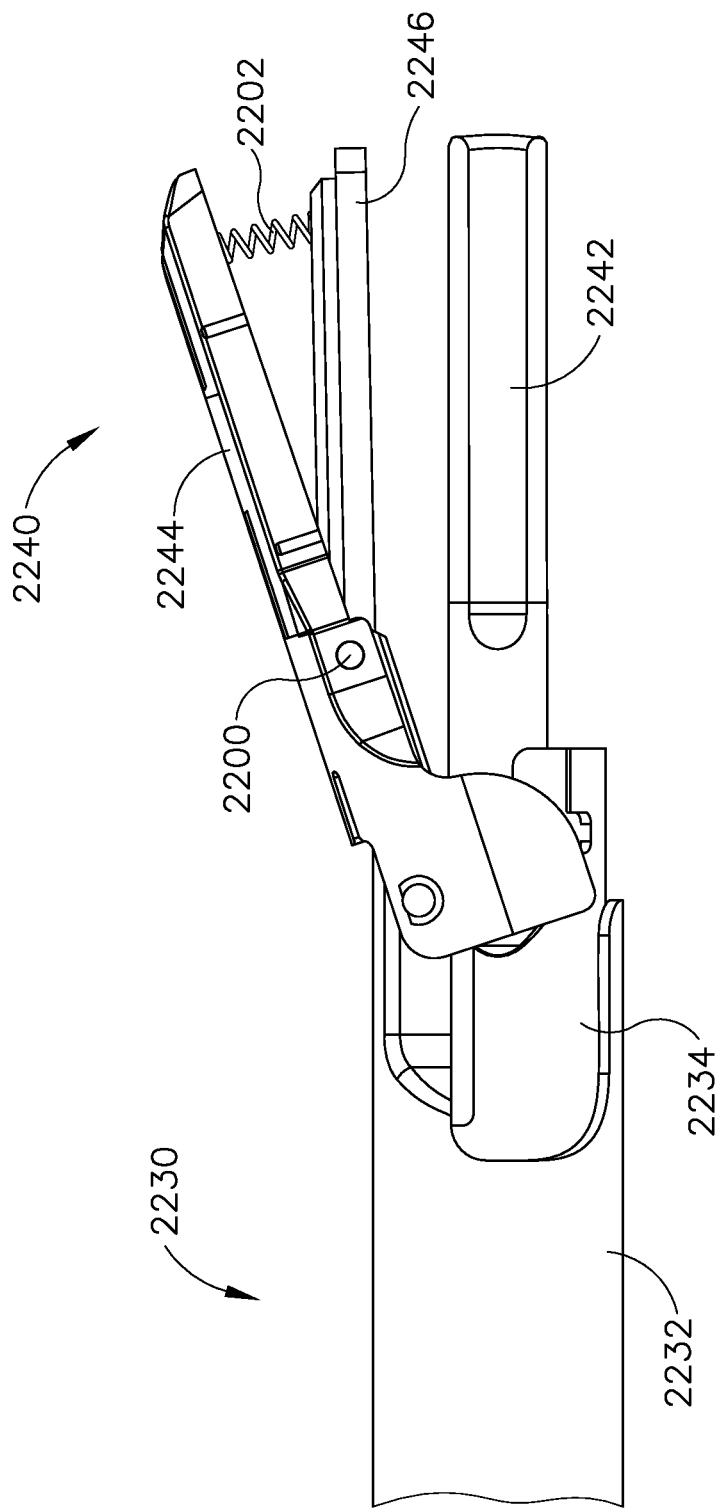
FIG. 26A depicts a side elevational view of another exemplary alternative end effector, with a clamp arm in an open position.
Figure 26B:
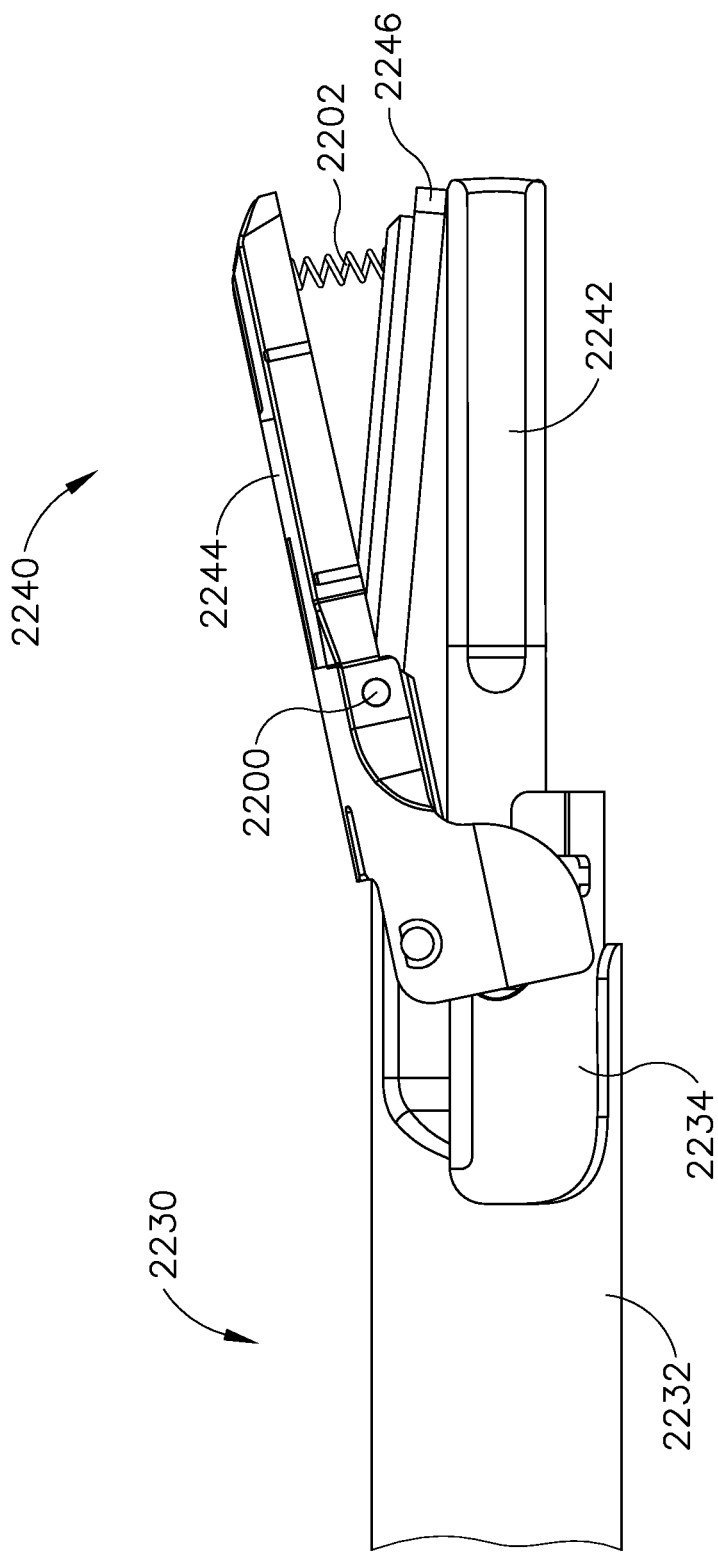
FIG. 26B depicts a side elevational view of the end effector of FIG. 26A, with the clamp arm in a first closed position.
Figure 26C:
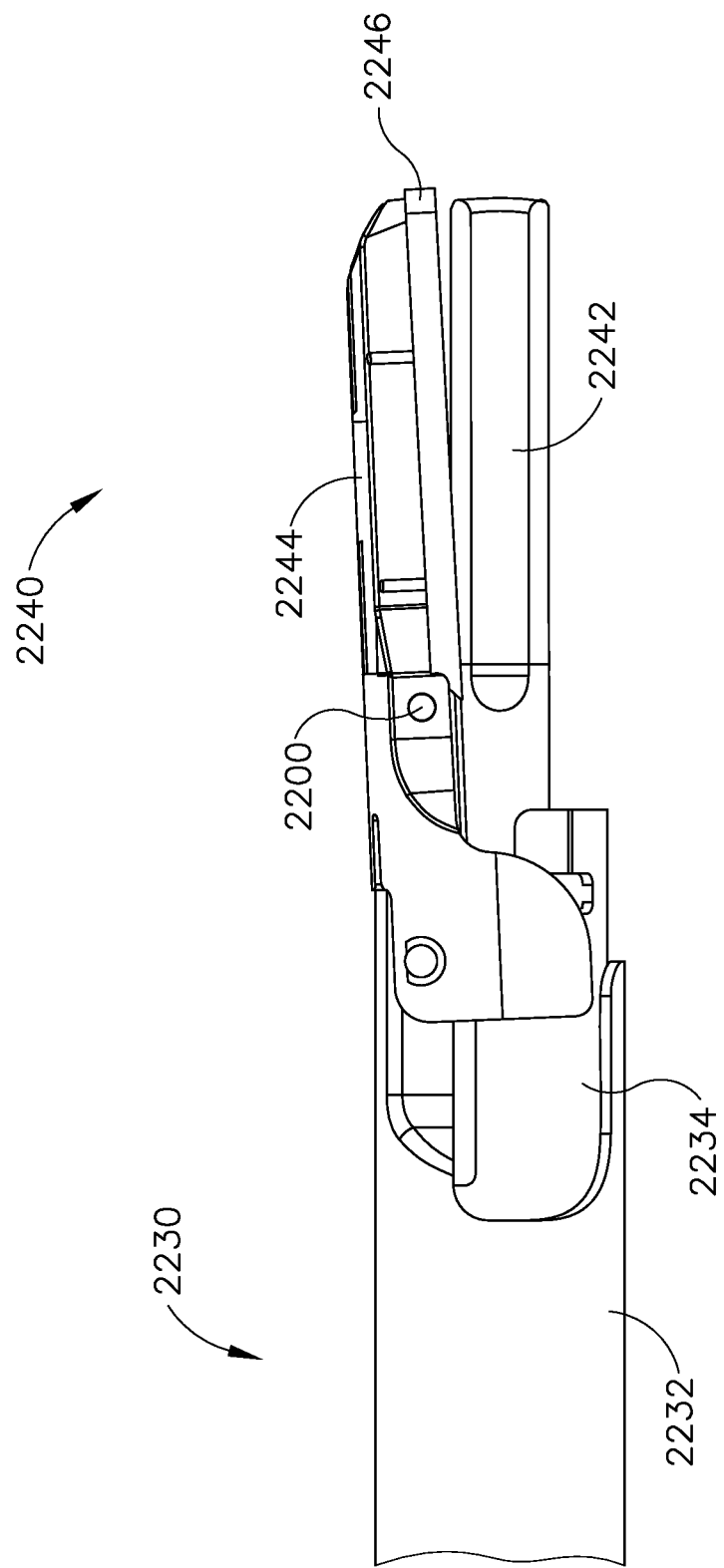
FIG. 26C depicts a side elevational view of the end effector of FIG. 26A, with the clamp arm in a second closed position.

FIGS. 26A-26C show another exemplary alternative end effector (2240). End effector (2240) of this example is substantially similar to end effector (40) described above. In particular, end effector (2240) includes an ultrasonic blade (2242) and a pivoting clamp arm (2244) with clamp pad (2246). Shaft assembly (2230) is substantially similar to shaft assembly (30) described above. In particular, shaft assembly (2230) includes an outer sheath (2232) and an inner tube (2234). Clamp arm (2244) is pivotally coupled with outer sheath (2232) and with inner tube (2234), such that clamp arm (2244) pivots toward and away from blade (2242) in response to translation of inner tube (2234) relative to outer sheath (2232).

In the present example, clamp pad (2246) is pivotally coupled with clamp arm (2244) by a pin (2200). A coil spring (2202) is positioned between the distal end of clamp pad (2246) and the distal end of clamp arm (2244). Coil spring (2202) is configured to bias the distal end of clamp pad (2246) away from the distal end of clamp arm (2244). Of course, any other kind of resilient member may be used, including but not limited to a torsion spring, a leaf spring, etc.

FIG. 26A shows clamp arm (2244) in an open position, such that clamp arm (2244) is spaced away from blade (2242). It should be understood that end effector (2240) may be maneuvered to position tissue between clamp pad (2246) and blade (2242) while clamp arm (2244) is in an open position as shown in FIG. 26A.

FIG. 26B shows clamp arm (2244) in a first closed position. In this position, the bias of coil spring (2202) urges the distal end of clamp pad (2246) into contact with blade (2242) before the rest of clamp pad (2246) contacts blade (2242). In other words, clamp pad (2246) is non-parallel with the opposing surface of blade (2242) at this stage. As the operator continues to pivot clamp arm (2244) toward blade (2242), coil spring (2202) begins to compress. This provides pivoting of clamp pad (2246) toward clamp arm (2244). This compression of coil spring (2202) and pivoting of clamp pad (2246) continues to a point where the full length of clamp pad (2246) is in contact with blade (2242), as shown in FIG. 26C. In other words, clamp pad (2246) eventually reaches an orientation where clamp pad (2246) is oriented along a plane that is parallel to the opposing surface of blade (2242).

It should be understood from the foregoing that clamp pad (2246) and blade (2242) will compress tissue captured between the distal regions of clamp pad (2246) and blade (2242) before the proximal regions of clamp pad (2246) and blade (2242) come in contact with each other. To the extent that tissue is positioned between both the distal regions of clamp pad (2246) and blade (2242) and the proximal regions of clamp pad (2246) and blade (2242), the tissue at the distal region will be compressed/transected/sealed first; followed by the tissue at the proximal region. It should also be understood that coil spring (2202) may provide sufficient stiffness to allow a sufficient amount of compression during the first stage of clamp arm (2244) closure. In other words, coil spring (2202) may allow clamp arm (2244) to apply enough compression on tissue to enable end effector (2240) to successfully compress/transect/seal tissue that is captured between the distal regions of clamp pad (2246) and blade (2242), before coil spring (2202) begins to significantly compress as shown in FIG. 26C. A suitable spring constant for coil spring (2202) will be apparent to those of ordinary skill in the art in view of the teachings herein.

Figure 27:
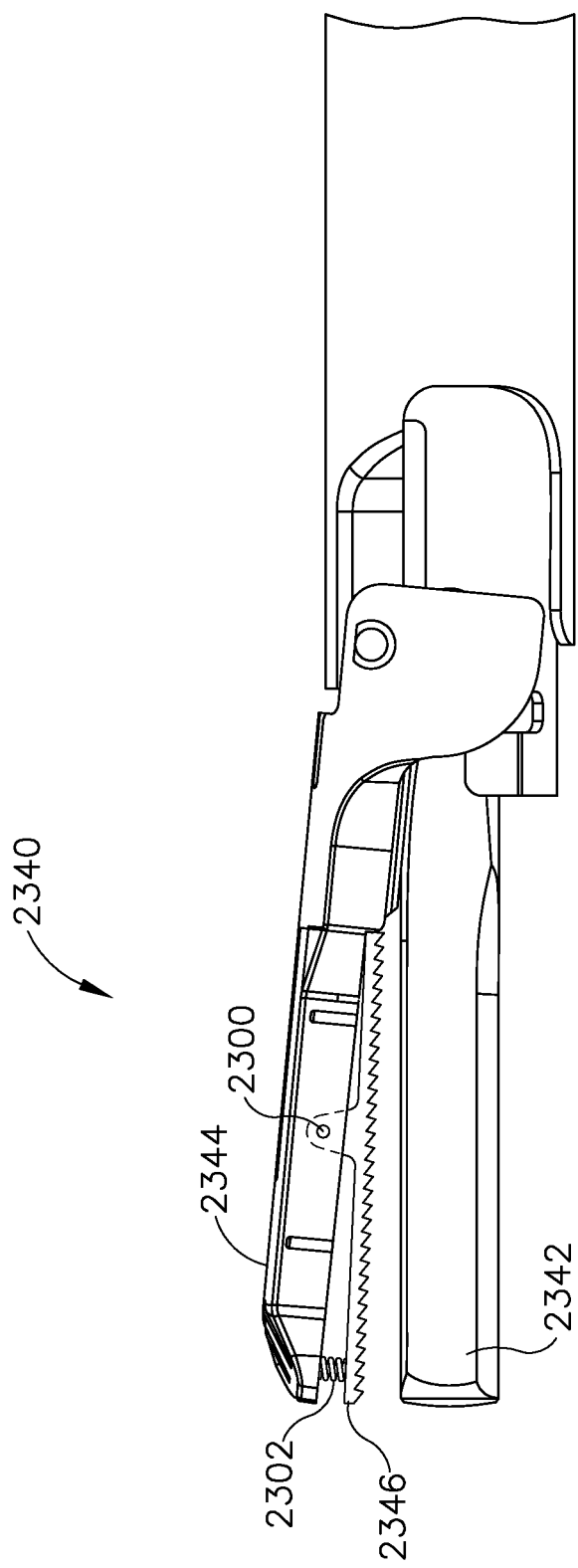
FIG. 27 depicts a side elevational view of another exemplary alternative end effector, with a clamp arm in an open position.

FIG. 27 shows a merely illustrative variation of end effector (2240). In particular, FIG. 27 shows an end effector (2340) that is identical to end effector (2240) except that a pin (2300) joining clamp pad (2346) and clamp arm (2344) is located at the longitudinal midpoint of clamp arm (2344) and clamp pad (2346) (instead of being located at the proximal end of clamp arm (2344) and clamp pad (2346)). As with operation of end effector (2240) described above, the distal end of clamp pad (2346) will first engage blade (2342) before the proximal portion of clamp pad (2346) engages blade (2342) during an initial phase of the closure stroke of clamp arm (2344). Once clamp arm (2344) reaches the full closure stroke, coil spring (2302) compresses and clamp pad (2346) pivots at pin (2300) such that the full length of clamp pad (2346) engages blade (2342).

FIG. 28 shows a merely illustrative variation of end effector (2340). In particular, FIG. 28 shows an end effector (2440) that is identical to end effector (2340) except that a coil spring (2402) biasing clamp pad (2446) about pin (2400) is located at the proximal end of clamp arm (2444) and clamp pad (2446) (instead of being located at the distal end of clamp arm (2444) and clamp pad (2446)). During operation of end effector (2440), the proximal end of clamp pad (2446) will first engage blade (2442) before the distal portion of clamp pad (2446) engages blade (2442) during an initial phase of the closure stroke of clamp arm (2444). Once clamp arm (2444) reaches the full closure stroke, coil spring (2402) compresses and clamp pad (2446) pivots at pin (2400) such that the full length of clamp pad (2446) engages blade (2442). As another variation, the full length of clamp pad (2446) may engage blade (2442) during the initial phase of the closure stroke of clamp arm (2444). It should also be understood that an instrument may include a toggle selector enabling an operator to select between having a coil spring (2302, 2402) positioned distally (as shown in FIG. 27) or proximally (as shown in FIG. 28). Some examples of toggle selection features are described in greater detail below; while other examples will be apparent to those of ordinary skill in the art in view of the teachings herein.

H. Exemplary Clamp Arm with Pivoting Segments

Figure 30A:
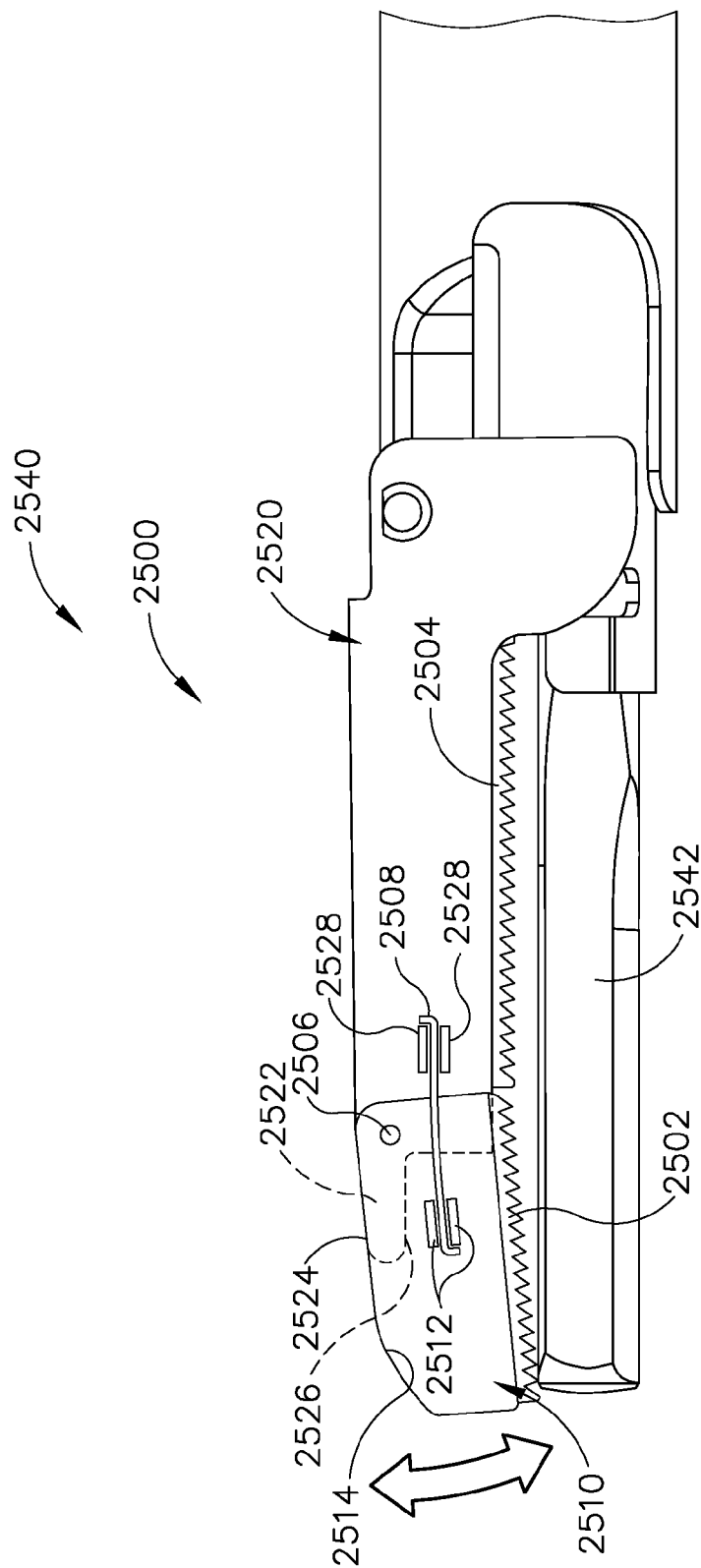
FIG. 30A depicts the clamp arm assembly of FIG. 29 in a first closed position in relation to an ultrasonic blade.
Figure 30B:
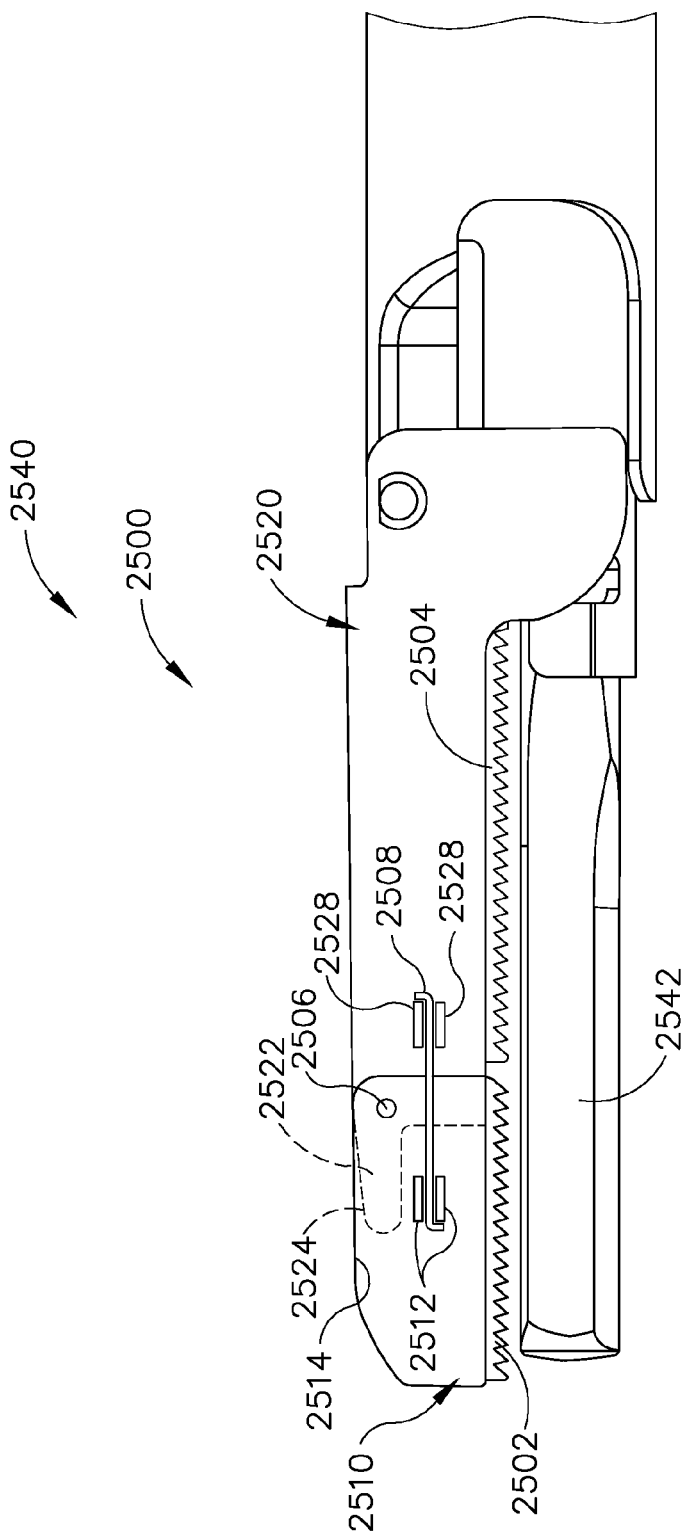
FIG. 30B depicts the clamp arm assembly of FIG. 29 in a second closed position in relation to an ultrasonic blade.

FIGS. 29-30B show components of another exemplary alternative end effector (2540). End effector (2540) of this example is substantially similar to end effector (40) described above. In particular, end effector (2540) includes an ultrasonic blade (2542) and a pivoting clamp arm assembly (2500) with a pair of clamp pads (2502, 2504). Clamp arm assembly (2500) pivots toward and away from blade (2542) in response to translation of an inner tube relative to an outer sheath.

Clamp arm assembly (2500) of the present example comprises a distal segment (2510) and a proximal segment (2520), which are pivotally joined together by a pin (2506). Distal segment (2510) comprises a pair of interior bosses (2512) and an upper interior surface (2514). Clamp pad (2502) is secured to the underside of distal segment (2510). Proximal segment (2520) comprises a distal nose portion (2522) that includes an axially extending lower exterior surface (2526) and an obliquely angled upper exterior surface (2524). Proximal segment (2520) also includes interior bosses (2528). Clamp pad (2504) is secured to the underside of proximal segment (2520). A leaf spring (2508) is secured between bosses (2512) of distal segment (2510) and also between bosses (2528) of proximal segment (2520).

Leaf spring (2508) is configured to resiliently bias distal segment (2510) into an oblique orientation relative to proximal segment (2520), as shown in FIG. 30A. As also shown in FIG. 30A, upper exterior surface (2524) of nose portion (2522) engages the upper interior surface (2514) of distal segment (2510), thereby restricting the pivotal position of distal segment (2510) relative to proximal segment (2520).

During operation of end effector (2540), clamp arm assembly (2500) is pivoted toward the position shown in FIG. 30A, initially capturing tissue between distal clamp pad (2502) and blade (2542). The resilient bias of leaf spring (2508) and the pivotal positioning of segment (2510) by pin (2506) provides engagement between distal clamp pad (2502) and the tissue before proximal clamp pad (2504) contacts either tissue or blade (2542). In other words, clamp pad (2504) is still spaced away from blade (2542) at this stage. As the operator continues to pivot clamp arm assembly (2500) toward blade (2542), leaf spring (2508) begins to deform by substantially straightening out, as clamp arm segments (2510, 2520) pivot relative to each other. Clamp arm segments (2510, 2520) are eventually pivoted into alignment with each other as shown in FIG. 30B. Lower exterior surface (2526) of nose portion (2522) engages the upper boss (2512) of distal segment (2510), providing a hard stop that prevents further pivoting between segments (2510, 2520). At this stage, both clamp pads (2502, 2504) compress tissue against blade (2542).

It should be understood from the foregoing that clamp pad (2502) and blade (2542) will compress tissue before the clamp pad (2504) and blade (2542) come in contact with each other. To the extent that tissue is positioned between both clamp pad (2502) and blade (2542) and clamp pad (2504) and blade (2542), the tissue at the distal region will be compressed/transected/sealed first; followed by the tissue at the proximal region. It should also be understood that leaf spring (2508) may provide sufficient stiffness to allow a sufficient amount of compression while clamp pad (2502) is the only clamp pad (2502, 2504) engaging tissue during the first stage of closure. In other words, leaf spring (2508) may allow clamp pad (2502) to apply enough compression on tissue to enable end effector (2540) to successfully compress/transect/seal tissue that is captured between the clamp pad (2502) and blade (2542), before leaf spring (2508) begins to significantly deform as shown in FIG. 30B. A suitable spring constant for leaf spring (2508) will be apparent to those of ordinary skill in the art in view of the teachings herein.

In some variations of end effector (2540), blade (2542) includes a bump or other protrusion extending toward a region of clamp pad (2502) associated with a low point in the pressure profile during the closure stroke of clamp arm assembly (2500). A suitable location and configuration for such a bump or other protrusion will be apparent to those of ordinary skill in the art in view of the teachings herein. It should also be understood that clamp pads (2502, 2504) may be substituted with a single clamp pad that extends along both segments (2510, 2520). Such a single clamp pad may be flexible, could include a hinge, or could have some other configuration. Furthermore, while clamp arm assembly (2500) of the present example has two segments (2510, 2520), clamp arm assembly (2500) may instead have three or more segments. Other suitable variations of end effector (2540) will be apparent to those of ordinary skill in the art in view of the teachings herein.

I. Exemplary Clamp Arm with Wedge-Shaped Clamp Pad

Figure 31A:
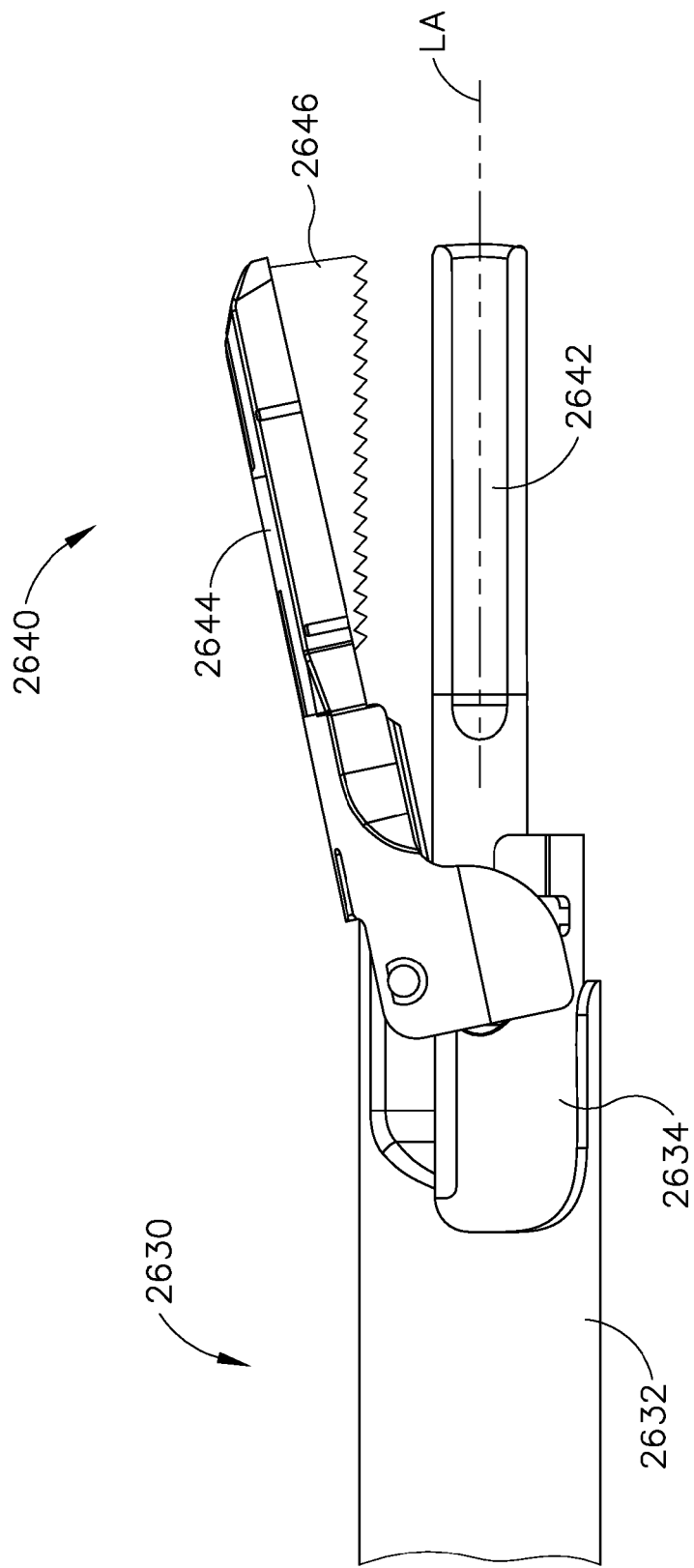
FIG. 31A depicts a side elevational view of another exemplary alternative end effector, with a clamp arm in an open position.
Figure 31B:
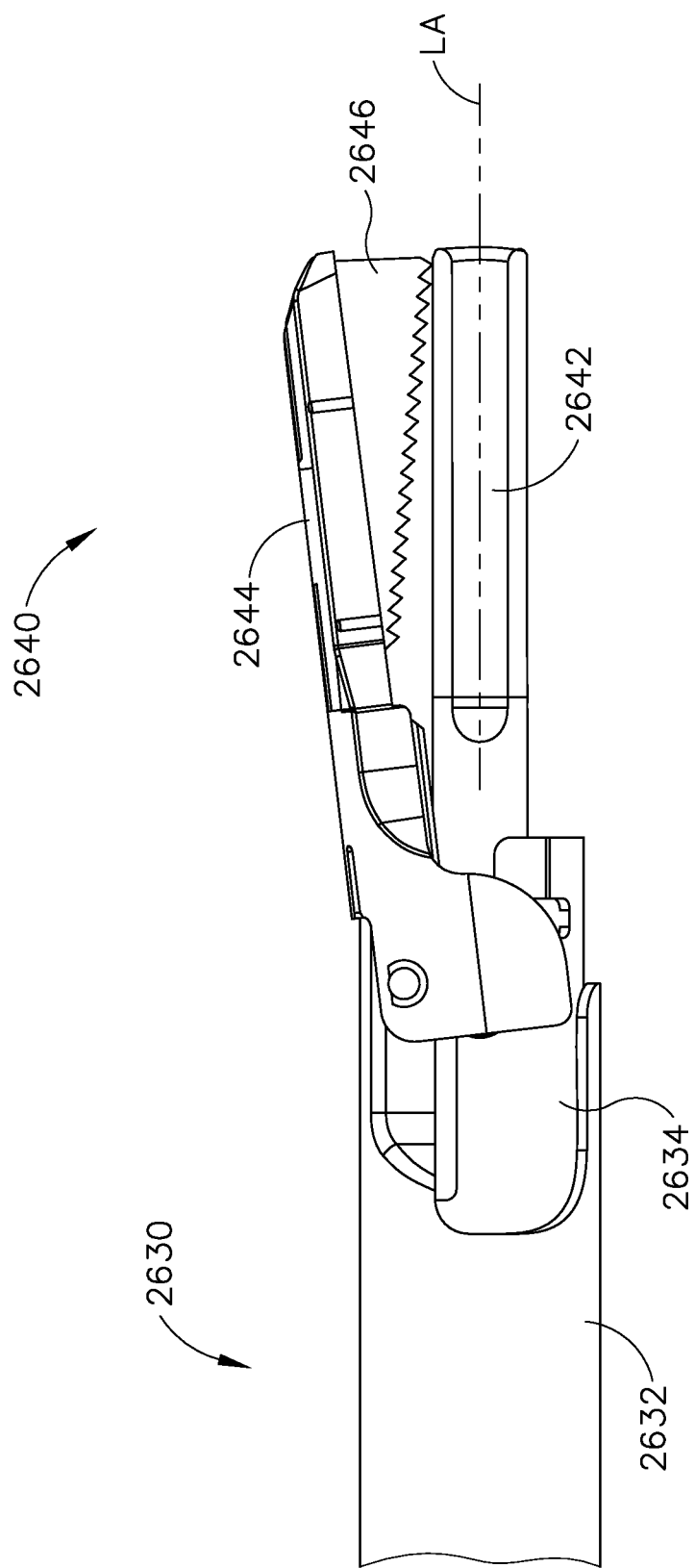
FIG. 31B depicts a side elevational view of the end effector of FIG. 31A, with the clamp arm in a first closed position.
Figure 31C:
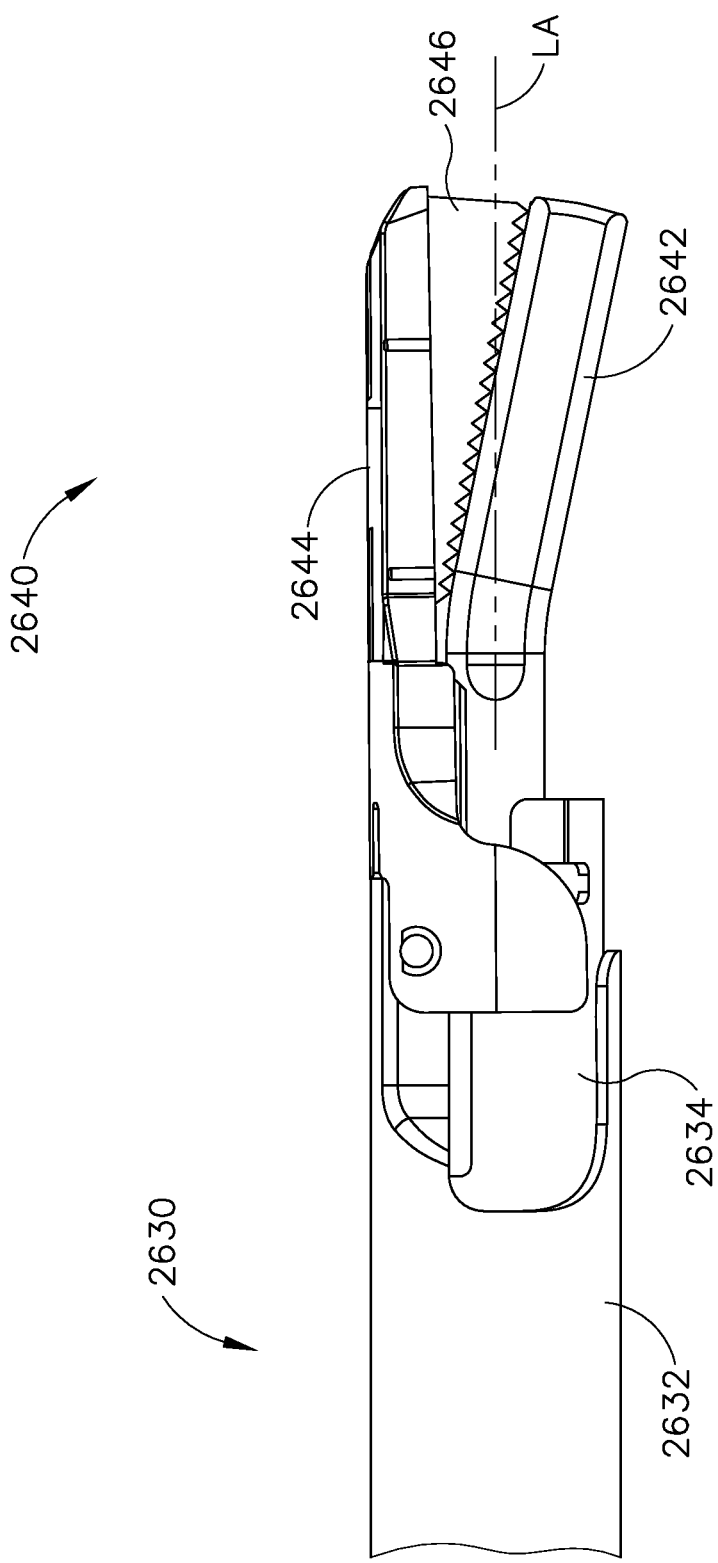
FIG. 31C depicts a side elevational view of the end effector of FIG. 31A, with the clamp arm in a second closed position.

FIGS. 31A-31C show another exemplary alternative end effector (2640). End effector (2640) of this example is substantially similar to end effector (40) described above. In particular, end effector (2640) includes an ultrasonic blade (2642) and a pivoting clamp arm (2644) with clamp pad (2646). Shaft assembly (2630) is substantially similar to shaft assembly (30) described above. In particular, shaft assembly (2630) includes an outer sheath (2632) and an inner tube (2634). Clamp arm (2644) is pivotally coupled with outer sheath (2632) and with inner tube (2634), such that clamp arm (2644) pivots toward and away from blade (2642) in response to translation of inner tube (2634) relative to outer sheath (2632).

Clamp pad (2646) of the present example has a wedge shape. In particular, the distal portion of clamp pad (2646) is thicker than the proximal portion of clamp pad (2646), with the thickness gradually tapering down from the distal end to the proximal end. The taper of clamp pad (2646) is configured such that the distal end of clamp pad (2646) will contact blade (2642) before the proximal end of clamp pad (2646).

FIG. 31A shows clamp arm (2644) in an open position, such that clamp arm (2644) is spaced away from blade (2642). It should be understood that end effector (2640) may be maneuvered to position tissue between clamp pad (2646) and blade (2642) while clamp arm (2644) is in an open position as shown in FIG. 31A.

FIG. 31B shows clamp arm (2644) in a first closed position. In this position, the taper of clamp pad (2646) provides contact between the distal end of clamp pad (2646) and blade (2642) before the rest of clamp pad (2646) contacts blade (2642). In other words, clamp pad (2646) is non-parallel with the opposing surface of blade (2642) at this stage. As the operator continues to pivot clamp arm (2644) toward blade (2642), clamp pad (2646) deforms blade (2642) to a point where the full length of clamp pad (2646) is in contact with blade (2642), as shown in FIG. 31C. In other words, clamp pad (2646) and blade (2642) together eventually reach an orientation where clamp pad (2646) is oriented along a plane that is parallel to the opposing surface of blade (2642). Blade (2642) is deflected relative to a longitudinal axis (LA) at this stage.

It should be understood from the foregoing that clamp pad (2646) and blade (2642) will compress tissue captured between the distal regions of clamp pad (2646) and blade (2242) before the proximal regions of clamp pad (2246) and blade (2242) come in contact with each other. To the extent that tissue is positioned between both the distal regions of clamp pad (2646) and blade (2642) and the proximal regions of clamp pad (2646) and blade (2642), the tissue at the distal region will be compressed/transected/sealed first; followed by the tissue at the proximal region. It should also be understood that the depicted angle of taper of clamp pad (2646) shown in FIGS. 31A-31C, and the depicted angle of deflection of blade (2642) shown in FIG. 31C, are exaggerated for illustrative effect. In practice, the angles of taper and deflection may be significantly smaller than what is shown in the present drawings. Furthermore, the angle of taper may be different from the angle of deflection. Suitable angles of taper and deflection will be apparent to those of ordinary skill in the art in view of the teachings herein.

J. Exemplary Cam Paths for Clamp Arm Pivot Pins

The examples described above provide staged engagement where the distal regions of the clamp pad and blade engage first, followed by the proximal regions of the clamp pad and blade. Thus, at the end of the closure stroke for the clamp arm, the full length of the clamp pad may be in contact with the blade. Even if tissue is interposed between portions of the lengths of the clamp pad and blade, the rest of the lengths of the clamp pad and blade may still be in direct contact with each other. Instead of providing this full length or significant length contact, it may be desirable to provide controlled, minimized local contact throughout the entire closure stroke of the clamp arm. In other words, it may be desirable to provide localized contact between the clamp pad and the blade, with the position of the localized contact changing during the closure stroke of the clamp arm. The examples described below provide such localized, dynamic contact between the clamp pad and the blade during the closure stroke of the clamp arm.

In the examples described below, the localized contact begins at the proximal end of the clamp arm and blade and moves distally along the corresponding lengths of the clamp arm and blade. In some variations, the localized contact begins at the distal end of the clamp arm and blade and moves proximally along the corresponding lengths of the clamp arm and blade. In either case, it should be understood the controlled localization of the contact may minimize the amount of heat that might otherwise be generated in the clamp arm and/or in the blade from direct contact during activation of the blade. In other words, the localized, dynamic contact described below may reduce the generation of heat similar to the reduction in heat generated by the end effectors having staged contact between a clamp pad and blade as described above.

Figure 32B:
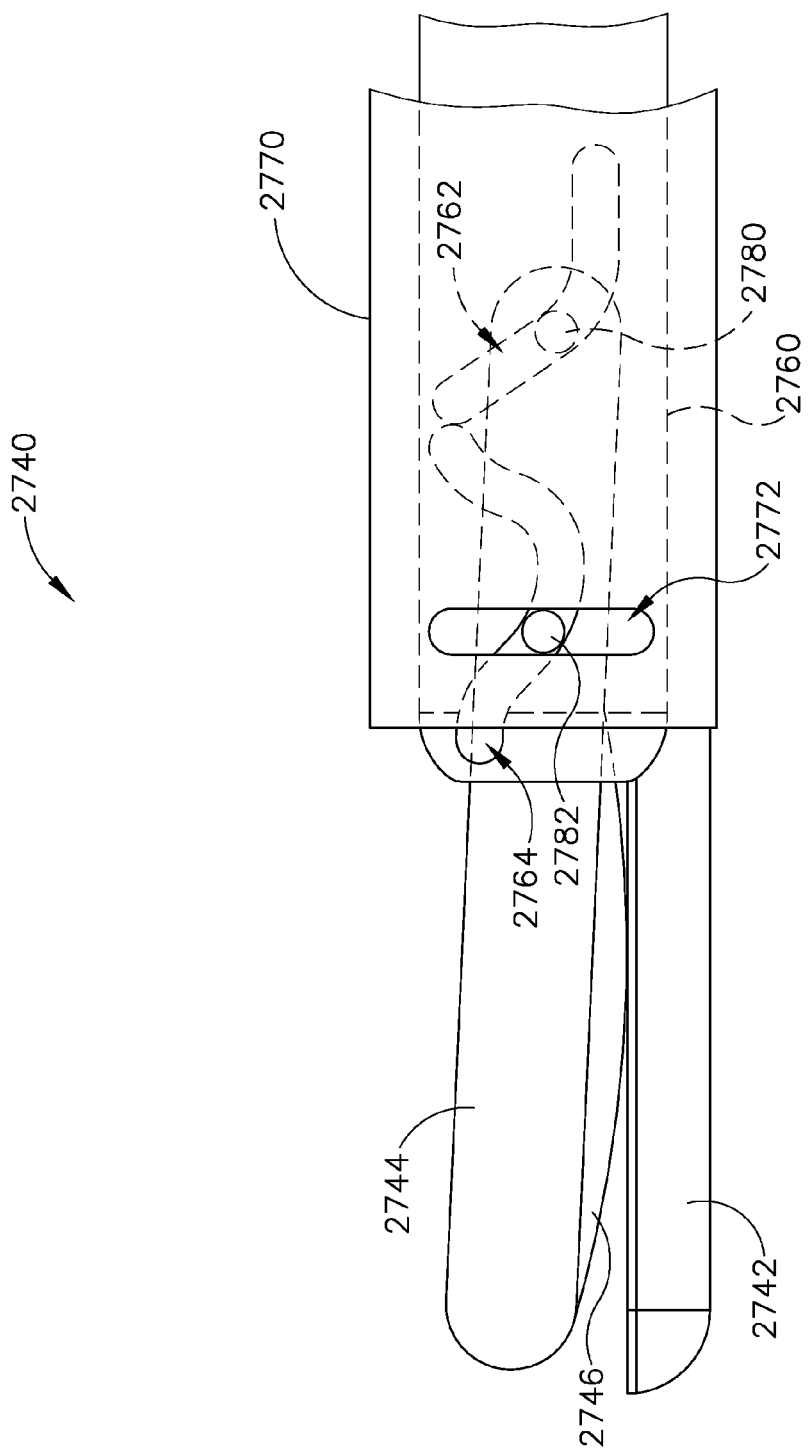
FIG. 32B depicts a side elevational view of the end effector of FIG. 32A, with the clamp arm in a first closed position.
Figure 32C:
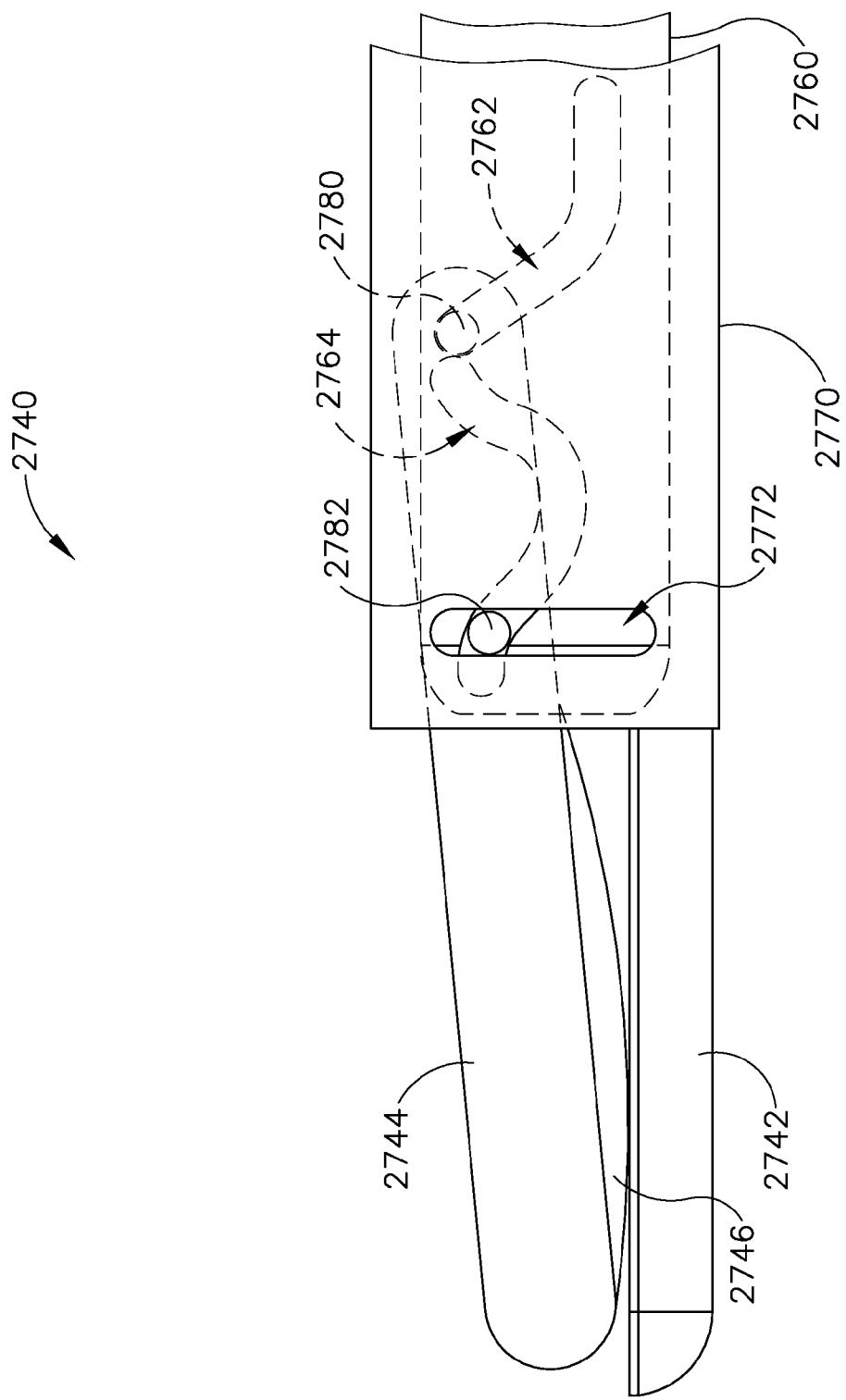
FIG. 32C depicts a side elevational view of the end effector of FIG. 32A, with the clamp arm in a second closed position.

FIGS. 32A-32C show an exemplary end effector (2740) that includes an ultrasonic blade (2742), a clamp arm (2744), and a clamp pad (2746). By way of example only, end effector (2740) may be used to substitute end effector (40) in instrument (10). End effector (2740) of this example provides localized, dynamic contact between clamp pad (2746) and blade (2742). In particular, clamp arm (2744) is driven by proximal translation of an inner tube (2760) relative to an outer tube (2770). Inner tube (2760) defines a proximal cam channel (2762) and a distal cam channel (2764). Outer tube (2770) defines a vertically extending retainer channel (2772). Clamp arm (2744) includes a proximal pin (2780) that is slidably disposed within proximal cam channel (2762). Clamp arm (2744) also includes a distal pin (2782) that is slidably disposed within both distal cam channel (2764) and retainer channel (2772). In the present example, pins (2780, 2782) extend outwardly from both lateral sides of clamp arm (2744). It should therefore be understood that the side of inner tube (2760) that is opposite to the depicted side of inner tube (2760) may include channels that are identical to channels (2762, 2764). Likewise, the side of outer tube (2770) that is opposite to the depicted side of outer tube (2770) may include a channel that is identical to channel (2772).

Channels (2762, 2764) and the tissue contacting surface of clamp pad (2746) are contoured to provide localized, dynamic contact between clamp pad (2746) and blade (2742). In particular, when inner tube (2760) is in a distal position relative to outer tube (2770), clamp arm (2744) is in an open position such that clamp pad (2746) is spaced away from blade (2742) as shown in FIG. 32A. At this stage, tissue may be positioned between clamp pad (2746) and blade (2742). With tissue appropriately positioned, inner tube (2760) is retracted proximally relative to outer tube (2770) to drive clamp arm (2744) and clamp pad (2746) toward blade (2742). Through camming interaction between pins (2780, 2782) and corresponding channels (2762, 2764, 2782), this retraction of inner tube (2760) relative to outer tube (2770) causes clamp arm (2744) to pivot toward blade (2742). As shown in FIG. 32B, this initially provides contact between a localized proximal portion of clamp pad (2746) and blade (2742). As inner tube (2760) continues to retract relative to outer tube (2770), camming interaction between pins (2780, 2782) and corresponding channels (2762, 2764, 2782) continues to drive clamp arm (2744) toward blade (2742). As shown in FIG. 32C, this transitions the localized contact between clamp pad (2746) and blade (2742) distally from a proximal portion of clamp pad (2746) to a distal portion of clamp pad (2746). Thus, at any given moment during the closure stroke of clamp arm (2744), only a small localized portion of clamp pad (2746) may contact blade (2742). It should be understood that the transection/sealing of tissue in end effector (2740) may move distally along the length of blade (2742) in accordance with the dynamic contact between clamp pad (2746) and blade (2742).

Figure 33B:
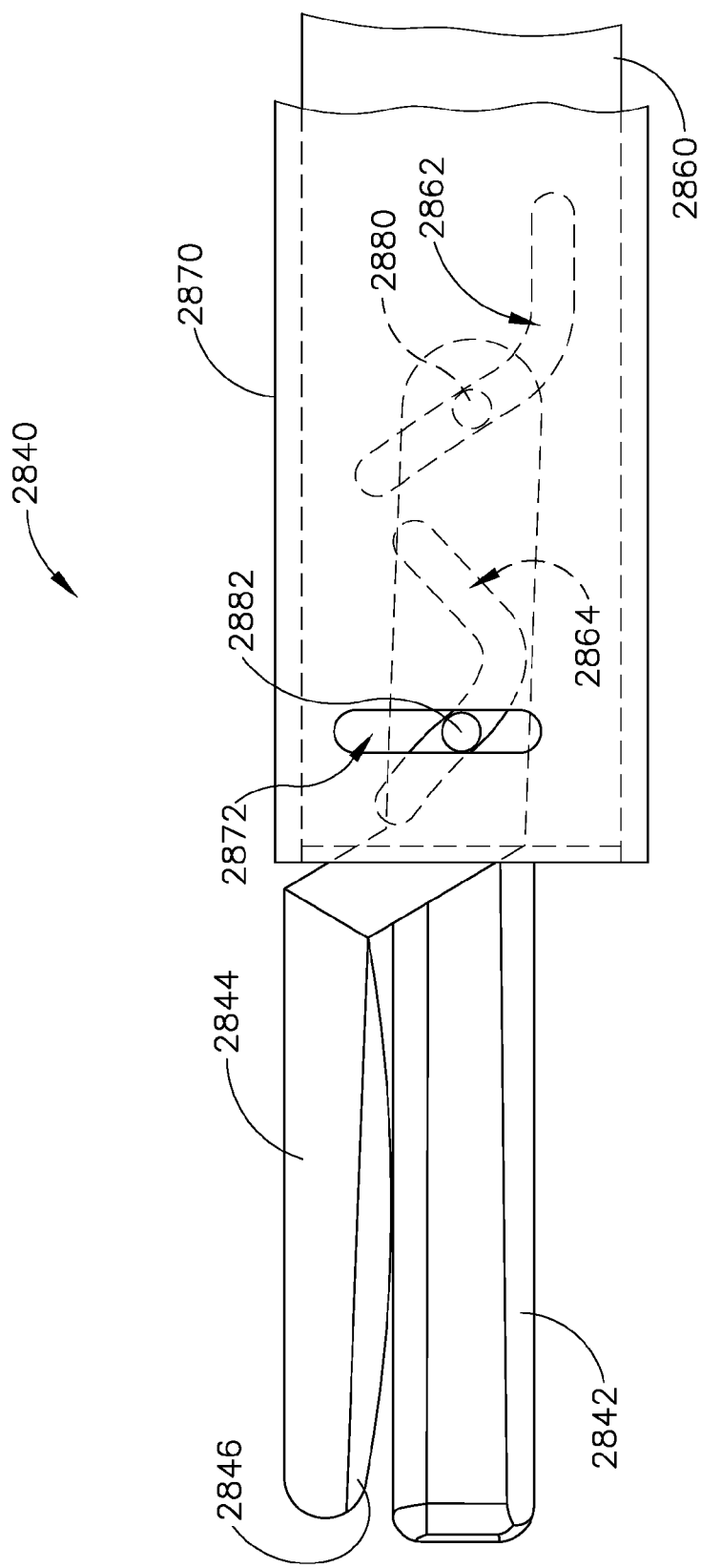
FIG. 33B depicts a side elevational view of the end effector of FIG. 33A, with the clamp arm in a first closed position.

FIGS. 33A-33C show another exemplary end effector (2840) that includes an ultrasonic blade (2842), a clamp arm (2844), and a clamp pad (2846). By way of example only, end effector (2840) may be used to substitute end effector (40) in instrument (10). End effector (2840) of this example provides localized, dynamic contact between clamp pad (2846) and blade (2842). In particular, clamp arm (2844) is driven by proximal translation of an inner tube (2860) relative to an outer tube (2870). Inner tube (2860) defines a proximal cam channel (2862) and a distal cam channel (2864). Outer tube (2870) defines a vertically extending retainer channel (2872). Clamp arm (2844) includes a proximal pin (2880) that is slidably disposed within proximal cam channel (2862). Clamp arm (2844) also includes a distal pin (2882) that is slidably disposed within both distal cam channel (2864) and retainer channel (2872). In the present example, pins (2880, 2882) extend outwardly from both lateral sides of clamp arm (2844). It should therefore be understood that the side of inner tube (2860) that is opposite to the depicted side of inner tube (2860) may include channels that are identical to channels (2862, 2864). Likewise, the side of outer tube (2870) that is opposite to the depicted side of outer tube (2870) may include a channel that is identical to channel (2872).

Channels (2862, 2864) and the tissue contacting surface of clamp pad (2846) are contoured to provide localized, dynamic contact between clamp pad (2846) and blade (2842). In particular, when inner tube (2860) is in a distal position relative to outer tube (2870), clamp arm (2844) is in an open position such that clamp pad (2846) is spaced away from blade (2842) as shown in FIG. 33A. At this stage, tissue may be positioned between clamp pad (2846) and blade (2842). With tissue appropriately positioned, inner tube (2860) is retracted proximally relative to outer tube (2870) to drive clamp arm (2844) and clamp pad (2846) toward blade (2842). Through camming interaction between pins (2880, 2882) and corresponding channels (2862, 2864, 2882), this retraction of inner tube (2860) relative to outer tube (2870) causes clamp arm (2844) to pivot toward blade (2842). As shown in FIG. 33B, this initially provides contact between a localized proximal portion of clamp pad (2846) and blade (2842). As inner tube (2860) continues to retract relative to outer tube (2870), camming interaction between pins (2880, 2882) and corresponding channels (2862, 2864, 2882) continues to drive clamp arm (2844) toward blade (2842). As shown in FIG. 33C, this transitions the localized contact between clamp pad (2846) and blade (2842) distally from a proximal portion of clamp pad (2846) to a distal portion of clamp pad (2846). Thus, at any given moment during the closure stroke of clamp arm (2844), only a small localized portion of clamp pad (2846) may contact blade (2842). It should be understood that the transection/sealing of tissue in end effector (2840) may move distally along the length of blade (2842) in accordance with the dynamic contact between clamp pad (2846) and blade (2842).

K. Exemplary Clamp Pad with Curved Tip

When the distal end of a clamp pad (46, 146) reaches full apposition with the distal end of a blade (42, 142), clamp pad (46, 146) and blade (42, 142) may have cooperated to completely sever tissue that had previously been between the distal end of clamp pad (46, 146) and the distal end of blade (42, 142). In some instances, it may be desirable to avoid such severing at the distal end of clamp pad (46, 146) and the distal end of blade (42, 142). In particular, it may be desirable to provide a small gap at the distal end of clamp pad (46, 146) and the distal end of blade (42, 142), to prevent severing of tissue at the distal end of clamp pad (46, 146) and the distal end of blade (42, 142).

Figure 34:
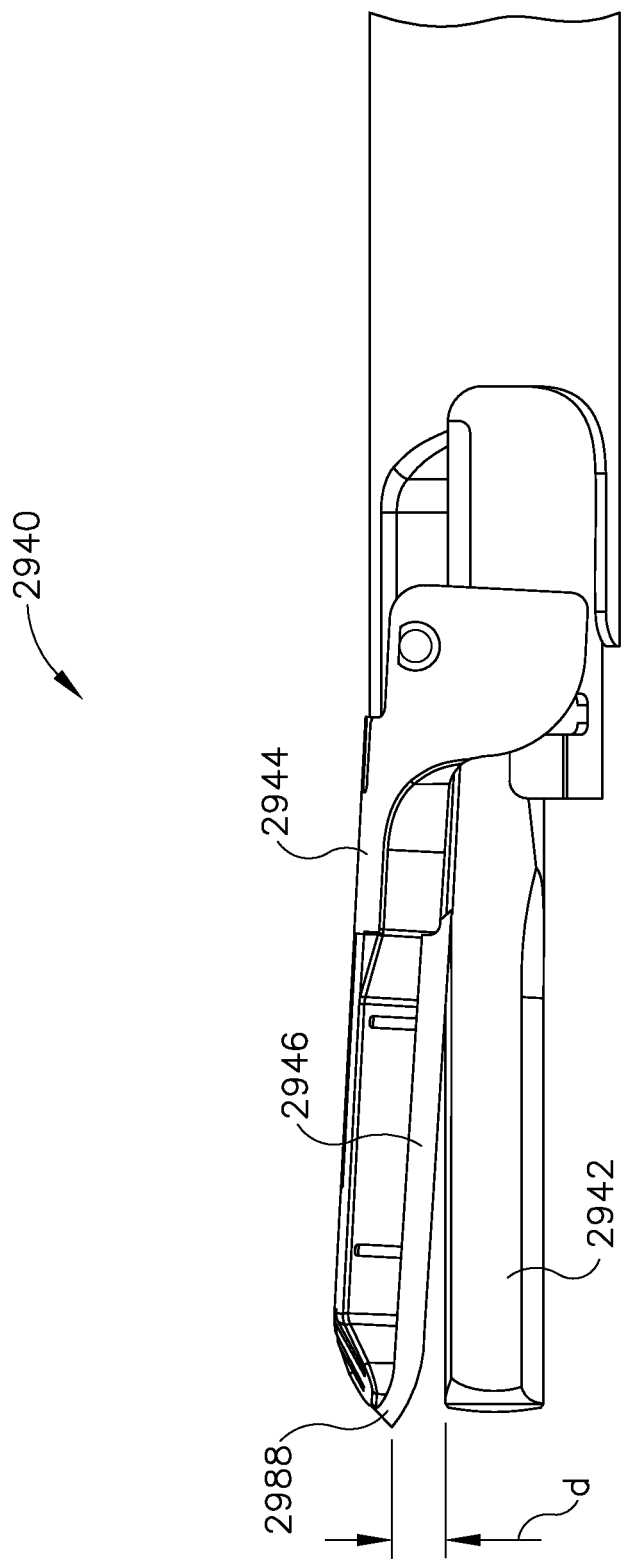
FIG. 34 depicts another exemplary alternative end effector, in a closed configuration.
Figure 35:
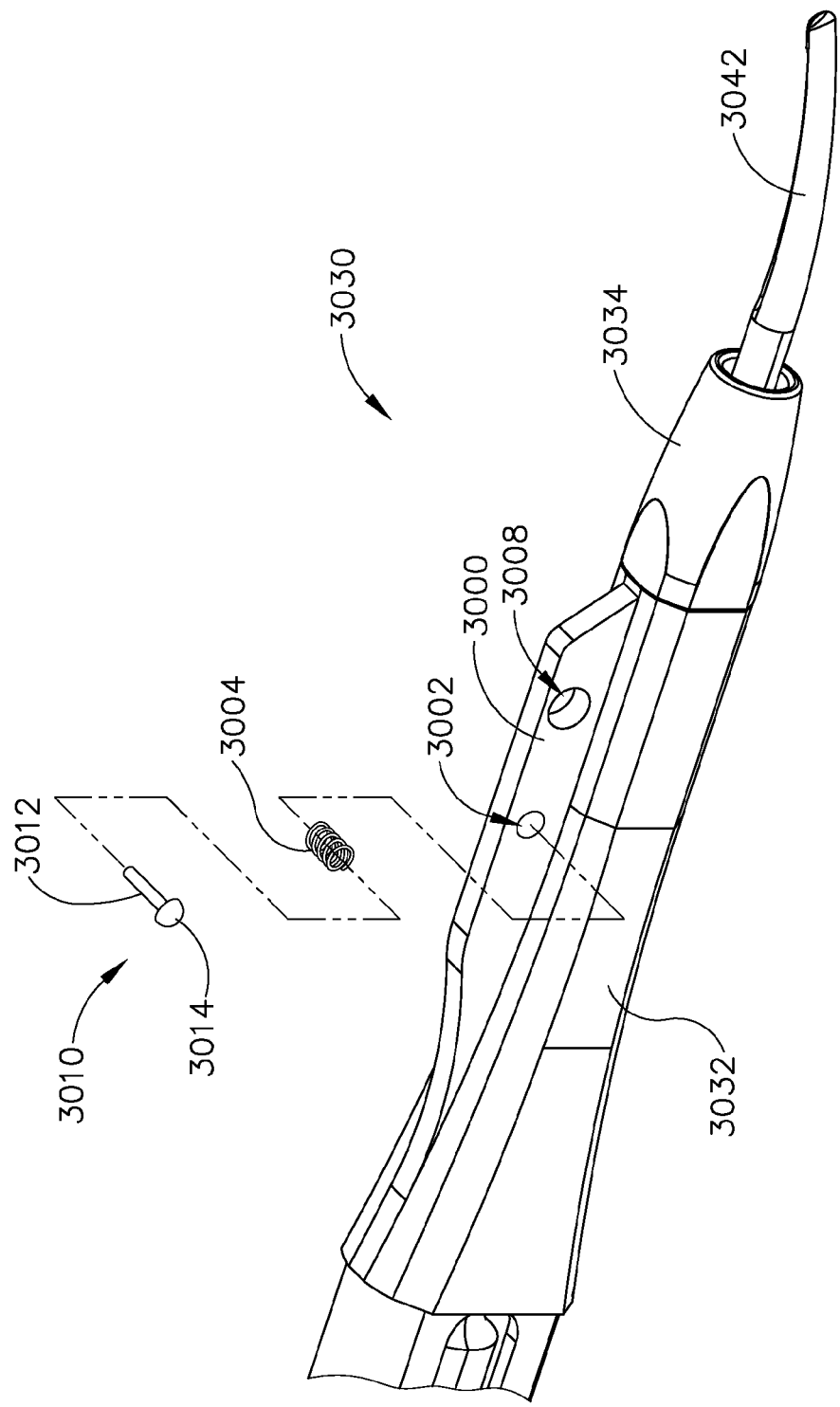
FIG. 35 depicts an exploded view of an exemplary detent feature of an exemplary alternative shaft assembly.

FIG. 34 shows an exemplary alternative end effector (2940) that comprises an ultrasonic blade (2942), a clamp arm (2944), and a clamp pad (2946). It should be understood that end effector (2940) may be readily incorporated into instrument (10) in place of end effector (40). Clamp arm (2944) and clamp pad (2946) are configured to provide clamp pad (2946) with an upwardly curved distal tip (2988). This configuration provides a gap distance (d) between distal tip (2988) and blade (2942), even when clamp arm (2944) is in a fully closed position as is shown in FIG. 35. Thus, when tissue is fully clamped between clamp pad (2946) and blade (2942), the tissue between distal tip (2988) and blade (2942) will not be severed. Instead, the pressure gradient provided in the tissue within the gap between distal tip (2988) and blade (2942) will promote sealing of the tissue. The curved configuration of distal tip (2988) may thus reduce chances of tissue bleeding that might otherwise occur in versions where distal tip (2988) reaches full apposition with blade (2942). In some other variations, distal tip (2988) is obliquely angled upwardly along a substantially straight path, rather than being curved.

As described in greater detail below, some end effectors may be switchable between a staged contact mode and a full contact mode. In the staged contact mode, the distal regions of the clamp pad and blade engage first, followed by the proximal regions of the clamp pad and blade. In the full contact mode, the full length of the clamp pad engages the blade substantially simultaneously. It should be understood that end effector (2940) may be readily adapted to provide such switchable modes. The configuration of end effector (2940) shown in FIG. 34 may be associated with the full contact mode.

L Exemplary Feature for Clamp Arm Stage Tactile Feedback

Various exemplary end effectors described above provide staged engagement where the distal regions of the clamp pad and blade engage first, followed by the proximal regions of the clamp pad and blade. In some instances, it may be difficult for the operator to visualize when an end effector is transitioning from a state where only the distal regions of the clamp pad and blade are engaging to a state where the proximal regions of the clamp pad and blade are also engaging. It may therefore be desirable to provide some form of tactile feedback to inform the operator when the end effector is transitioning from the distal engagement state (e.g., as shown in FIGS. 9B, 15A, 21B, 25B, 26B, 30A, 31B) to the full length engagement state (e.g., as shown in FIGS. 9C, 15B, 21C, 25C, 26C, 30B, 31C).

Figure 36:
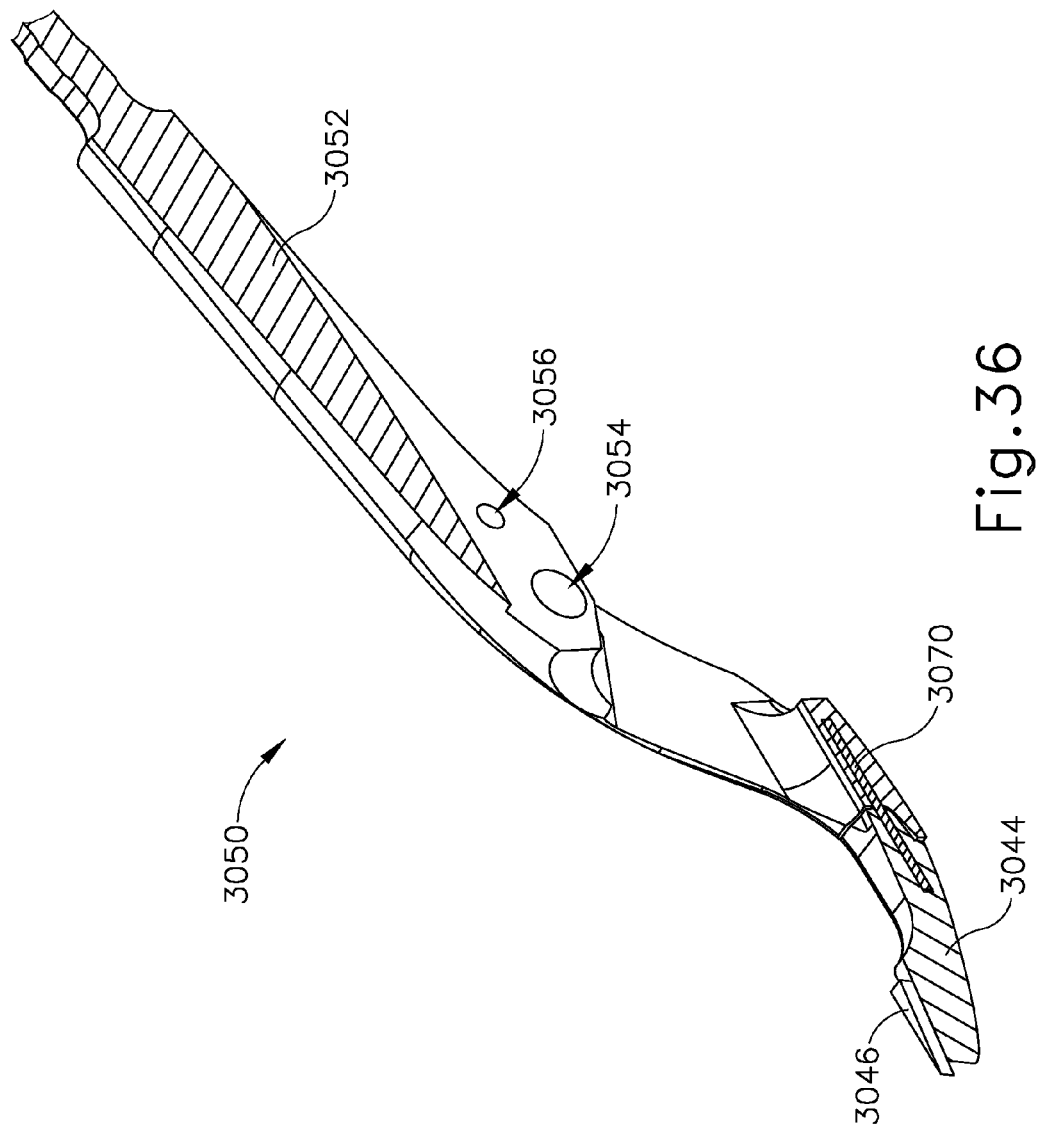
FIG. 36 depicts a perspective cross-sectional view of an exemplary clamp arm for use with the shaft assembly of FIG. 35.

FIGS. 35-36 show an exemplary shaft assembly (3030) and clamp arm assembly (3050) that may provide an operator with tactile feedback to inform the operator when the end effector is transitioning from a distal engagement state to a full length engagement state. It should be understood that shaft assembly (3030) and clamp arm assembly (3050) may be readily incorporated into instrument (100) in place of shaft assembly (130) and clamp arm assembly (150). As shown in FIG. 35, shaft assembly (3030) of this example comprises an outer sheath (3032) and a cap (3034). An ultrasonic blade (3042) extends distally from shaft assembly (3030). An engagement fin (3000) extends transversely from sheath (3032). Fin (3000) includes a recess (3002) that is configured to receive a coil spring (3004) and a detent member (3010). Detent member (3010) comprises a shaft (3012) and a ball (3014). Recess (3002) is configured such that detent member (3010) may be at least partially disposed in recess (3002), with a portion of ball (3014) protruding out from recess (3002). Coil spring (3004) resiliently biases ball (3014) outwardly, though fin (3000) retains detent member (3010) in recess (3002). Fin (3000) also includes a pivot opening (3008).

As shown in FIG. 36, clamp arm assembly (3050) of this example comprises a shank (3052), a clamp arm (3044), and a clamp pad (2046). Clamp arm (3044) is secured to shank (3052) via a leaf spring (3070). Clamp arm assembly (3050) is thus substantially similar to the example shown in FIGS. 7-9C and described above. Shank (3052) includes a pivot opening (3054) that is configured to align with pivot opening (3008) of fin (3000). Clamp arm assembly (3050) may thus be pivotally coupled with shaft assembly (3030) by a pin inserted through aligned openings (3008, 3054). Shank (3052) of the present example also includes a recess (3056).

When clamp arm assembly (3050) and shaft assembly (3030) are pivotally coupled together, clamp arm assembly (3050) may move through a first range of pivotal motion relative to shaft assembly (3030), where ball (3014) does not engage any portion of clamp arm assembly (3050). However, once clamp arm assembly (3050) completes the first range of pivotal motion relative to shaft assembly (3030), ball (3014) engages shank (3052) at an edge near recess (3056). It should be understood that the operator may feel this engagement in the form of increased resistance to further pivoting of clamp arm assembly (3050). This increased resistance may be provided by friction between resiliently biased ball (3014) and shank (3050). The operator may nevertheless continue pivoting clamp arm assembly (3050) through a second range of pivotal motion relative to shaft assembly (3030), until ball (3014) reaches recess (3056). At this point, ball (3014) may pop into recess (3056), which the operator may feel as tactile feedback. In some versions, the operator may continue to pivot clamp arm assembly (3050) through a second range of pivotal motion relative to shaft assembly (3030). In some other versions, the engagement of ball (3014) in recess (3056) indicates that the clamp arm assembly (3050) either cannot be pivoted further relative to shaft assembly (3030) or should not be pivoted further relative to shaft assembly (3030).

As indicated above, ball (3104) may provide tactile feedback associated with a completion of a first range of pivotal movement and completion of a second range of pivotal movement. In some versions, the first range of pivotal movement is associated with a first stage where only the distal portion of clamp pad (3046) engages blade (3042) (or only the distal portion of clamp pad (3046) compresses tissue against blade (3042)); while the second range of pivotal movement is associated with a second stage where the full length of clamp pad (3046) engages blade (3042) (or the full length of clamp pad (3046) compresses tissue against blade (3042)). Thus, ball (3014) engages shank (3052) to provide tactile feedback indicating a transition from a distal engagement state to a full length engagement state. It should be understood that recess (3056) may be omitted in some such versions.

In some other versions, clamp pad (3046) is not compressing tissue during the first range of pivotal movement. Instead, the second range of pivotal movement is associated with a stage where only the distal portion of clamp pad (3046) engages blade (3042) (or only the distal portion of clamp pad (3046) compresses tissue against blade (3042)); while the third range of pivotal movement is associated with a second stage where the full length of clamp pad (3046) engages blade (3042) (or the full length of clamp pad (3046) compresses tissue against blade (3042)). Thus, ball (3014) engages shank (3052) to provide tactile feedback indicating the beginning of a distal engagement state; and ball (3014) engages recess (3056) to provide tactile feedback indicating the transition to a full length engagement state.

Figure 37:
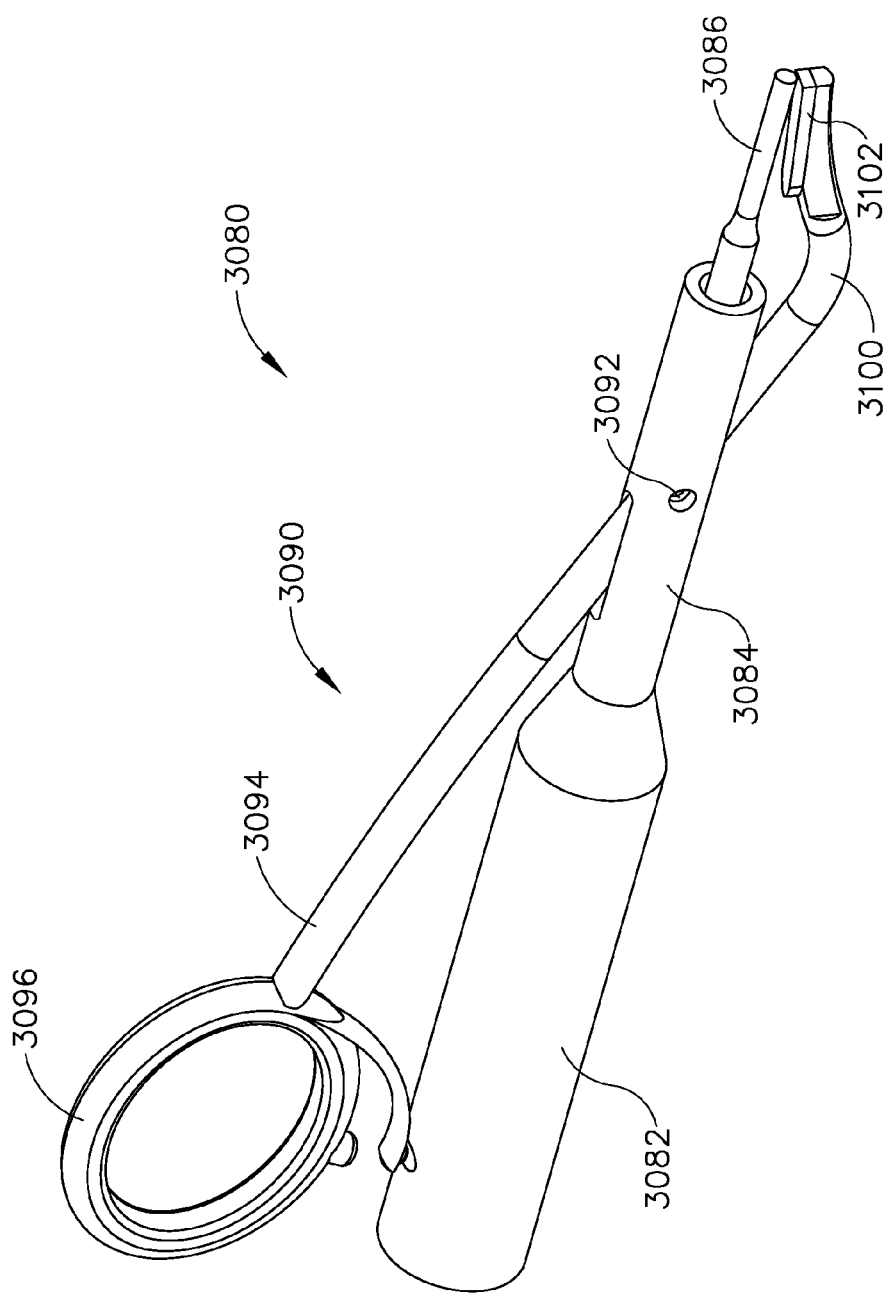
FIG. 37 depicts a perspective view of an exemplary alternative ultrasonic surgical instrument with another tactile feedback feature.
Figure 38A:
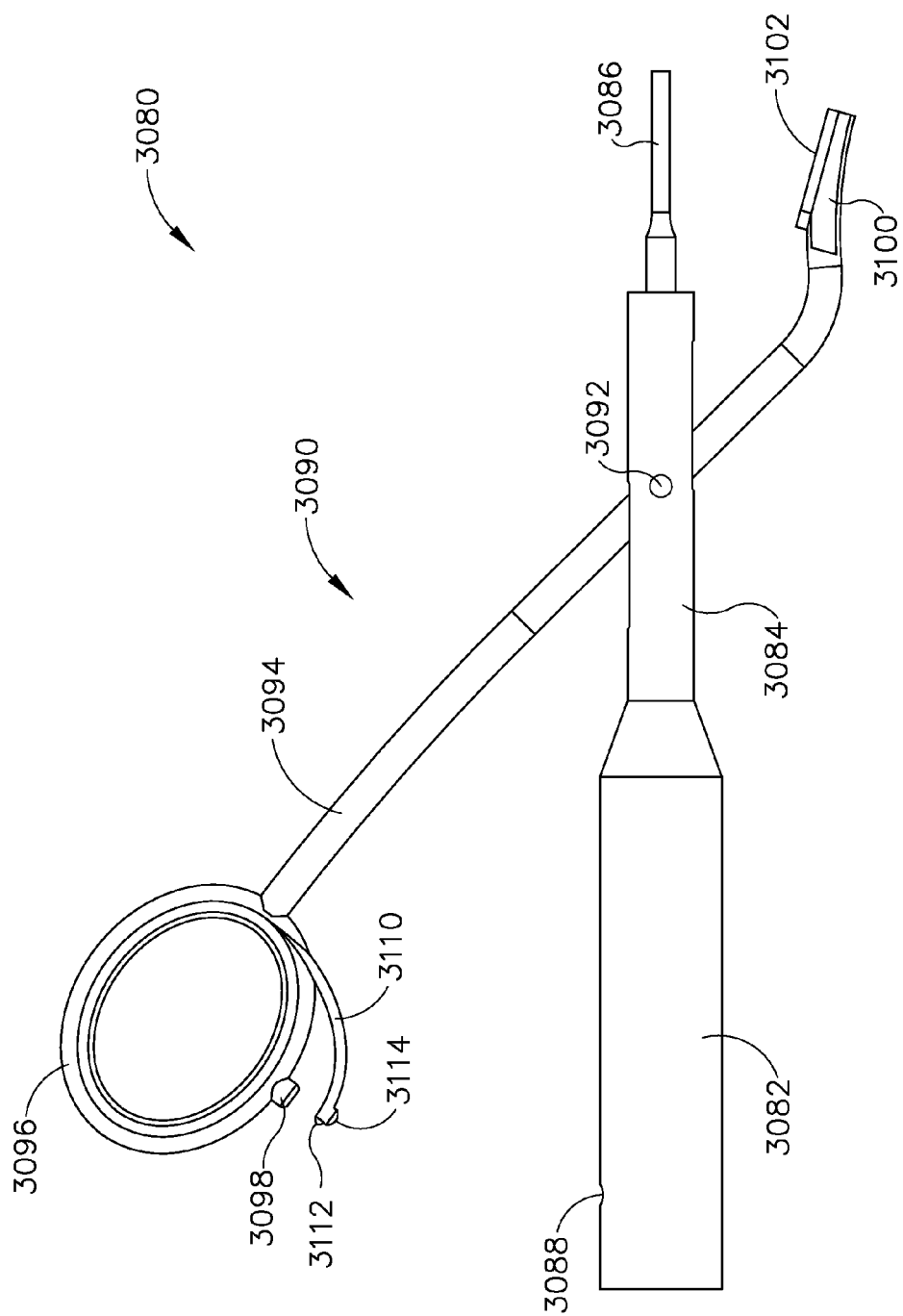
FIG. 38A depicts a side elevational view of the instrument of FIG. 37, with the clamp arm in an open position.
Figure 38B:
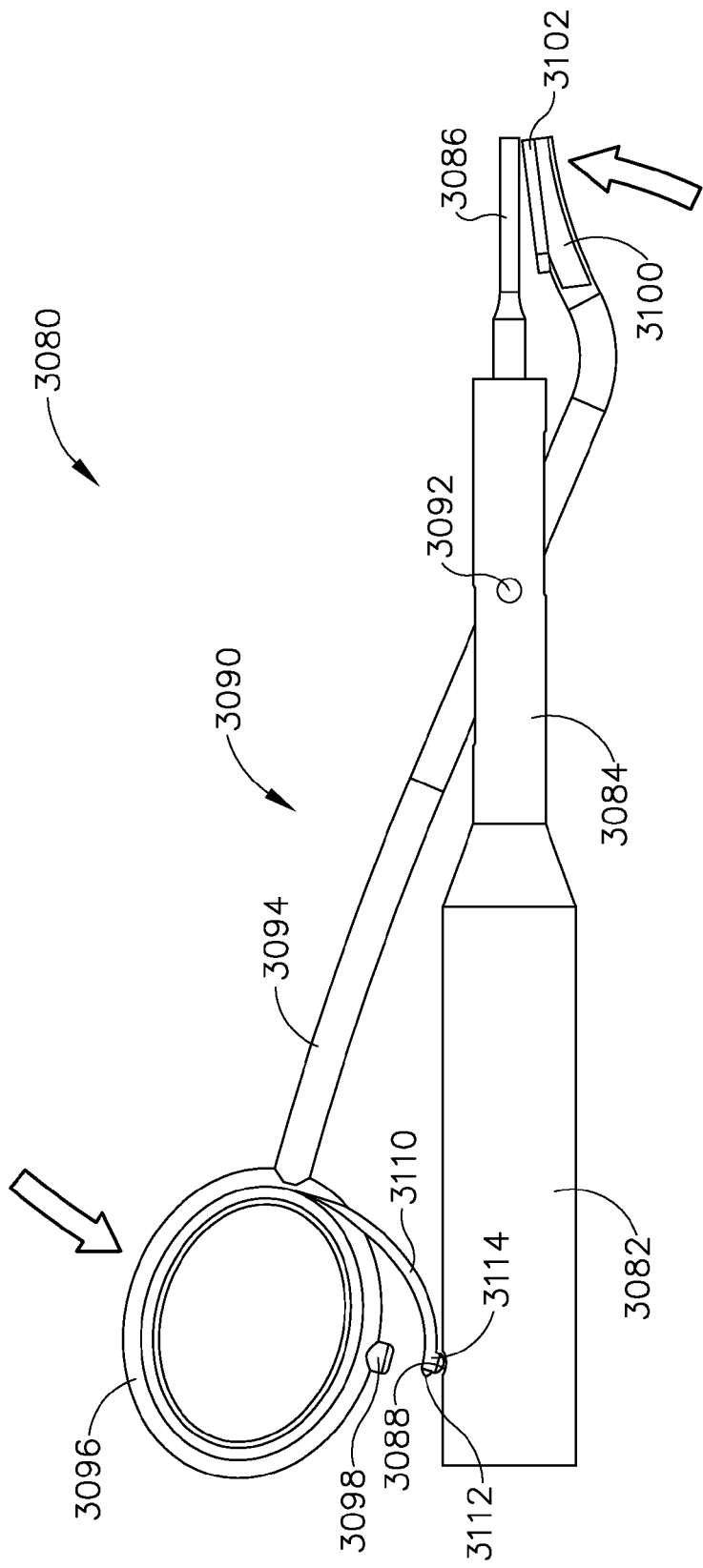
FIG. 38B depicts a side elevational view of the instrument of FIG. 37, with the clamp arm at a first stage of closure.
Figure 38C:
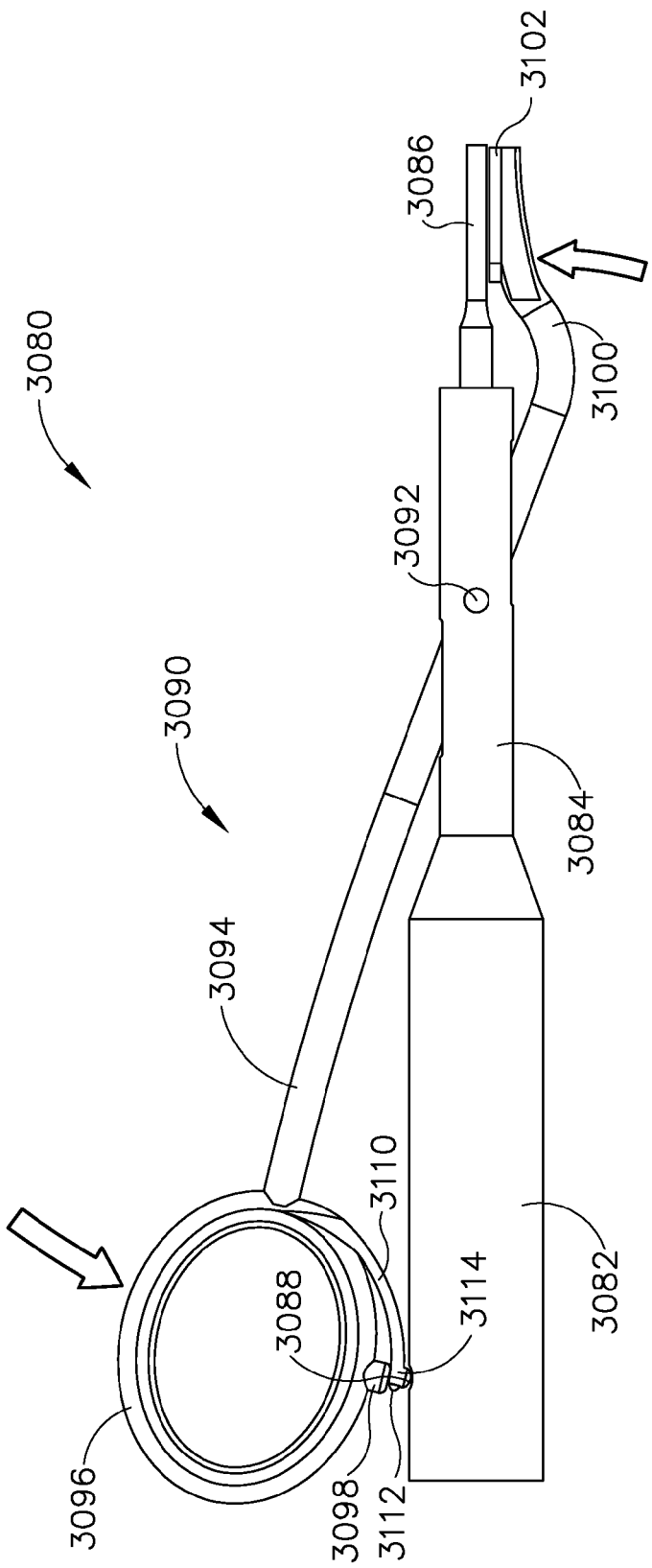
FIG. 38C depicts a side elevational view of the instrument of FIG. 37, with the clamp arm at a second stage of closure.

FIGS. 37-38C show another exemplary ultrasonic surgical instrument (3080) that is configured to provide tactile feedback indicating a transition from a first stage of clamp arm closure to a second stage of clamp arm closure. Instrument (3080) of this example is substantially similar to instrument (100) described above, in that instrument (3080) of this example comprises a body (3082), a shaft assembly (3084), an ultrasonic blade (3086), and a clamp arm assembly (3090). It should be understood that body (3082) may receive an ultrasonic transducer assembly (e.g., similar to transducer assembly (112), etc.), which may be operable to provide ultrasonic vibration of blade (3086). Similarly, body (3082) may include a finger grip ring (e.g., similar to finger grip ring (124), etc.), buttons (e.g., similar to buttons (126), etc.), and/or various other features.

Clamp arm assembly (3090) is pivotably coupled with shaft assembly (3084) via a pin (3092). Clamp arm assembly (3090) includes a shank (3094) with a thumb grip ring (3096), proximal to pin (3092). Clamp arm assembly (3090) also includes a clamp arm (3100) having a clamp pad (3102), distal to pin (3092). Shank (3094) and clamp arm (3100) are unitarily secured together such that thumb grip ring (3096) and shank (3094) may be driven toward body (3082) about pin (3092) to drive clamp pad (3102) toward ultrasonic blade (3086) to thereby compress tissue between clamp pad (3102) and ultrasonic blade (3086). As in various other examples describe herein, clamp arm (3100) is configured such that only the distal end of clamp pad (3102) will compress tissue against ultrasonic blade (3086) during a first stage of closure. In the event that clamp arm assembly (3090) is driven through a second stage of closure, clamp arm (3100) will deform such that the remaining length of clamp pad (3102) will also compress tissue against ultrasonic blade (3086).

Clamp arm assembly (3090) of the present example further comprises a feedback member (3110) extending from the proximal end of shank (3094), adjacent to thumb grip ring (3096). Feedback member (3110) of the present example is formed as a leaf spring that is resiliently biased to position a free end (3112) such that free end (3112) is spaced away from thumb grip ring (3096). In the present example, thumb grip ring (3096) includes a protrusion (3098) extending toward free end (3112). Similarly, free end (3112) includes a protrusion (3114) extending toward body (3082). Body (3082) includes a recess (3088) that is configured to receive protrusion (3114). As will be described in greater detail below, protrusions (3098, 3114) and recess (3088) cooperate to provide a detent feature. It should be understood that protrusions (3098, 3114) and recess (3088) are merely optional, such that protrusions (3098, 3114) and recess (3088) may be substituted, supplemented, or completely omitted, as desired.

FIGS. 38A-38C show various operational states of instrument (3080). In particular, FIG. 38A shows instrument (3080) in an open state, where clamp arm (3100) and clamp pad (3102) are spaced away from ultrasonic blade (3086). In this state, the operator may position instrument (3080) such that tissue is located between clamp pad (3102) and ultrasonic blade (3086). Once instrument (3080) is suitably positioned, the operator may drive thumb ring grip (3096) toward body (3082), thereby driving clamp pad (3102) toward ultrasonic blade (3086). At some point during this actuation, clamp pad (3102) will begin compressing the tissue against ultrasonic blade (3086). Clamp pad (3102) will eventually reach a position similar to that shown in FIG. 38B, which represents instrument (3080) in a state where clamp pad (3102) is at a first stage of closure. As can be seen, only the distal end of clamp pad (3102) would be compressing tissue against ultrasonic blade (3086) at this first stage of closure. It should be understood that the operator may encounter relatively low resistance to rotation of clamp arm assembly (3090) from the position shown in FIG. 38A to the position shown in FIG. 38B. Other than friction at pin (3092), the only resistance would be provided by tissue that is interposed between clamp pad (3102) and ultrasonic blade (3086).

As can be seen in FIG. 38B, free end (3112) of feedback member (3110) comes into contact with body (3082) once clamp arm assembly (3090) reaches the first stage of closure. In particular, protrusion (3114) is received in recess (3088). The operator may continue to drive thumb ring grip (3096) toward body (3082) to eventually reach a second stage of closure as shown in FIG. 38C. During the transition from the first stage of closure as shown in FIG. 38B to the second stage of closure as shown in FIG. 38C, clamp arm (3100) deforms such that the proximal portion of clamp pad (3102) eventually compresses tissue against ultrasonic blade (3086). It should be understood that any of the various features described herein may be used to provide the staged closure action of clamp pad (3102). Also during the transition from the first stage of closure as shown in FIG. 38B to the second stage of closure as shown in FIG. 38C, feedback member (3110) deforms, thereby providing additional resistance to further pivotal movement of clamp arm assembly (3090). It should therefore be understood that the operator may perceive a transition from the first stage of closure toward the second stage of closure through tactile feedback in the form of increased resistance provided by deformation of feedback member (3110). This increased resistance may be substantial and/or otherwise abrupt, providing a clear signal to the operator. Protrusion (3098) of thumb ring grip (3096) eventually engages feedback member (3110), providing a hard stop to indicate completion of the second stage of closure.

In some instances, the operator may wish to only complete the first stage of closure. Thus, as soon as the operator encounters the abrupt increase in resistance provided by feedback member (3110), the operator may release clamp arm assembly (3090). By way of example only, this may be the case when the operator only wishes to make a relatively small cut in tissue. Otherwise, the operator may continue to the second stage of closure and then release clamp arm assembly (3090).

It should be understood that feedback member (3110) may be varied, substituted, or supplemented in numerous ways. By way of example only, a buckling support may be added to shaft assembly (3084), thumb ring grip (3096), shank (3094), and/or some other feature of instrument (3080). Such a buckling support may buckle to indicate a transition from the first stage of closure toward the second stage of closure. As another merely illustrative example, shaft assembly (3084) may be configured such that recess (3088) is slightly undersized relative to protrusion (3114), such that recess (3088) and protrusion (3114) provide a detent assembly that provides a click or some other form of tactile and/or audible feedback to indicate a transition from the first stage of closure toward the second stage of closure. As yet another merely illustrative example, recess (3088) may be replaced with a buckling feature that buckles in response to application of force by protrusion (3114) upon reaching the transition from the first stage of closure toward the second stage of closure. Of course, feedback member (3110) may also be replaced with a compression/coil spring and/or some other form of resilient member. Similarly, feedback member (3110) may be replaced with a torsion spring that is positioned about pin (3092) and that is engaged upon reaching the transition from the first stage of closure toward the second stage of closure. Other suitable ways in which an instrument may provide tactile feedback to indicate a transition from a distal engagement state to a full length engagement state will be apparent to those of ordinary skill in the art in view of the teachings herein.

M. Exemplary Clamp Arm Stage Selection Features

Various exemplary end effectors described above provide staged engagement where the distal regions of the clamp pad and blade engage first, followed by the proximal regions of the clamp pad and blade. In some instances, it may be desirable to provide the operator with the ability to select between a distal engagement mode and a full length engagement mode. By way of example only, a distal engagement mode may provide only engagement between the distal regions of the clamp pad and blade, preventing engagement between the proximal regions of the clamp pad and blade. A full length engagement mode may provide only engagement between the full length of clamp pad and blade. In addition or in the alternative, the instrument may provide selection of a staged engagement mode, whereby the distal regions of the clamp pad and blade engage first, followed by the proximal regions of the clamp pad and blade. Various examples of how an instrument may provide mode selection will be described in greater detail below; while other examples will be apparent to those of ordinary skill in the art in view of the teachings herein.

Figure 39:
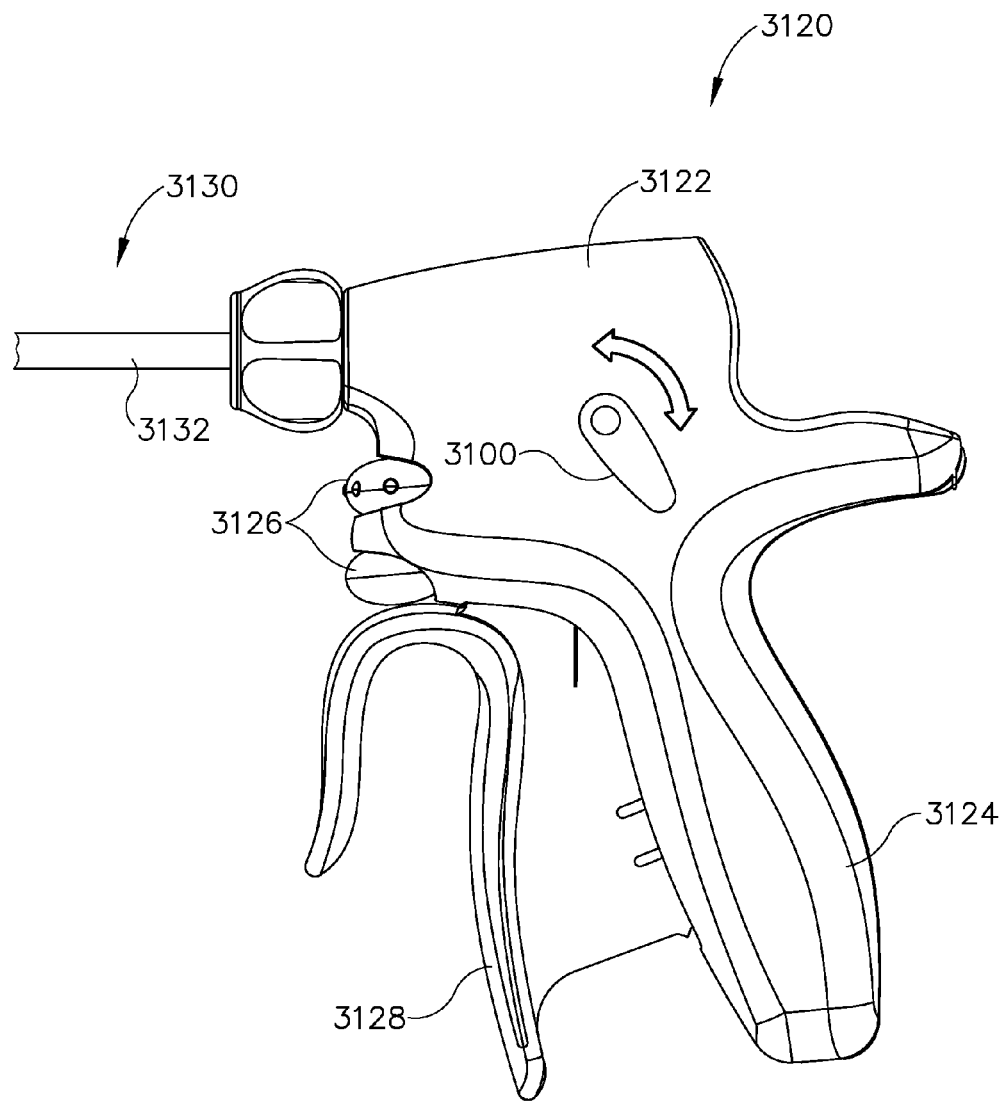
FIG. 39 depicts a side elevational view of an exemplary alternative handle assembly with a pivoting toggle switch for clamping mode selection.

FIG. 39 shows an exemplary alternative handle assembly (3120) that may be used as a substitute for handle assembly (20). Handle assembly (3120) of this example comprises a body (3122) including a pistol grip (3124) and a pair of buttons (3126). Handle assembly (3120) also includes a trigger (3128) that is pivotable toward and away from pistol grip (3124) to selectively drive a clamp arm toward and away from an ultrasonic blade as described herein. Handle assembly (3120) also includes a switch (3100) that is pivotally coupled with body (3122). Switch (3100) is pivotable to select a mode of operation for a clamp arm positioned at the distal end of shaft assembly (3130). By way of example only, switch (3100) may enable selection from a distal engagement mode, full engagement mode, and/or staged engagement mode. Switch (3100) may be coupled with a mechanical assembly that is operable to implement such stage selection by selectively restricting the distance to which trigger (3128) may pivot toward pistol grip (3124). Alternatively, switch (3100) may be coupled with a mechanical assembly that is operable to implement such stage selection by selectively restricting the distance to which an inner tube (not shown) may retract relative to outer sheath (3130). Various suitable ways in which switch (3100) may provide a mode selection for clamp arm actuation will be apparent to those of ordinary skill in the art in view of the teachings herein.

Figure 40:
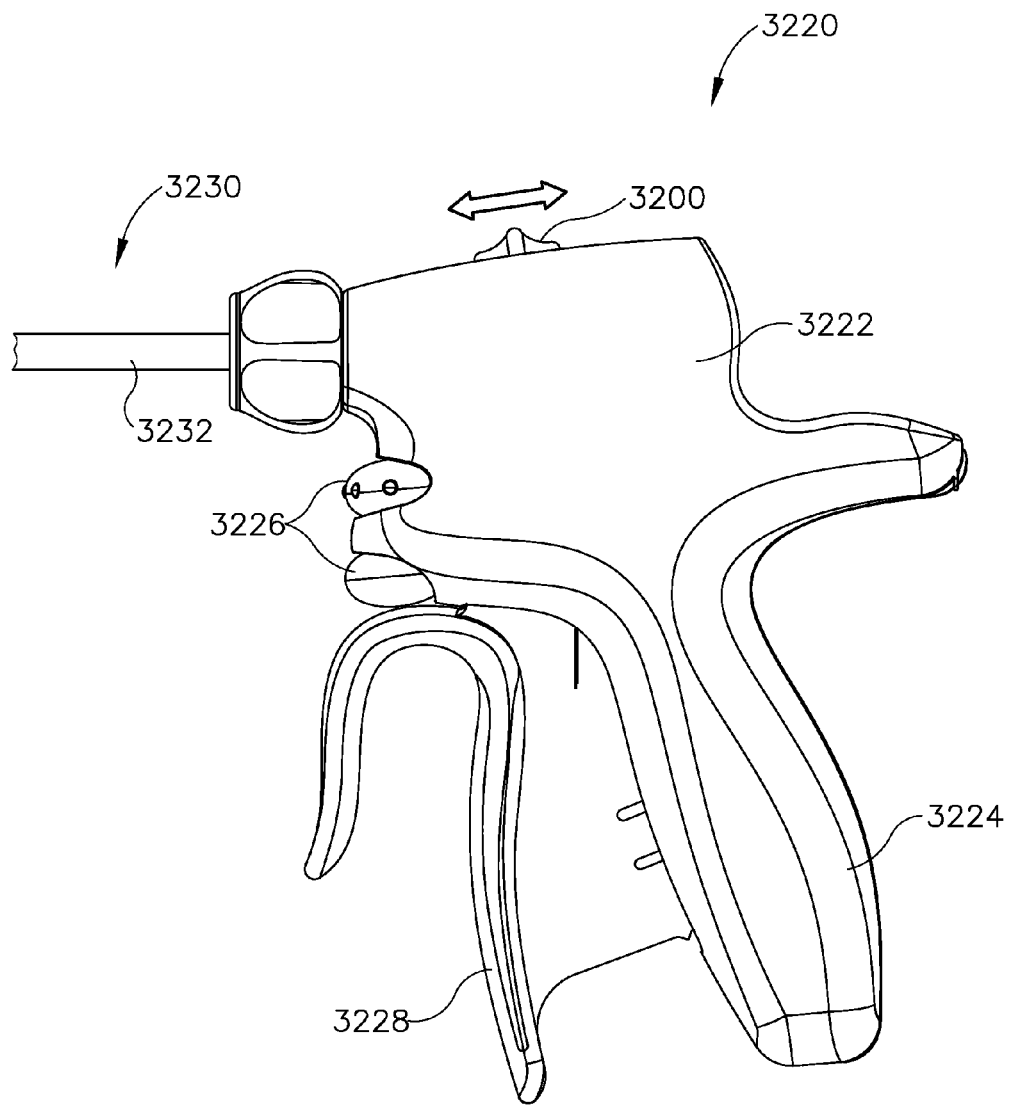
FIG. 40 depicts a side elevational view of an exemplary alternative handle assembly with a sliding toggle switch for clamping mode selection

FIG. 40 shows another exemplary alternative handle assembly (3220) that may be used as a substitute for handle assembly (20). Handle assembly (3220) of this example comprises a body (3222) including a pistol grip (3224) and a pair of buttons (3226). Handle assembly (3220) also includes a trigger (3228) that is pivotable toward and away from pistol grip (3224) to selectively drive a clamp arm toward and away from an ultrasonic blade as described herein. Handle assembly (3220) also includes a switch (3200) that is slidably coupled with body (3222). Switch (3200) is pivotable to select a mode of operation for a clamp arm positioned at the distal end of shaft assembly (3230). By way of example only, switch (3200) may enable selection from a distal engagement mode, full engagement mode, and/or staged engagement mode. Switch (3200) may be coupled with a mechanical assembly that is operable to implement such stage selection by selectively restricting the distance to which trigger (3228) may pivot toward pistol grip (3224). Alternatively, switch (3200) may be coupled with a mechanical assembly that is operable to implement such stage selection by selectively restricting the distance to which an inner tube (not shown) may retract relative to outer sheath (3230). Various suitable ways in which switch (3200) may provide a mode selection for clamp arm actuation will be apparent to those of ordinary skill in the art in view of the teachings herein.

Figure 41A:
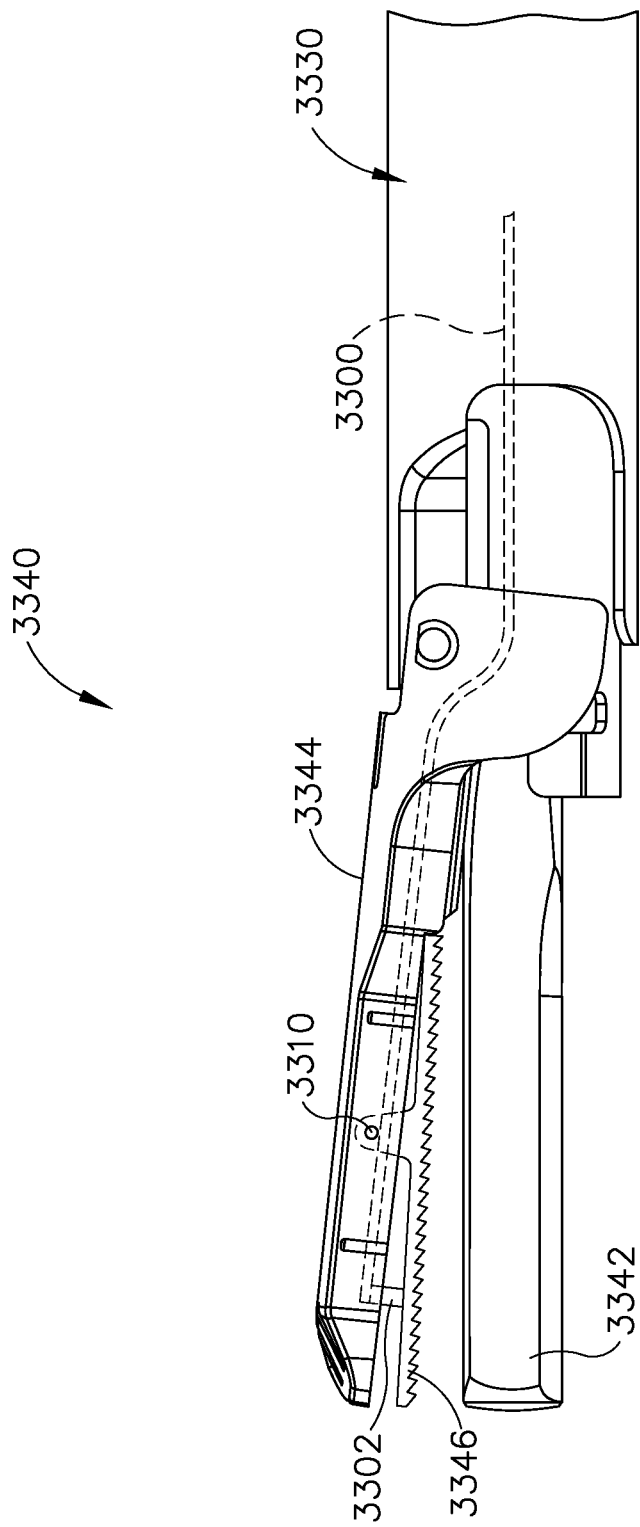
FIG. 41A depicts a side elevational view of an exemplary alternative end effector with a clamping mode selection beam in a distal position.
Figure 41B:
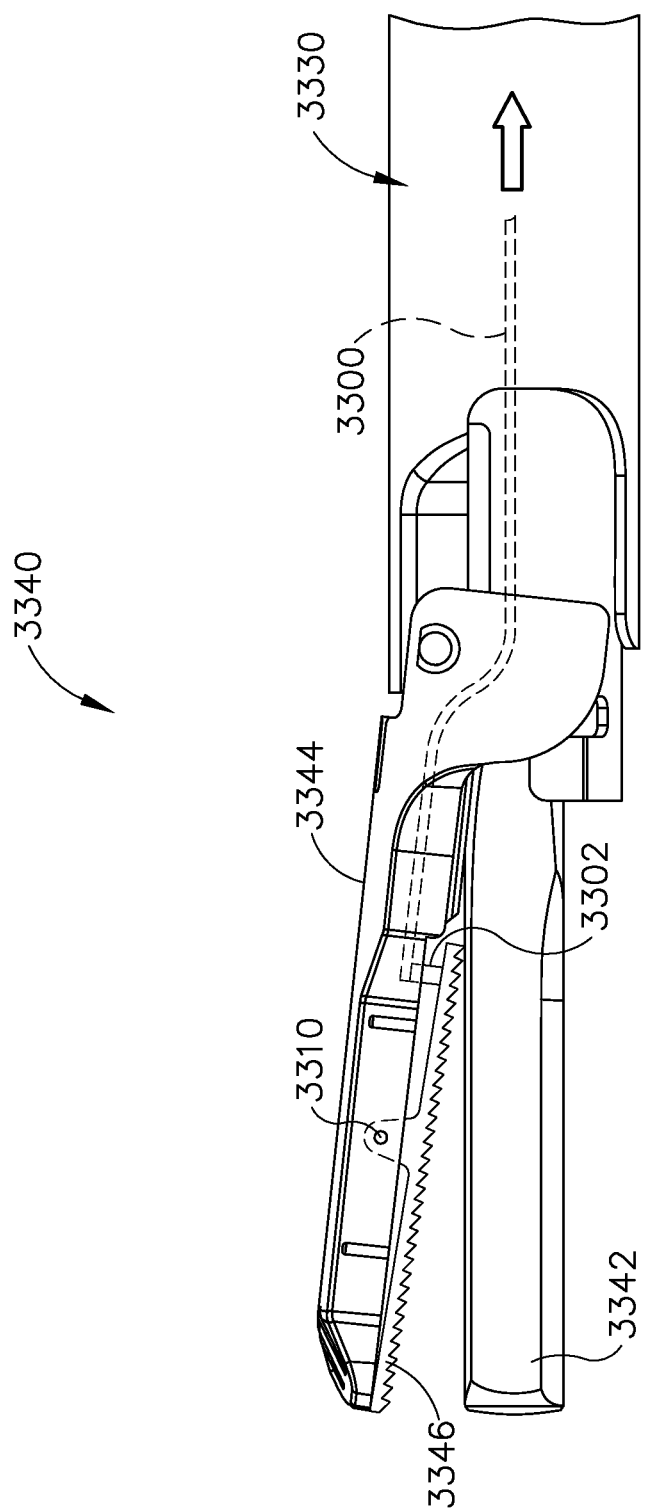
FIG. 41B depicts a side elevational view of the end effector of FIG. 41A, with the clamping mode selection beam in a proximal position.

FIGS. 41A-41B show one merely illustrative example of how mode selection for clamp arm actuation may be provided. In particular, FIGS. 41A-41B show an exemplary end effector (3340) that is substantially similar to end effector (2340) described above. End effector (3340) of this example comprises an ultrasonic blade (3342), a clamp arm (3344), and a clamp pad (3346). Clamp pad (3346) is pivotally coupled with clamp arm (3344) by a pin (3310). A push wire (3300) is sildably disposed in a shaft assembly (3330) and extends into clamp arm (3344). Push wire (3300) is movable between a distal position as shown in FIG. 41A and a proximal position as shown in FIG. 41B. The distal end of push wire (3300) includes a transversely extending localized pressure feature (3302) that is configured to bear against clamp pad (3346). Thus, when push wire (3300) is in the distal position, localized pressure feature (3302) bears against the distal portion of clamp pad (3346), causing clamp pad (3346) to be pivotally oriented about pin (3310) as shown in FIG. 41A. When push wire (3300) is in the proximal position, localized pressure feature (3302) bears against the proximal portion of clamp pad (3346), causing clamp pad (3346) to be pivotally oriented about pin (3310) as shown in FIG. 41B.

With clamp pad (3346) in the orientation shown in FIG. 41A, end effector (3340) is in a distal engagement mode. When clamp pad (3346) in the orientation shown in FIG. 41B, end effector (3340) is in a full engagement mode. It should therefore be understood that the mode of end effector (3340) may be based on the longitudinal position of push wire (3300) relative to end effector (3340). It should also be understood that push wire (3300) may be readily coupled with a user input feature such as switches (3100, 3200) and/or any other suitable components.

Figure 42:
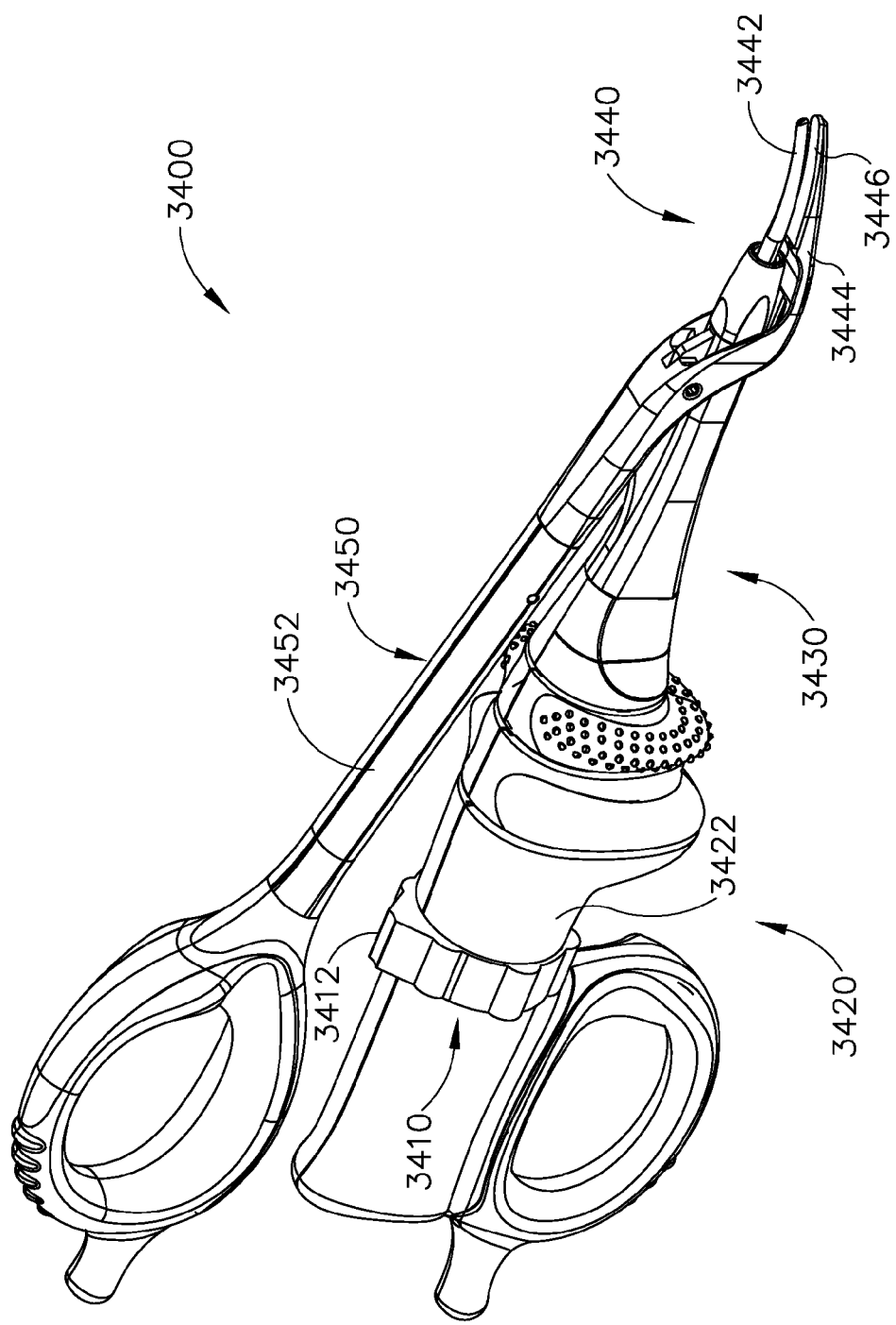
FIG. 42 depicts a perspective view of the instrument of FIG. 4 with an exemplary clamping mode selection ring secured to the body of the handle assembly.
Figure 43:
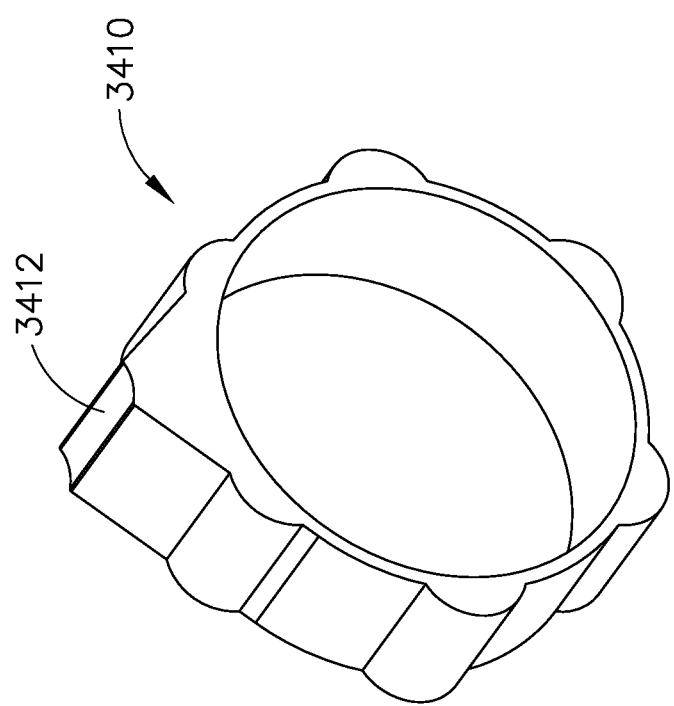
FIG. 43 depicts a perspective view of the clamping mode selection ring of FIG. 42.

FIGS. 42-43 show another merely illustrative example of how mode selection for clamp arm actuation may be provided. In particular, FIG. 42 shows an exemplary instrument (3400) that is substantially similar to instrument (100) in that instrument (3400) has a handle assembly (3420), a shaft assembly (3430), an end effector (3440), and a clamp arm assembly (3450). End effector (3440) comprises an ultrasonic blade (3442) and a clamp arm (3444) with a clamp pad (3446). End effector (3440) is configured to provide staged engagement between clamp pad (3446) and blade (3442), such that the distal regions of clamp pad (3446) and blade (3442) engage first; then the proximal regions of clamp pad (3446) and blade (3442). End effector (3440) may be configured in accordance with any of the various teachings herein in order to provide such staged engagement.

Clamp arm assembly (3450) is pivotable relative to shaft assembly (3450) through a first range of motion to provide distal engagement between clamp pad (3446) and blade (3442). After completing this first range of motion, clamp arm assembly (3450) is pivotable relative to shaft assembly (3430) through a second range of motion to provide full engagement between clamp pad (3446) and blade (3442). Instrument (3400) of the present example further comprises a stop ring (3410) that is operable to arrest pivotal movement of clamp arm assembly (3450) after clamp arm assembly (3450) completes the first range of motion. Stop ring (3410) is rotatably positioned about the body (3422) of handle assembly (3420) to selectively position a stop feature (3412) in relation to shank (3452) of clamp arm assembly (3450). FIG. 43 shows stop ring (3410) in greater detail. FIG. 42 shows stop ring (3410) oriented such that stop feature (3412) will engage shank (3452) after clamp arm assembly (3450) completes the first range of motion. Stop feature (3412) will thus prevent clamp arm assembly (3450) from pivoting through the second range of motion. It should therefore be understood that stop ring (3410) effects a selection fo distal engagement mode when stop ring (3410) is at this angular orientation about body (3422) of handle assembly. In order to provide full engagement mode, the operator may simply rotate stop ring (3410) about body (3422) such that stop feature (3412) will no longer arrested pivotal movement of clamp arm assembly (3450). Clamp arm assembly (3450) may thus pivot through both the first and second ranges of motion when stop ring (3410) is rotated to provide a full engagement mode.

Figure 44A:
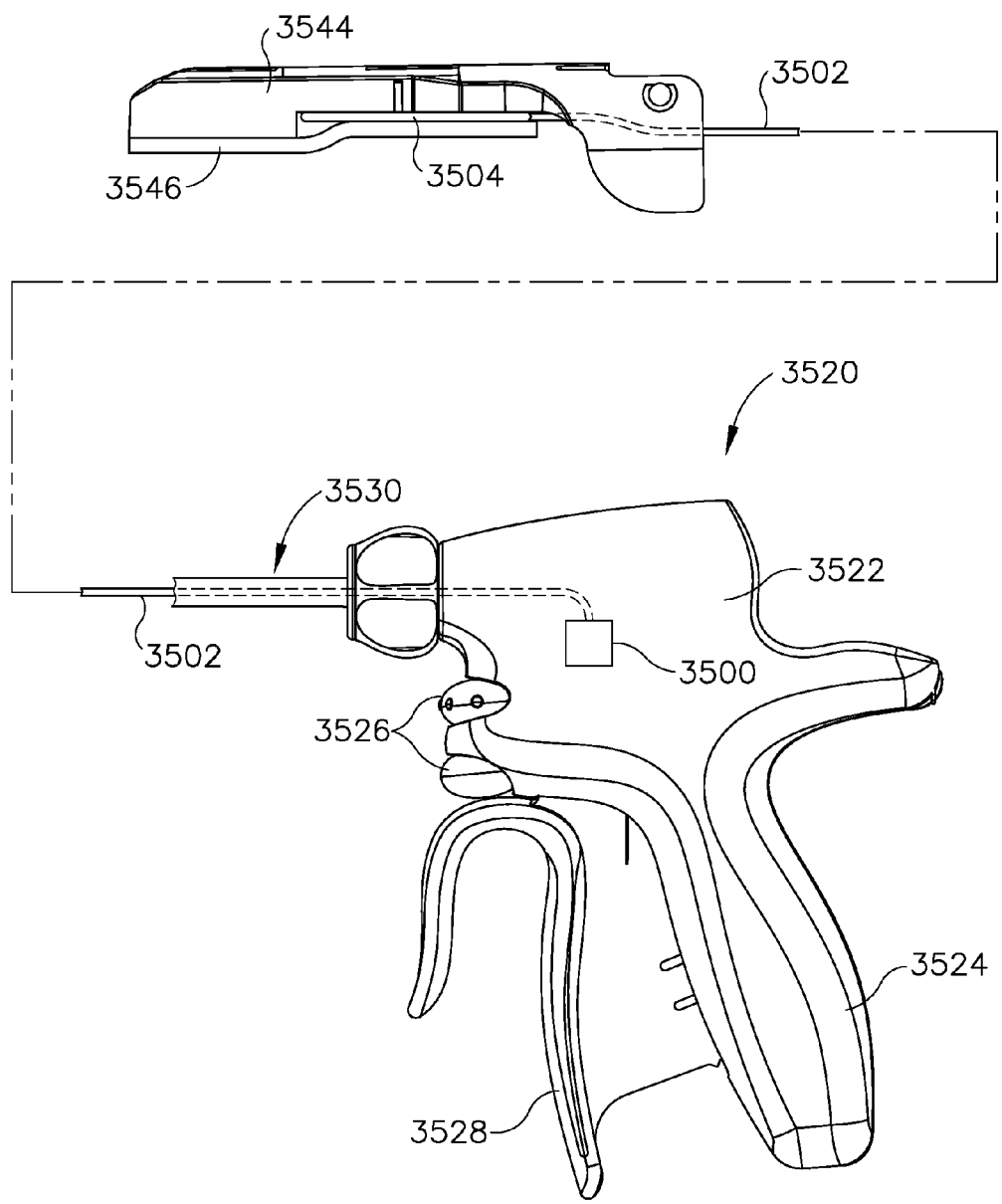
FIG. 44A depicts an exemplary alternative handle assembly and clamp arm assembly, with a clamp arm bladder in a deflated state.
Figure 44B:
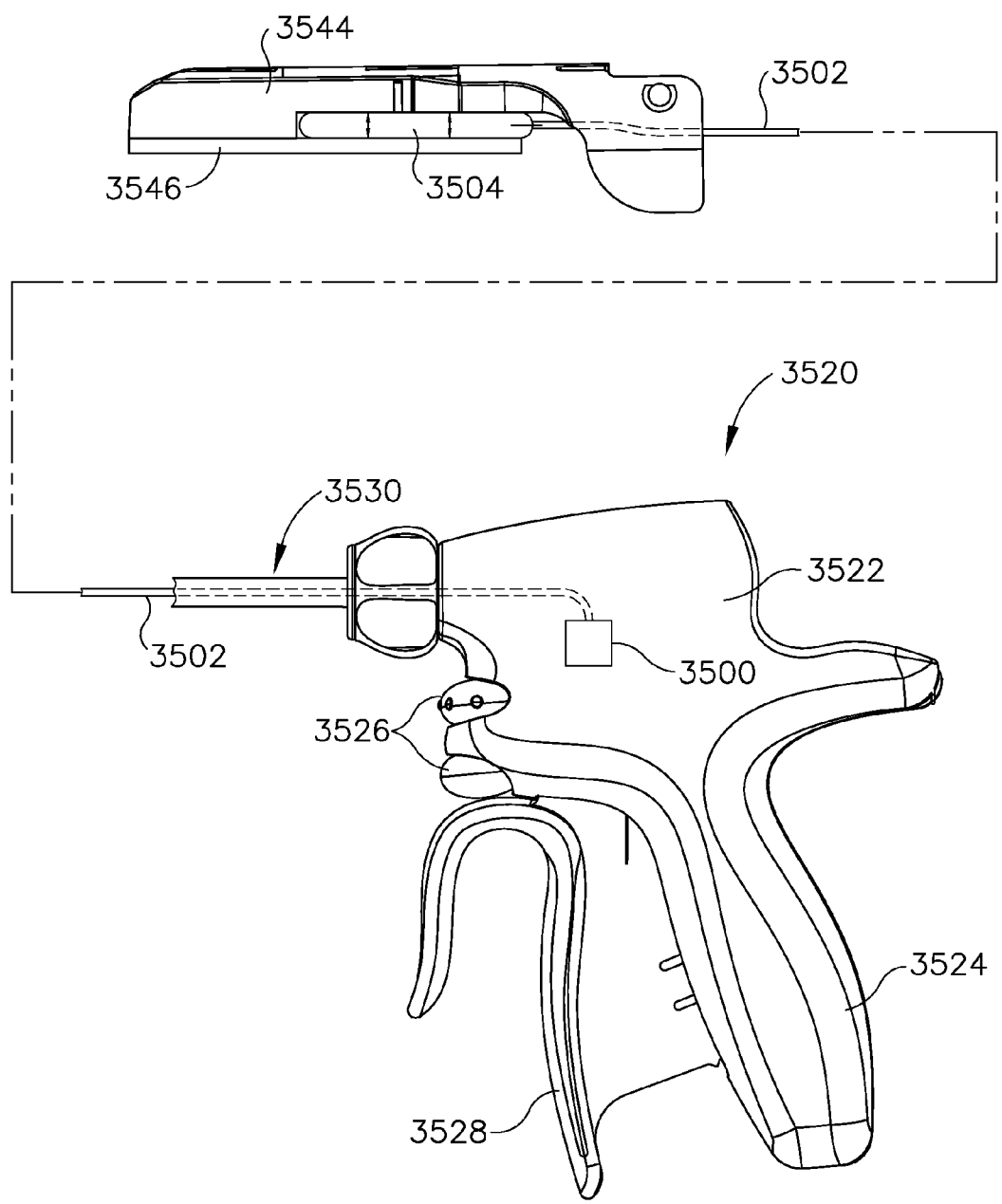
FIG. 44B depicts the handle assembly and clamp arm assembly of FIG. 44A, with the clamp arm bladder in an inflated state.

FIGS. 44A-44B show yet another merely illustrative example of how mode selection for clamp arm actuation may be provided. In particular, FIGS. 44A-44B show an exemplary alternative handle assembly (3520) that may be used as a substitute for handle assembly (20). Handle assembly (3520) of this example comprises a body (3522) including a pistol grip (3524) and a pair of buttons (3526). Handle assembly (3520) also includes a trigger (3528) that is pivotable toward and away from pistol grip (3524) to selectively drive a clamp arm (3544) toward and away from an ultrasonic blade as described herein. Handle assembly (3520) also includes a fluid reservoir (3500) and a fluid conduit (3502) extending from the fluid reservoir (3500). Conduit (3502) extends further through shaft assembly (3530) to a bladder (3504), which is positioned in clamp arm (3544). In particular, bladder (3504) is positioned between a proximal portion of clamp arm (3544) and a proximal portion of a clamp pad (3546). The distal portion of clamp pad (3546) is directly secured to the distal portion of clamp arm (3544). Clamp pad (3546) is flexible such that clamp pad (3546) may transition from a distal engagement mode configuration (FIG. 44A) to a full engagement mode configuration (FIG. 44B).

Reservoir (3500), conduit (3502), and bladder (3504) form a closed fluid circuit. By way of example only, reservoir (3500) may comprise a bellows assembly, a silicone bulb, a proximal length of conduit (3502), and/or any other suitable kind of structure as will be apparent to those of ordinary skill in the art in view of the teachings herein. Handle assembly (3520) is configured such that trigger (3528) compresses reservoir (3500) when trigger (3528) is pivoted toward pistol grip (3524). This compression of reservoir (3500) drives a fluid (e.g., saline) from reservoir (3500) to bladder (3504), causing bladder (3504) to expand. This expansion of bladder (3504) drives the proximal portion of clamp pad (3546) away from the proximal portion of clamp arm (3544), as shown in FIG. 44B. In some versions, clamp pad (3546) is resiliently biased to assume the configuration shown in FIG. 44A, such that after the operator relaxes their grip on trigger (3528), the resilience of clamp pad (3546) drives the fluid from bladder (3504) back to reservoir (3500), allowing clamp pad (3546) to return to the configuration shown in FIG. 44A.

In the present example, trigger (3528) is pivotable toward pistol grip (3524) through a first range of motion where clamp pad (3546) is configured as shown in FIG. 44A. Trigger (3528) does not engage reservoir (3500) during this first range of motion. In other words, handle assembly (3520) and clamp pad (3546) provide a distal engagement mode while trigger (3528) pivots through the first range of motion. As trigger (3538) continues to pivot toward pistol grip (3524) through a second range of motion, trigger (3528) engages reservoir (3500) to drive the fluid into bladder (3504) as shown in FIG. 44B. Handle assembly (3520) and clamp pad (3546) thus provide a full engagement mode while trigger (3528) pivots through the second range of motion. It should be understood that the operator may encounter increased resistance from reservoir (3500) against further pivotal motion of trigger (3528) as soon as trigger (3528) completes the first range of motion. This increase in resistance may thus provide tactile feedback to the operator, indicating a transition from the distal engagement mode to the full engagement mode.

In some other versions, reservoir (3500) is actuated through a separate input feature. In some such versions, handle assembly (3520) and clamp pad (3546) selectively provide either a distal engagement mode or a full engagement mode throughout the full range of pivotal motion of trigger (3528) toward pistol grip (3524), based on a mode selection made through the separate input feature.

In still other variations, the distance between a portion of a flexible clamp pad and a corresponding portion of a clamp arm is adjustable by use of a variation of push wire (3300) that includes a shim or mandrel feature. Such a shim or mandrel feature may operate similar to bladder (3504) described above. In particular, the shim or mandrel feature may serve as a cam that selectively drives a portion of the clamp pad away from the clamp arm. For instance, the shim or mandrel feature may be distally positioned between a proximal portion of the clamp pad and a proximal portion of the clamp arm to provide a full engagement mode. The shim or mandrel feature may then be proximally positioned, such that the shim or mandrel feature is no longer positioned between the proximal portion of the clamp pad and the proximal portion of the clamp arm, to provide a full engagement mode. Other suitable ways in which portions of a clamp pad may be selectively positioned in relation to a clamp arm to provide engagement mode selection will be apparent to those of ordinary skill in the art in view of the teachings herein.

In any of the staged engagement examples described above, it should be understood that generator (16, 116) may adjust the power profile for activation of the ultrasonic blade based on whether the end effector is in distal engagement mode or full engagement mode. For instance, the instrument may include one or more sensors that are configured to detect the engagement mode. Generator (16, 116) may be in communication with such one or more sensors. Alternatively, in versions where the instrument provides manual selection between a distal engagement mode or a full engagement mode, generator (16, 116) may detect the mode based on the state of the feature that is used to provide the manual selection of mode.

III. Miscellaneous

In addition to or as an alternative to using staged clamping to reduce heat in a version of instrument (10, 100), a fluid may be used to cool blade (42, 142). For instance, a cooling liquid (e.g., saline, etc.) may be applied to the proximal end of blade (42, 142). The cooling fluid may then be communicated distally along the rest of the length of blade (42, 142) to thereby cool blade. The ultrasonic vibration of blade (42, 142) may provide such distal communication of the fluid. In some such versions, a particular vibrational scheme may be used to drive liquid distally along blade (42, 142). Such a particular, vibrational scheme may have no meaningful effect on tissue that is in contact with blade (42, 142) while blade is being driven in such a fashion. For instance, blade (42, 142) may be vibrated in short pulses (e.g., of approximately 10 to 20 millisecond duration) of low amplitude motion to drive the liquid distally along blade (42, 142). In some such instances, generator (16, 116) is programmed to provide such liquid driving ultrasonic activation of blade (42, 142) when the operator is not pressing any buttons (26, 126). In addition or in the alternative, generator (16, 116) may be programmed to provide liquid driving ultrasonic activation of blade (42, 142) when generator (16, 116) detects that blade (42, 142) is not contacting tissue. As yet another merely illustrative example, instrument (10, 100) may include a separate user input feature that is operable to manually trigger a liquid driving vibrational scheme. Other suitable ways in which a liquid driving vibrational scheme may be triggered will be apparent to those of ordinary skill in the art in view of the teachings herein.

In some other versions, the same vibrational movement that is used to drive blade during tissue cutting/sealing may drive liquid distally along blade (42, 142). As yet another merely illustrative example, fluid may be communicated to and/or along blade in accordance with at least some of the teachings of U.S. Pub. No. 2011/0152759, entitled "Use of Biomarkers and Therapeutic Agents with Surgical Devices," published Jun. 23, 2011, issued as U.S. Pat. No. 8,591,459 on Nov. 26, 2013, the disclosure of which is incorporated by reference herein. It should be understood that the teachings in U.S. Pub. No. 2011/0152759, issued as U.S. Pat. No. 8,591,459 on Nov. 26, 2013, relating to dispensation of medical fluids may be readily adapted to provide communication of cooling fluid. Additional examples of ways in which fluid may be used to cool blade (42, 142) are described in U.S. patent application Ser. No. 14/552,530, entitled "Features to Apply Fluid to an Ultrasonic Blade of a Surgical Instrument," filed on Nov. 25, 2014, published as U.S. Pat. Pub. No. 2015/0148832 on May 28, 2015, the disclosure of which is incorporated by reference herein; U.S. patent application Ser. No. 14/553,329, entitled "Features to Drive Fluid toward an Ultrasonic Blade of a Surgical Instrument," filed on Nov. 25, 2014, published as U.S. Pat. Pub. No. 2016/0143658, the disclosure of which is incorporated by reference herein; U.S. patent application Ser. No. 14/553,142, entitled "Features for Communication of Fluid through Shaft Assembly of Ultrasonic Surgical Instrument," filed on Nov. 25, 2014, published as U.S. Pat. Pub. No. 2016/0143657 on May 26, 2016, the disclosure of which is incorporated by reference herein; and U.S. patent application Ser. No. 14/553,378, entitled "Ultrasonic Surgical Instrument with Blade Cooling through Retraction," filed on Nov. 25, 2014, published as U.S. Pat. Pub. No. 2016/0143659 on May 26, 2016, the disclosure of which is incorporated by reference herein. It should be understood that the teachings herein may be readily combined with the teachings of those references and the various other references cited herein. Other examples will be apparent to those of ordinary skill in the art in view of the teachings herein.

In addition to or as an alternative to using fluid to reduce heat in a version of instrument (10, 100), one or more shielding features may be used to avoid direct contact between a hot portion of instrument (10, 100) and tissue (or other structures). A gap may be defined between the shielding feature and the corresponding hot portion of instrument (10, 100), to avoid or minimize communication of heat from the hot portion of instrument (10, 100) and the shielding feature. Such a gap may be filled with liquid, air or some other gas, a solid insulating material, and/or any other suitable kind of filler, including combinations thereof. It should also be understood that various kinds of structural features may be interposed between the hot portion of instrument (10, 100) and the shielding feature, including but not limited to a roughened surface, grooves, dimples, pimples, nubs, knurling, a honeycomb structure, etc. Such structural features may minimize transfer of heat from the hot portion of instrument (10, 100) and the shielding feature. Similarly, a shielding feature (and/or a hot feature of instrument (10, 100)) may include external surface structures such as a roughened surface, grooves, dimples, pimples, nubs, knurling, a honeycomb structure, etc., to minimize transfer of heat from the shielding feature (or hot feature) to adjacent tissue, etc. Various merely illustrative examples of shielding features are described in U.S. Provisional Patent App. No. 61/908,920, the disclosure of which is incorporated by reference herein; and also in U.S. patent application Ser. No. 14/552,552, entitled "Shielding Features for Ultrasonic Blade of a Surgical Instrument," filed on Nov. 25, 2014, published as U.S. Pat. Pub. No. 2015/0148833 on May 28, 2015, the disclosure of which is incorporated by reference herein; and also in U.S. patent application Ser. No. 14/552,681, entitled "Sleeve Features for Ultrasonic Blade of a Surgical Instrument," filed on Nov. 25, 2014, published as U.S. Pat. Pub. No. 2015/0148835 on May 28, 2015, the disclosure of which is incorporated by reference herein. It should be understood that the teachings herein may be readily combined with the teachings of those references and the various other references cited herein. Other suitable examples will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft assembly; and
   (b) an end effector located at a distal end of the shaft assembly, wherein the end effector comprises:
      (i) an ultrasonic blade extending distally therealong relative to the shaft assembly, wherein the ultrasonic blade is configured to vibrate at an ultrasonic frequency, and
      (ii) a clamp arm comprising a clamp pad movable toward the ultrasonic blade from an open position to a first stage followed by a second stage toward a closed position,
      wherein the clamp arm is configured to compress tissue against the ultrasonic blade with only a distal portion of the clamp pad in the first stage,
      wherein the clamp arm is configured to compress tissue against the ultrasonic blade with the distal portion and a proximal portion of the clamp pad in the second stage, such that the tissue compression begins at the distal portion and subsequently progresses toward the proximal portion, wherein the clamp arm further comprises a shank member, wherein the shank member is pivotally connected relative to the shaft assembly, and wherein the clamp pad is pivotally connected relative to the shank member.

2. The apparatus of claim 1, wherein the clamp arm comprises a distal pad carrying member, wherein the shank member is operable to drive the distal pad carrying member toward the ultrasonic blade, wherein the clamp pad is secured to the distal pad carrying member.

3. The apparatus of claim 2, wherein the clamp arm further comprises a resilient feature joining the shank member and the distal pad carrying member.

4. The apparatus of claim 3, wherein the resilient feature comprises a leaf spring.

5. The apparatus of claim 3, wherein the resilient feature is configured to resiliently bias the distal portion of the clamp pad toward the ultrasonic blade.

6. The apparatus of claim 5, wherein the resilient feature is configured to deform during a transition from the first stage to the second stage.

7. The apparatus of claim 3, wherein the resilient feature is configured to enable the distal pad carrying member to pivot relative to the shank member.

8. The apparatus of claim 3, wherein the resilient feature comprises a plurality of segments.

9. The apparatus of claim 2, wherein the distal pad carrying member has a dogleg feature, wherein the dogleg feature is configured to bias the distal portion of the clamp pad toward the ultrasonic blade.

10. The apparatus of claim 1, wherein the clamp arm further comprises a resilient member, wherein the resilient member is configured to resiliently bias the distal portion of the clamp pad toward the ultrasonic blade.

11. The apparatus of claim 10, wherein the resilient member has at least one bend, wherein the clamp pad is secured to the resilient member.

12. The apparatus of claim 11, wherein the clamp pad follows the at least one bend of the resilient member, wherein the clamp pad is flexible such that the clamp pad is configured to deform with the at least one bend of the resilient member during a transition from the first stage to the second stage.

13. The apparatus of claim 10, wherein, wherein the clamp pad is pivotably coupled with the shank member at a pivot, wherein the resilient member is interposed between a distal end of the clamp pad and a distal end of the shank member such that the resilient member is configured to resiliently bias the clamp pad about the pivot.

14. The apparatus of claim 1, wherein the clamp pad further comprises a proximal segment and a distal segment.

15. The apparatus of claim 1, further comprising a handle assembly and a user feedback feature, wherein the shaft assembly extends distally from the handle assembly, and wherein the wherein the user feedback feature is configured to provide one or both of audible or tactile feedback through the handle assembly to indicate a transition from the first stage to the second stage.

16. The apparatus of claim 1, wherein the clamp pad is configured to distally move relative to the ultrasonic blade as the clamp arm transitions from the first stage to the second stage.

17. The apparatus of claim 1, wherein the clamp pad extends along a first plane that is obliquely oriented relative to an opposing surface of the ultrasonic blade in the first stage, and wherein the clamp pad extends along a second plane that is parallel relative to the opposing surface of the ultrasonic blade in the second stage.

18. An apparatus comprising:
  (a) a shaft assembly; and
  (b) an end effector located at a distal end of the shaft assembly, wherein the end effector comprises:
    (i) an ultrasonic blade extending distally therealong relative to the shaft assembly, wherein the ultrasonic blade is configured to vibrate at an ultrasonic frequency, and
    (ii) a clamp arm movable toward the ultrasonic blade from an open position to a first stage followed by a second stage toward a closed position, wherein the clamp arm comprises:
      (A) a shank member pivotally connected relative to the shaft assembly, and
      (B) a clamp pad pivotally connected relative to the shank member,
    wherein the clamp arm is configured to compress tissue against the ultrasonic blade with only a distal portion of the clamp pad in the first stage, wherein the clamp arm is configured to compress tissue against the ultrasonic blade with the distal portion and a proximal portion of the clamp pad in the second stage such that the tissue compression begins at the distal portion and subsequently progresses toward the proximal portion,
  wherein the clamp pad is configured to distally move relative to the ultrasonic blade as the clamp arm transitions from the first stage to the second stage, and
  wherein the clamp pad extends along a first plane that is obliquely oriented relative to an opposing surface of the ultrasonic blade in the first stage, and wherein the clamp pad extends along a second plane that is parallel relative to the opposing surface of the ultrasonic blade in the second stage.

19. An apparatus comprising:
  (a) a shaft assembly; and
  (b) an end effector located at a distal end of the shaft assembly, wherein the end effector comprises:
    (i) an ultrasonic blade, wherein the ultrasonic blade is configured to vibrate at an ultrasonic frequency, and
    (ii) a clamp arm comprising a clamp pad movable toward the ultrasonic blade from an open position to a first stage followed by a second stage toward a closed position,
  wherein the clamp arm is configured to compress tissue against the ultrasonic blade with only a distal portion of the clamp pad in the first stage, wherein the clamp pad extends along a first plane that is obliquely oriented relative to an opposing surface of the ultrasonic blade in the first stage,
  wherein the clamp arm is configured to compress tissue against the ultrasonic blade with the distal portion and a proximal portion of the clamp pad in the second stage, such that the tissue compression begins at the distal portion and subsequently progresses toward the proximal portion, wherein the clamp pad is configured to distally move relative to the ultrasonic blade as the clamp arm transitions from the first stage to the second stage such that the clamp pad extends along a second plane that is parallel relative to the opposing surface of the ultrasonic blade in the second stage.

* * * * *